(12) United States Patent
Kudo et al.

(10) Patent No.: US 11,053,437 B2
(45) Date of Patent: Jul. 6, 2021

(54) COMPOUND, MATERIAL FOR ORGANIC ELECTROLUMINESCENT DEVICES, ORGANIC ELECTROLUMINESCENT DEVICE AND ELECTRONIC DEVICE

(71) Applicant: IDEMITSU KOSAN CO., LTD., Tokyo (JP)

(72) Inventors: Yu Kudo, Sodegaura (JP); Tasuku Haketa, Sodegaura (JP); Hirokatsu Ito, Sodegaura (JP); Yusuke Takahashi, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 17/097,031

(22) Filed: Nov. 13, 2020

(65) Prior Publication Data

US 2021/0062082 A1    Mar. 4, 2021

Related U.S. Application Data

(63) Continuation of application No. PCT/JP2020/024931, filed on Jun. 25, 2020.

(30) Foreign Application Priority Data

Jun. 28, 2019 (JP) .............................. JP2019-122081

(51) Int. Cl.
  *C09K 11/06*  (2006.01)
  *H01L 51/00*  (2006.01)
  *H01L 51/50*  (2006.01)

(52) U.S. Cl.
  CPC .......... *C09K 11/06* (2013.01); *H01L 51/0059* (2013.01); *H01L 51/0073* (2013.01);
  (Continued)

(58) Field of Classification Search
  CPC ............ C09K 11/06; C09K 2211/1022; H01L 51/0073; H01L 51/0059; H01L 51/0074
  See application file for complete search history.

(56) References Cited

U.S. PATENT DOCUMENTS 8,367,222 B2    2/2013  Arakane et al.
8,823,050 B2    9/2014  Wu
(Continued)

FOREIGN PATENT DOCUMENTS

CN    101931054 B    12/2010
CN    103724151 B    7/2015
(Continued)

OTHER PUBLICATIONS

International Search Report dated Aug. 25, 2020, in PCT/JP2020/024931.
(Continued)

*Primary Examiner* — Anthony Ho
(74) *Attorney, Agent, or Firm* — Oblon, McClelland, Maier & Neustadt, L.L.P.

(57) ABSTRACT

Provided are a compound capable of more improving the performance of organic EL devices, an organic electroluminescent device having a more improved device performance, and an electronic device including such an organic electroluminescent device; precisely, a compound represented by the following formula (1);
(Continued)

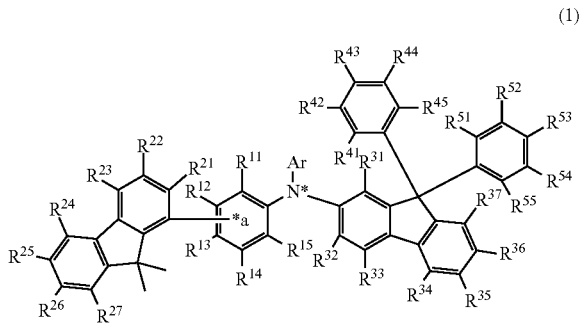

(1)

wherein N*, Ar, *a, $R^{11}$ to $R^{15}$, $R^{21}$ to $R^{27}$, $R^{31}$ to $R^{37}$, $R^{41}$ to $R^{45}$, and $R^{51}$ to $R^{55}$ are as defined in the description, an organic electroluminescent device containing the compound, and an electronic device including such an organic electroluminescent device.

30 Claims, 1 Drawing Sheet

(52) U.S. Cl.
CPC .. *H01L 51/0074* (2013.01); *C09K 2211/1022* (2013.01); *H01L 51/5056* (2013.01)

(56) References Cited

U.S. PATENT DOCUMENTS

| | | | |
|---|---|---|---|
| 8,841,833 B2 | 9/2014 | Higo et al. | |
| 8,940,408 B2 | 1/2015 | Lee et al. | |
| 9,054,331 B2 | 6/2015 | Higo et al. | |
| 9,583,714 B2 | 2/2017 | Funyuu et al. | |
| 10,103,338 B1 | 10/2018 | Nakano et al. | |
| 10,109,803 B1 | 10/2018 | Nakano et al. | |
| 10,109,804 B1 | 10/2018 | Nakano et al. | |
| 10,263,192 B2 | 4/2019 | Kawamura et al. | |
| 2009/0167161 A1 | 7/2009 | Yabunouchi et al. | |
| 2016/0240783 A1 | 8/2016 | Yen et al. | |
| 2017/0194569 A1 | 7/2017 | Kim et al. | |
| 2017/0288147 A1 | 10/2017 | Fujita et al. | |
| 2017/0331039 A1 | 11/2017 | Lim et al. | |
| 2017/0331048 A1 | 11/2017 | Cho et al. | |
| 2018/0179206 A1 | 6/2018 | Haketa et al. | |
| 2018/0182974 A1 | 6/2018 | Haketa et al. | |
| 2018/0277769 A1 | 9/2018 | Kawamura et al. | |
| 2019/0044085 A1 | 2/2019 | Jeong et al. | |
| 2019/0097138 A1 | 3/2019 | Lee et al. | |
| 2019/0135730 A1 | 5/2019 | Mun et al. | |
| 2019/0148640 A1 | 5/2019 | Lim et al. | |
| 2019/0148650 A1 | 5/2019 | Kwak et al. | |
| 2019/0185411 A1 | 6/2019 | Lee et al. | |
| 2019/0194219 A1 | 6/2019 | Kawamura et al. | |
| 2019/0225581 A1 | 7/2019 | Scheible | |

FOREIGN PATENT DOCUMENTS

| | | |
|---|---|---|
| CN | 107046100 B | 8/2017 |
| CN | 107068876 B | 8/2017 |
| CN | 107068880 B | 8/2017 |
| CN | 107068887 B | 8/2017 |
| CN | 107963973 A | 4/2018 |
| CN | 108346756 A | 7/2018 |
| CN | 108623481 A | 10/2018 |
| CN | 108774515 A | 11/2018 |
| CN | 107068888 B | 12/2018 |
| CN | 110010783 A | 7/2019 |
| EP | 3 278 693 A1 | 2/2018 |
| EP | 3 010 066 B1 | 2/2019 |
| JP | 11-144875 A | 5/1999 |
| JP | 2008-300503 A | 12/2008 |
| JP | 2009-010364 A | 1/2009 |
| JP | 2016-153394 A | 8/2016 |
| JP | 2018-125504 A | 8/2018 |
| JP | 2018-529644 A | 10/2018 |
| KR | 10-2013-0121597 A | 11/2013 |
| KR | 10-2014-0033301 A | 3/2014 |
| KR | 10-2017-0093272 A | 6/2017 |
| KR | 10-2017-0088601 A | 8/2017 |
| KR | 10-2017-0136391 A | 12/2017 |
| KR | 10-1961346 B1 | 12/2017 |
| KR | 10-2018-0042944 A | 4/2018 |
| KR | 10-2018-0053121 A | 5/2018 |
| KR | 10-2018-0060582 A | 6/2018 |
| KR | 10-2018-0061461 A | 6/2018 |
| KR | 10-2018-0063707 A | 6/2018 |
| KR | 10-2018-0075981 A | 7/2018 |
| KR | 10-2018-0080603 A | 7/2018 |
| KR | 10-2018-0137315 A | 12/2018 |
| KR | 10-2019-039491 A | 4/2019 |
| TW | 201021614 A | 6/2010 |
| WO | WO 2012/034626 A1 | 3/2012 |
| WO | WO 2014/034795 A1 | 3/2014 |
| WO | WO 2015/082056 A1 | 6/2015 |
| WO | WO 2017/209538 A1 | 12/2017 |
| WO | WO 2018/026197 A1 | 2/2018 |
| WO | WO 2018/034517 A1 | 2/2018 |
| WO | WO 2018/038544 A1 | 3/2018 |
| WO | WO 2018/123924 A1 | 7/2018 |
| WO | WO 2018/157981 A1 | 9/2018 |
| WO | WO 2018/158232 A1 | 9/2018 |
| WO | WO 2018/159970 A1 | 9/2018 |
| WO | WO 2018/164265 A1 | 9/2018 |
| WO | WO 2018/174293 A1 | 9/2018 |
| WO | WO 2018/182221 A1 | 10/2018 |
| WO | WO 2018/186396 A1 | 10/2018 |
| WO | WO 2018/186622 A1 | 10/2018 |
| WO | WO 2018/211377 A1 | 11/2018 |
| WO | WO 2018/216799 A1 | 11/2018 |
| WO | WO 2018/221871 A1 | 12/2018 |
| WO | WO 2019/004764 A1 | 1/2019 |
| WO | WO 2019/039428 A1 | 2/2019 |
| WO | WO 2019/063886 A1 | 4/2019 |
| WO | WO 2019/088231 A1 | 5/2019 |
| WO | WO 2019/115577 A1 | 6/2019 |
| WO | WO 2019/139419 A1 | 7/2019 |
| WO | WO 2018/186404 A1 | 2/2020 |

OTHER PUBLICATIONS

Japanese Office Action dated Nov. 10, 2020, in Japanese Patent Application No. 2020-556334.

COMPOUND, MATERIAL FOR ORGANIC ELECTROLUMINESCENT DEVICES, ORGANIC ELECTROLUMINESCENT DEVICE AND ELECTRONIC DEVICE

CROSS-REFERENCE TO RELATED APPLICATIONS

This application is a continuation of International Patent Application No. PCT/JP2020/02493 filed on Jun. 25, 2020, and claims priority to Japanese Patent Application No. 2019-122081 filed on Jun. 28, 2019, all of which are incorporated herein by reference in their entireties.

TECHNICAL FIELD

The present invention relates to a compound, a material for organic electroluminescent devices, an organic electroluminescent device, and an electronic device containing the organic electroluminescent device.

BACKGROUND ART

An organic electroluminescent device (hereinafter may be expressed as "organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, energy is released as light. Therefore, it is important for obtaining an organic EL device with a high efficiency to develop a compound that transports electrons or holes into the light emitting region efficiently and facilitates the recombination of electrons and holes.

PTLs 1 to 7 disclose compounds for use as a material for organic electroluminescent devices.

CITATION LIST

Patent Literature

PTL 1: JP 11-144875A
PTL 2: WO2014/034795A1
PTL 3: WO2015/082056A1
PTL 4: EP3010066B1
PTL 5: KR2018-0042944
PTL 6: KR2017-0136391
PTL 7: WO2012/034626A1

SUMMARY OF INVENTION

Technical Problem

Heretofore, various compounds for organic EL devices have been reported. However, compounds that further improve the performance of organic EL devices have been still demanded.

The present invention has been made to solve the above problems and an object of the invention is to provide a compound further improving the performance of organic EL devices, an organic EL device having their performance further improved, and an electronic device containing such an organic EL device.

Solution to Problem

The present inventors have made assiduous studies about the performance of the organic EL devices containing the compounds described in PTLs 1 to 7 and, as a result, have found that a monoamine compound, in which a 9,9-dimethylfluoren-1-yl skeleton-having phenyl group, a 9,9-diphenylfluoren-2-yl skeleton, and a specific aryl group or heterocyclic group directly bond to the center nitrogen atom, can provide an organic EL device having a more improved device performance.

In one aspect, the present invention provides a compound represented by the following formula (1):

(1)

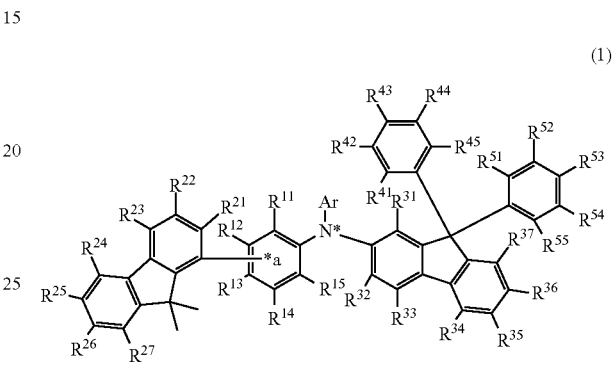

wherein,
N* represents a center nitrogen atom;
Ar represents a group represented by any of the following formulae (2) to (4);

(2)

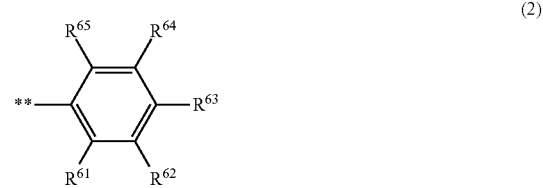

(3)

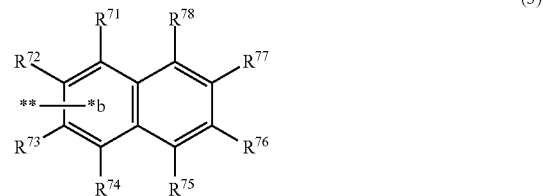

(4)

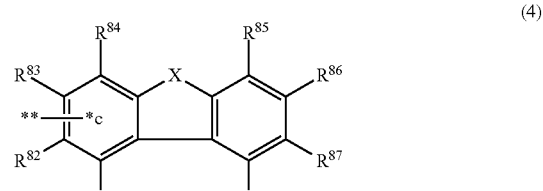

X represents an oxygen atom or a sulfur torn;
$R^{61}$ to $R^{65}$, $R^{71}$ to $R^{78}$, and $R^{81}$ to $R^{88}$ each are independently selected from a hydrogen atom, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, provided that one selected from $R^{71}$ to $R^{78}$ is a single bond bonding to *b, one selected from $R^{81}$ to $R^{88}$ is a single bond bonding to *c, and ** represents a bonding position to the center nitrogen atom N*;

$R^{11}$ to $R^{15}$, $R^{21}$ to $R^{27}$, $R^{41}$ to $R^{45}$, and $R^{51}$ to $R^{55}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, provided that one selected from $R^{11}$ to $R^{15}$ is a single bond bonding to *a;

$R^{31}$ to $R^{37}$ each are independently selected from a hydrogen atom, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group;

$R_{901}$, $R_{902}$, and $R_{903}$ each are independently selected from a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms;

one pair or more of combinations formed of neighboring two or more selected from $R^{21}$ to $R^{27}$ and $R^{31}$ to $R^{37}$ bond to each other to form a substituted or unsubstituted single ring, or bond to each other to form a substituted or unsubstituted condensed ring, or do not bond to each other;

$R^{45}$ and $R^{51}$ bond to each other to form a single bond that bonds the two benzene rings to which they bond, or do not bond to each other.

In another aspect, the present invention provides a material for organic EL devices containing the compound represented by the above-mentioned formula (1).

In still another aspect, the present invention provides an organic electroluminescent device including an anode, a cathode, and an organic layer arranged between the anode and the cathode, wherein the organic layer includes a light-emitting layer, and at least one layer of the organic layer contains the compound represented by the above-mentioned formula (1).

In still another aspect, the present invention provides an electronic device including the above-mentioned organic electroluminescent device.

Advantageous Effects of Invention

An organic EL device containing the compound represented by the formula (1) exhibits an improved device performance.

DESCRIPTION OF EMBODIMENTS

Definition

Figure 1:
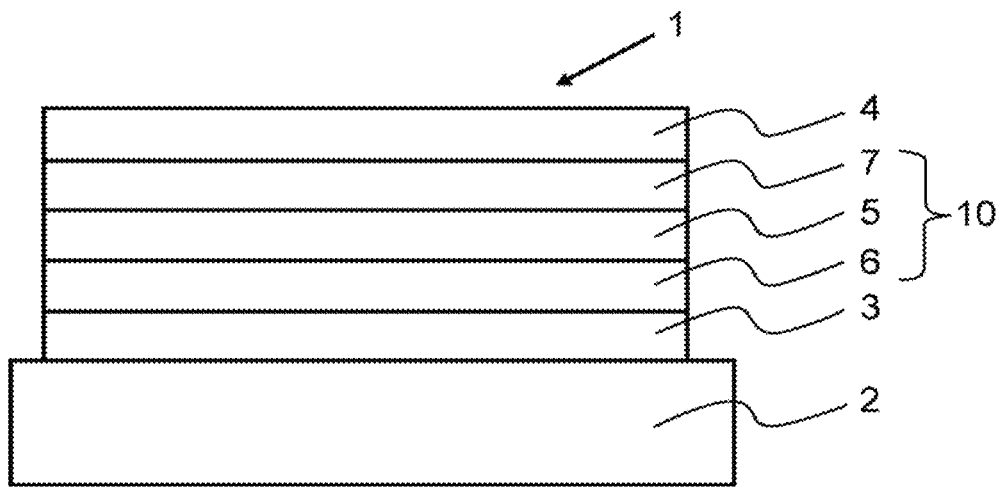
FIG. 1 is a schematic view showing one example of a layered configuration of an organic EL device of an embodiment of the invention.

In this description, the definition of "hydrogen atom" includes isotopes different in the neutron numbers, i.e., light hydrogen (protium), heavy hydrogen (deuterium), and tritiated hydrogen (tritium).

In this description, the number of ring carbon atoms means the number of the carbon atoms included in the atoms that form the ring itself of a compound in which a series of atoms are bonded to form a cyclic compound (for example, a monocyclic compound, a condensed ring compound, a crosslinked compound, a carbocyclic compound, and a heterocyclic compound). In the case where the ring has a substituent, the carbon atom in the substituent is not included in the ring carbon atom. Unless otherwise noted, the same applies to the "number of ring carbon atoms" mentioned below. For example, a benzene ring has 6 ring carbon atoms, a naphthalene ring has 10 ring carbon atoms, a pyridine ring has 5 ring carbon atoms, a furan ring has 4 ring carbon atoms. Also, for example, a 9,9-diphenylfluorenyl group has 13 ring carbon atoms, and a 9,9'-spirobifluorenyl group has 25 ring carbon atoms.

In the case where a benzene ring has, for example, an alkyl substituent, the carbon atom in the alkyl substituent is not counted as the ring carbon atom of the benzene ring. Therefore, an alkyl-substituted benzene ring has 6 ring carbon atoms. In the case where a naphthalene ring has, for example, an alkyl substituent, the carbon atom in the alkyl substituent is not counted as the ring carbon atom of the naphthalene ring. Therefore, an alkyl-substituted naphthalene ring has 10 ring carbon atoms.

In this description, the number of ring atoms means the number of the atoms that form the ring itself of a compound in which a series of atoms are bonded to form a cyclic compound (for example, a monocyclic compound, a condensed ring compound, and a ring aggregation). (Examples of the compound of the type include a monocyclic compound, a condensed cyclic compound, a crosslinked compound, a carbocyclic compound, and a heterocyclic compound.) Atoms not forming a ring (for example, a hydrogen atom that terminate the bond of atoms constituting a ring), and atoms included in a substituent in the case where the ring is substituted with a substituent are not counted in the number of ring atoms. Unless otherwise noted, the same applies to the "number of ring atoms" mentioned below. For example, a pyridine ring has 6 ring atoms, a quinazoline ring has 10 ring atoms, and a furan ring has 5 ring atoms. For example, the number of the hydrogen atoms bonding to a pyridine ring, or the atoms constituting a substituent is not counted as the ring atom of a pyridine ring. Therefore, the number of the ring atoms of a pyridine ring to which a hydrogen atom or a substituent bonds is 6. Also, for example, the number of the hydrogen atoms bonding to a quinazoline ring, or the atoms constituting a substituent is not counted as the ring atom of a quinazoline ring. Therefore, the number of the ring atoms of a quinazoline ring to which a hydrogen atom or a substituent bonds is 10.

In this description, the expression of "XX to YY carbon atoms" in a "substituted or unsubstituted group ZZ having XX to YY carbon atoms" is the number of carbon atoms of the unsubstituted group ZZ and does not include any carbon atom in the substituent of the substituted group ZZ. Here, "YY" is larger than "XX", and "XX" means an integer of 1 or more and "YY" means an integer of 2 or more.

In this description, the expression of "XX to YY atoms" in a "substituted or unsubstituted group ZZ having XX to YY atoms" is the number of atoms of the unsubstituted group ZZ and does not include any atom in the substituent of the substituted group ZZ. Here, "YY" is larger than "XX", and "XX" means an integer of 1 or more and "YY" means an integer of 2 or more.

In this description, an unsubstituted ZZ group represents a case where "a substituted or unsubstituted ZZ group" is "an unsubstituted ZZ group", and a substituted ZZ group represents a case where "a substituted or unsubstituted ZZ group" is "a substituted ZZ group".

In this description, "unsubstituted" in a case of "a substituted or unsubstituted ZZ group" means that the hydrogen atom in the ZZ group is not substituted with a substituent.

Also in this description, "substituted" in a case of "a substituted or unsubstituted ZZ group" means that one or more hydrogen atoms in the ZZ group are substituted with substituent(s). The same applies to a case of "a BB group substituted with a AA group", that is, this means that one or more hydrogen atoms in the BB group are substituted with AA group(s).

[Substituents Referred to this Description]

The substituents referred to this description are explained below.

The number of ring carbon atoms of "an unsubstituted aryl group" referred to in this description is, unless otherwise specifically noted in this description, 6 to 50, preferably 6 to 30, more preferably 6 to 18.

The number of ring atoms of "an unsubstituted heterocyclic group" referred to in this description is, unless otherwise specifically noted in this description, 5 to 50, preferably 5 to 30, more preferably 5 to 18.

The number of carbon atoms of "an unsubstituted alkyl group" referred to in this description is, unless otherwise specifically noted in this description, 1 to 50, preferably 1 to 20, more preferably 1 to 6.

The number of carbon atoms of "an unsubstituted alkenyl group" referred to in this description is, unless otherwise specifically noted in this description, 2 to 50, preferably 2 to 20, more preferably 2 to 6.

The number of carbon atoms of "an unsubstituted alkynyl group" referred to in this description is, unless otherwise specifically noted in this description, 2 to 50, preferably 2 to 20, more preferably 2 to 6.

The number of ring carbon atoms of "an unsubstituted cycloalkyl group" referred to in this description is, unless otherwise specifically noted in this description, 3 to 50, preferably 3 to 20, more preferably 3 to 6.

The number of ring carbon atoms of "an unsubstituted arylene group" referred to in this description is, unless otherwise specifically noted in this description, 6 to 50, preferably 6 to 30, more preferably 6 to 18.

The number of ring atoms of "an unsubstituted divalent heterocyclic group" referred to in this description is, unless otherwise specifically noted in this description, 5 to 50, preferably 5 to 30, more preferably 5 to 18.

The number of carbon atoms of "an unsubstituted alkylene group" referred to in this description is, unless otherwise specifically noted in this description, 1 to 50, preferably 1 to 20, more preferably 1 to 6.

"Substituted or Unsubstituted Aryl Group"

Specific examples (group G1 of specific examples) of "a substituted or unsubstituted aryl group" referred to in this description include the following unsubstituted aryl groups (Group G1A of specific examples) and substituted aryl groups (Group G1B of specific examples). (Here, an unsubstituted aryl group means a case of "an unsubstituted aryl group" of "a substituted or unsubstituted aryl group", and a substituted aryl group means a case of "a substituted aryl group" of "a substituted or unsubstituted aryl group".) In this description, a simple expression of "an aryl group" includes both "an unsubstituted aryl group" and "a substituted aryl group".

The "substituted aryl group" means a group of "an unsubstituted aryl group" in which one or more hydrogen atoms are substituted with substituent(s). Examples of the "substituted aryl group" include groups of the "unsubstituted aryl group" of the following Group G1A of specific examples in which one or more hydrogen atoms are substituted with substituent(s), and examples of substituted aryl groups of the following Group G1B of specific examples. Examples of the "unsubstituted aryl group" and examples of the "substituted aryl group" listed herein are some mere examples, and the "substituted aryl group" referred to in this description further includes groups of the "substituted aryl group" of the following Group G1B of specific examples in which the hydrogen atom bonding to the carbon atom of the aryl group itself is further substituted with a substituent, and groups of the "substituted aryl group" of the following Group G1B of specific examples in which the hydrogen atom of the substituent of the aryl group is further substituted with a substituent.

Unsubstituted aryl groups (Group G1A of specific examples):
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group, a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived from a cyclic structure represented by the following general formulae (TEMP-1) to (TEMP-15), by removing one hydrogen atom from the cyclic structure.

(TEMP-1)

(TEMP-2)

(TEMP-3)

(TEMP-4)

(TEMP-5)

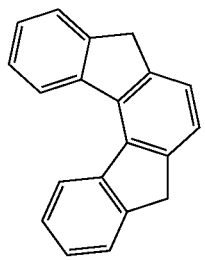
(TEMP-6)

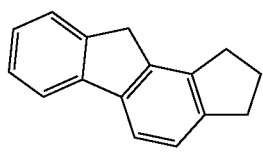
(TEMP-7)

(TEMP-8)

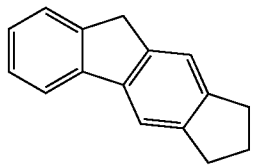
(TEMP-9)

(TEMP-10)

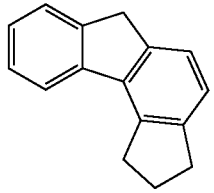
(TEMP-11)

(TEMP-12)

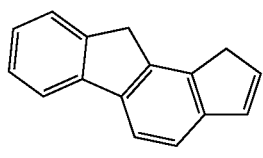
(TEMP-13)

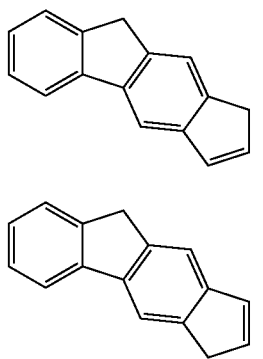

-continued

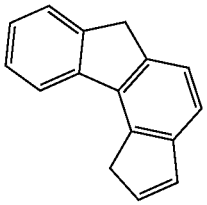

(TEMP-14)

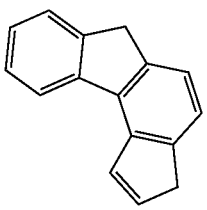

(TEMP-15)

Substituted aryl groups (Group G1B of specific examples):
an o-tolyl group,
a m-tolyl group,
a p-tolyl group,
a para-xylyl group,
a meta-xylyl group,
an ortho-xylyl group,
a para-isopropylphenyl group,
a meta-isopropylphenyl group,
an ortho-isopropylphenyl group,
a para-t-butylphenyl group,
a meta-t-butylphenyl group,
an ortho-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
a group of the monovalent group derived from the cyclic structure represented by the general formulae (TEMP-1) to (TEMP-15) in which one or more hydrogen atoms are substituted with substituent(s).

"Substituted or Unsubstituted Heterocyclic Group"

The "heterocyclic group" referred to in this description is a cyclic group containing at least one hetero atom as the ring atom. Specific examples of the hetero atom include a nitrogen atom, an oxygen atom, a sulfur atom, a silicon atom, a phosphorus atom, and a boron atom.

The "heterocyclic group" referred to in this description is a monocyclic group, or a condensed cyclic group.

The "heterocyclic group" referred to in this description is an aromatic heterocyclic group or a nonaromatic heterocyclic group.

Specific examples (Group G2 of specific examples) of the "substituted or unsubstituted heterocyclic group" referred to in this description includes the following unsubstituted heterocyclic groups (Group G2A of specific examples), and the following substituted heterocyclic groups (Group G2B of specific examples). (Here, the unsubstituted heterocyclic group indicates a case where the "substituted or unsubstituted heterocyclic group" is an "unsubstituted heterocyclic group"; and the substituted heterocyclic group indicates a case where the "substituted or unsubstituted heterocyclic group" is a "substituted heterocyclic group".) In this description, a mere expression of "a heterocyclic group" includes both "an unsubstituted heterocyclic group" and "a substituted heterocyclic group".

The "substituted heterocyclic group" means a group of "an unsubstituted heterocyclic group" in which one or more hydrogen atoms are substituted with substituent(s). Specific examples of the "substituted heterocyclic group" include groups of the "unsubstituted heterocyclic group" of the following Group G2A of specific examples in which the hydrogen atom is substituted, and examples of the substituted heterocyclic group of the following Group G2B of specific examples. Examples of the "unsubstituted heterocyclic group" and examples of the "substituted heterocyclic group" listed herein are some mere examples, and the "substituted heterocyclic group" referred to in this description further includes groups of the "substituted heterocyclic group" of the following Group G2B of specific examples in which the hydrogen atom bonding to the ring atom of the heterocyclic group itself is further substituted with a substituent, and groups of the "substituted heterocyclic group" of the following Group G2B of specific examples in which the hydrogen atom of the substituent of the heterocyclic group is further substituted with a substituent.

Examples of Group G2A of specific examples include the following nitrogen atom-containing, unsubstituted heterocyclic groups (Group G2A1 of specific examples), the following oxygen atom-containing, unsubstituted heterocyclic groups (Group G2A2 of specific examples), the following sulfur atom-containing, unsubstituted heterocyclic groups (Group G2A3 of specific examples), and monovalent heterocyclic groups derived from cyclic structures represented by the following general formulae (TEMP-16) to (TEMP-33) by removing one hydrogen atom from each cyclic structure (Group G2A4 of specific examples).

Examples of Group G2B of specific examples include the following nitrogen atom-containing, substituted heterocyclic groups (Group G2B1 of specific examples), the following oxygen atom-containing, substituted heterocyclic groups (Group G2B2 of specific examples), the following sulfur atom-containing, substituted heterocyclic groups (Group G2B3 of specific examples), and monovalent heterocyclic groups derived from cyclic structures represented by the following general formulae (TEMP-16) to (TEMP-33) by substituting one or more hydrogen atoms with substituent(s) (Group G2B4 of specific examples).

Nitrogen atom-containing, unsubstituted heterocyclic groups (Group G2A1 of specific examples):
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group, an indolyl group,
an isoindolyl group,
an indolidinyl group,
a quinolidinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and a diazacarbazolyl group.

Oxygen atom-containing, unsubstituted heterocyclic groups (Group G2A2 of specific examples):
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Sulfur atom-containing, unsubstituted heterocyclic groups (Group G2A3 of specific examples):
a thienyl group,
a thiazolyl group,
an isothiazolyl group,
a thiadiazolyl group,
a benzothiophenyl group (a benzothienyl group),
an isobenzothiophenyl group (an isobenzothienyl group),
a dibenzothiophenyl group (a dibenzothienyl group),
a naphthobenzothiophenyl group (a naphthobenzothienyl group),
a benzothiazolyl group,
a benzisothiazolyl group,
a phenothiazinyl group,
a dinaphthothiophenyl group (a dinaphthothienyl group),
an azadibenzothiophenyl group (an azadibenzothienyl group),
a diazadibenzothiophenyl group (a diazadibenzothienyl group),
an azanaphthobenzothiophenyl group (an azanaphthobenzothienyl group), and
a diazanaphthobenzothiophenyl group (a diazanaphthobenzothienyl group).

Monovalent heterocyclic groups derived from cyclic structures represented by the following general formulae (TEMP-16) to (TEMP-33) by removing one hydrogen atom from each cyclic structure (Group G2A4 of specific examples):

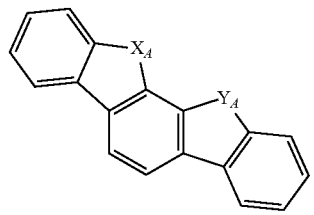

(TEMP-16)

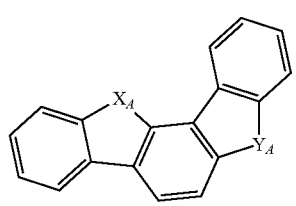

(TEMP-17)

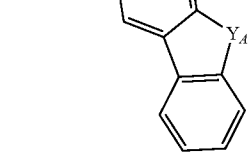

(TEMP-18)

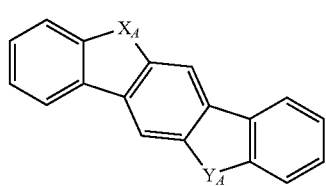

(TEMP-19)

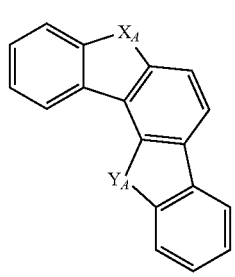

(TEMP-20)

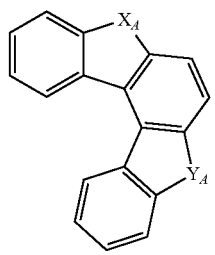

(TEMP-21)

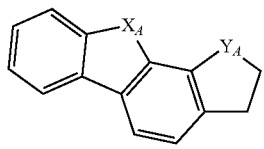
(TEMP-22)

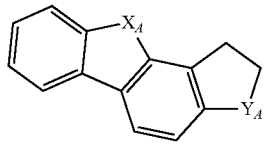
(TEMP-23)

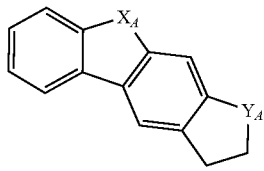
(TEMP-24)

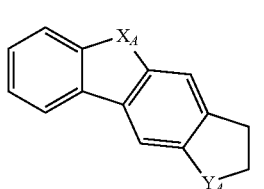
(TEMP-25)

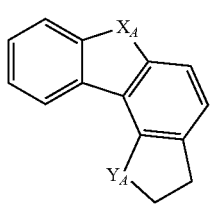
(TEMP-26)

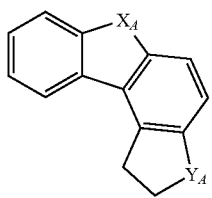
(TEMP-27)

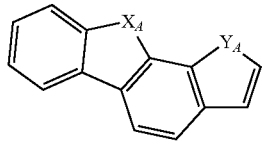
(TEMP-28)

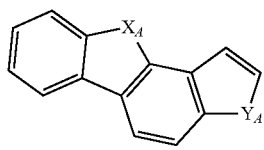
(TEMP-29)

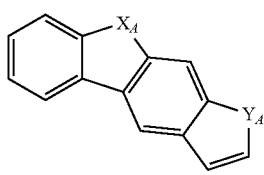
(TEMP-30)

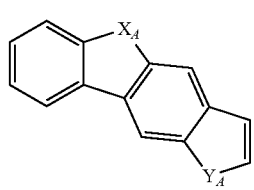
(TEMP-31)

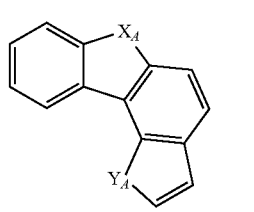
(TEMP-32)

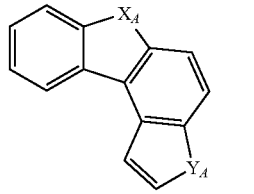
(TEMP-33)

In the above general formulae (TEMP-16) to (TEMP-33), $X_A$ and $Y_A$ each independently represent an oxygen atom, a sulfur atom, NH or $CH_2$, provided that at least one of $X_A$ and $Y_A$ is an oxygen atom, a sulfur atom or NH.

In the case where at least any of $X_A$ and $Y_A$ is NH or $CH_2$ in the above general formulae (TEMP-16) to (TEMP-33), the monovalent heterocyclic groups derived from the cyclic structures represented by the general formulae (TEMP-16) to (TEMP-33) include monovalent groups derived from these by removing one hydrogen atom from NH or $CH_2$.

Nitrogen atom-containing, substituted heterocyclic groups (Group G2B1 of specific examples):
a (9-phenyl)carbazolyl group,
a (9-biphenylyl)carbazolyl group,
a (9-phenyl)phenylcarbazolyl group,
a (9-naphthyl)carbazolyl group,
a diphenylcarbazole-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

Oxygen atom-containing, substituted heterocyclic groups (Group G2B2 of specific examples):
a phenyldibenzofuranyl group,
a methyldibenzofuranyl group,
a t-butyldibenzofuranyl group, and
a monovalent residue of spiro[9H-xanthene-9,9'-[9H]fluorene].

Sulfur atom-containing, substituted heterocyclic groups (Group G2B3 of specific examples):
a phenyldibenzothiophenyl group,
a methyldibenzothiophenyl group,
a t-butyldibenzothiophenyl group, and
a monovalent residue of spiro[9H-thioxanthene-9,9'-[9H]fluorene].

Monovalent heterocyclic groups derived from cyclic structures represented by the above-mentioned general formulae (TEMP-16) to (TEMP-33) by substituting one or more hydrogen atoms with substituent(s) (Group G2B4 of specific examples):

The above-mentioned "one or more hydrogen atoms of a monovalent heterocyclic group" mean one or more hydrogen atoms selected from a hydrogen atom bonding to the ring carbon atom of the monovalent heterocyclic group, a hydrogen atom bonding to the nitrogen atom in the case where at least any of XA and YA is NH, and a hydrogen atom of a methylene group in the case where one of XA and YA is $CH_2$.

"Substituted or Unsubstituted Alkyl Group"

Specific examples of the "substituted or unsubstituted alkyl group" referred to in this description (Group G3 of specific examples) include the following unsubstituted alkyl groups (Group G3A of specific examples) and the following substituted alkyl groups (Group G3B of specific examples). (Here, the unsubstituted alkyl group indicates a case where the "substituted or unsubstituted alkyl group" is an "unsubstituted alkyl group"; and the substituted alkyl group indicates a case where the "substituted or unsubstituted alkyl group" is a "substituted alkyl group".) Hereinunder, a mere expression of "an alkyl group" includes both "an unsubstituted alkyl group" and "a substituted alkyl group".

The "substituted alkyl group" means a group of "an unsubstituted alkyl group" in which one or more hydrogen atoms are substituted with substituent(s). Specific examples of the "substituted alkyl group" include groups of the "unsubstituted alkyl group" of the following Group G3A of specific examples in which one or more hydrogen atoms are substituted, and examples of the substituted alkyl group (Group G3B of specific examples). In this description, the alkyl group in the "unsubstituted alkyl group" means a chainlike alkyl group. Accordingly, the "unsubstituted alkyl group" includes a straight-chain "unsubstituted alkyl group", and a branched "unsubstituted alkyl group". Examples of the "unsubstituted alkyl group" and examples of the "substituted alkyl group" listed herein are some mere examples, and the "substituted alkyl group" referred to in this description further includes groups of the "substituted alkyl group" of Group G3B of specific examples in which the hydrogen atom of the alkyl group itself is further substituted with a substituent, and groups of the "substituted alkyl group" of Group G3B of specific examples in which the hydrogen atom of the substituent of the alkyl group is further substituted with a substituent.

Unsubstituted alkyl groups (Group G3A of specific examples):
a methyl group,
an ethyl group,
an n-propyl group,
an isopropyl group,
an n-butyl group,
an isobutyl group,
an s-butyl group, and
a t-butyl group.

Substituted alkyl groups (Group G3B of specific examples):
a heptafluoropropyl group (including isomers),
a pentafluoroethyl group,
a 2,2,2-trifluoroethyl group, and
a trifluoromethyl group.

"Substituted or Unsubstituted Alkenyl Group"

Specific examples of the "substituted or unsubstituted alkenyl group" referred to in this description (Group G4 of specific examples) include the following unsubstituted alkenyl groups (Group G4A of specific examples) and the following substituted alkenyl groups (Group G4B of specific examples). (Here, the unsubstituted alkenyl group indicates a case where the "substituted or unsubstituted alkenyl group" is an "unsubstituted alkenyl group"; and the substituted alkenyl group indicates a case where the "substituted or unsubstituted alkenyl group" is a "substituted alkenyl group".) In this description, a mere expression of "an alkenyl group" includes both "an unsubstituted alkenyl group" and "a substituted alkenyl group".

The "substituted alkenyl group" means a group of "an unsubstituted alkenyl group" in which one or more hydrogen atoms are substituted with substituent(s). Specific examples of the "substituted alkenyl group" include groups of the "unsubstituted alkenyl group" (Group G4A of specific examples) having a substituent, and examples of the substituted alkyl group (Group G4B of specific examples). Examples of the "unsubstituted alkenyl group" and examples of the "substituted alkenyl group" listed herein are some mere examples, and the "substituted alkenyl group" referred to in this description further includes groups of the "substituted alkenyl group" of Group G4B of specific examples in which the hydrogen atom of the alkenyl group itself is further substituted with a substituent, and groups of the "substituted alkenyl group" of Group G4B of specific examples in which the hydrogen atom of the substituent of the alkenyl group is further substituted with a substituent.

Unsubstituted alkenyl groups (Group G4A of specific examples):
a vinyl group,
an allyl group,
a 1-butenyl group,
a 2-butenyl group, and
a 3-butenyl group.

Substituted alkenyl groups (Group G4B of specific examples):
a 1,3-butanedienyl group,
a 1-methylvinyl group,
a 1-methylallyl group,
a 1,1-dimethylallyl group,
a 2-methylallyl group, and
a 1,2-dimethylallyl group.

"Substituted or Unsubstituted Alkynyl Group"

Specific examples of the "substituted or unsubstituted alkynyl group" referred to in this description (Group G5 of specific examples) include the following unsubstituted alkynyl groups (Group G5A of specific examples). (Here, the unsubstituted alkynyl group indicates a case where the "substituted or unsubstituted alkynyl group" is an "unsubstituted alkynyl group".) Hereinunder, a mere expression of "an alkynyl group" includes both "an unsubstituted alkynyl group" and "a substituted alkynyl group".

The "substituted alkynyl group" means a group of "an unsubstituted alkynyl group" in which one or more hydrogen atoms are substituted with substituent(s). Specific examples of the "substituted alkynyl group" include groups of the "unsubstituted alkynyl group" (Group G5A of specific examples) in which one or more hydrogen atoms are substituted with substituent(s).

Unsubstituted alkynyl groups (Group G5A of specific examples):
an ethynyl group.

"Substituted or Unsubstituted Cycloalkyl Group"

Specific examples of the "substituted or unsubstituted cycloalkyl group" referred to in this description (Group G6 of specific examples) include the following unsubstituted cycloalkyl groups (Group G6A of specific examples) and the following substituted cycloalkyl groups (Group G6B of specific examples). (Here, the unsubstituted cycloalkyl group indicates a case where the "substituted or unsubstituted cycloalkyl group" is an "unsubstituted cycloalkyl group"; and the substituted cycloalkyl group indicates a case where the "substituted or unsubstituted cycloalkyl group" is a "substituted cycloalkyl group".) In this description, a mere expression of "a cycloalkyl group" includes both "an unsubstituted cycloalkyl group" and "a substituted cycloalkyl group".

The "substituted cycloalkyl group" means a group of "an unsubstituted cycloalkyl group" in which one or more hydrogen atoms are substituted with substituent(s). Specific examples of the "substituted cycloalkyl group" include groups of the "unsubstituted cycloalkyl group" (Group G6A of specific examples) in which one or more hydrogen atoms are substituted with substituent(s), and examples of the substituted cycloalkyl group (Group G6B of specific examples). Examples of the "unsubstituted cycloalkyl group" and examples of the "substituted cycloalkyl group" listed herein are some mere examples, and the "substituted cycloalkyl group" referred to in this description further includes groups of the "substituted cycloalkyl group" of Group G6B of specific examples in which one or more hydrogen atoms bonding to the carbon atoms of the cycloalkyl group itself are further substituted with substituent(s), and groups of the "substituted cycloalkyl group" of Group G6B of specific examples in which the hydrogen atom of the substituent of the cycloalkyl group is further substituted with a substituent.

Unsubstituted cycloalkyl groups (Group G6A of specific examples):
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted cycloalkyl groups (Group G6B of specific examples):
a 4-methylcyclohexyl group.

"Group represented by —Si($R_{901}$)($R_{902}$)($R_{903}$)"

Specific examples of the group represented by —Si($R_{901}$)($R_{902}$)($R_{903}$) as referred to in this description (Group G7 of specific examples) include the following:
—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6)

In these,
G1 is a "substituted or unsubstituted aryl group" of Group G1 of specific examples.
G2 is a "substituted or unsubstituted heterocyclic group" of Group G2 of specific examples.
G3 is a "substituted or unsubstituted alkyl group" of Group G3 of specific examples.
G6 is a "substituted or unsubstituted cycloalkyl group" of Group GG of specific examples.

Plural G1's in —Si(G1)(G1)(G1) are the same as or different from each other.
Plural G2's in —Si(G1)(G2)(G2) are the same as or different from each other.
Plural G1's in —Si(G1)(G1)(G2) are the same as or different from each other.

Plural G2's in —Si(G2)(G2)(G2) are the same as or different from each other.
Plural G3's in —Si(G3)(G3)(G3) are the same as or different from each other.
Plural G6's in —Si(G6)(G6)(G6) are the same as or different from each other.

"Group Represented by —O—($R_{904}$)"

Specific examples of the group represented by —O—($R_{904}$) referred to in this description (Group G8 of specific examples) include the following:
—O(G1),
—O(G2),
—O(G3), and
—O(G6).

In these,
G1 is a "substituted or unsubstituted aryl group" of Group G1 of specific examples.
G2 is a "substituted or unsubstituted heterocyclic group" of Group G2 of specific examples.
G3 is a "substituted or unsubstituted alkyl group" of Group G3 of specific examples.
G6 is a "substituted or unsubstituted cycloalkyl group" of Group G6 of specific examples.

"Group Represented by —S—($R_{905}$)"

Specific examples of the group represented by —S—($R_{905}$) referred to in this description (Group G9 of specific examples) include the following:
—S(G1),
—S(G2),
—S(G3), and
—S(G6).

In these,
G1 is a "substituted or unsubstituted aryl group" of Group G1 of specific examples.
G2 is a "substituted or unsubstituted heterocyclic group" of Group G2 of specific examples.
G3 is a "substituted or unsubstituted alkyl group" of Group G3 of specific examples.
G6 is a "substituted or unsubstituted cycloalkyl group" of Group G6 of specific examples.

"Group represented by —N($R_{906}$)($R_{907}$)"

Specific examples of the group represented by —N($R_{906}$)($R_{907}$) referred to in this description (Group G10 of specific examples) include the following:
—N(G1)(G1),
—N(G2)(G2),
—N(G1)(G2),
—N(G3)(G3), and
—N(G6)(G6).

In these,
G1 is a "substituted or unsubstituted aryl group" of Group G1 of specific examples.
G2 is a "substituted or unsubstituted heterocyclic group" of Group G2 of specific examples.
G3 is a "substituted or unsubstituted alkyl group" of Group G3 of specific examples.
G6 is a "substituted or unsubstituted cycloalkyl group" of Group G6 of specific examples.

Plural G1's in N(G1)(G1) are the same as or different from each other.
Plural G2's in N(G2)(G2) are the same as or different from each other.
Plural G3's in N(G3)(G3) are the same as or different from each other.
Plural G6's in N(G6)(G6) are the same as or different from each other.

"Halogen Atom"

Specific examples of "a halogen atom" referred to in this description (Group G11 of specific examples) include a fluorine atom, a chlorine atom, a bromine atom and an iodine atom.

"Substituted or Unsubstituted Fluoroalkyl Group"

The "substituted or unsubstituted fluoroalkyl group" referred to in this description means a group of "a substituted or unsubstituted alkyl group" in which at least one hydrogen atom bonding to the carbon atom that constitutes the alkyl group is substituted with a fluorine atom, and includes a group of "a substituted or unsubstituted alkyl group" in which all the hydrogen atoms bonding to the carbon atoms that constitute the alkyl group are substituted with fluorine atoms (perfluoro group). The carbon number of the "unsubstituted fluoroalkyl group" is, unless otherwise specifically noted in this description, 1 to 50, preferably 1 to 30, more preferably 1 to 18. The "substituted fluoroalkyl group" means a "fluoroalkyl group" in which one or more hydrogen atoms are substituted with substituent(s). The "substituted fluoroalkyl group" referred to in this description also includes a "substituted fluoroalkyl group" in which one or more hydrogen atoms bonding to the carbon atom of the alkyl chain therein are further substituted with substituent(s), and a "substituted fluoroalkyl group" in which one or more hydrogen atoms of the substituent are further substituted with a substituent. Specific examples of the "unsubstituted fluoroalkyl group" include examples of the above-mentioned "alkyl group" (Group G3 of specific examples) in which one or more hydrogen atoms are substituted with fluorine atom(s).

"Substituted or Unsubstituted Haloalkyl Group"

The "substituted or unsubstituted haloalkyl group" referred to in this description means a group of "a substituted or unsubstituted alkyl group" in which at least one hydrogen atom bonding to the carbon atom that constitutes the alkyl group is substituted with a halogen atom, and includes a group of "a substituted or unsubstituted alkyl group" in which all the hydrogen atoms bonding to the carbon atoms that constitute the alkyl group are substituted with halogen atoms. The carbon number of the "unsubstituted haloalkyl group" is, unless otherwise specifically noted in this description, 1 to 50, preferably 1 to 30, more preferably 1 to 18. The "substituted haloalkyl group" means a "haloalkyl group" in which one or more hydrogen atoms are substituted with substituent(s). The "substituted haloalkyl group" referred to in this description also includes a "substituted haloalkyl group" in which one or more hydrogen atoms bonding to the carbon atom of the alkyl chain therein are further substituted with substituent(s), and a "substituted haloalkyl group" in which one or more hydrogen atoms of the substituent are further substituted with a substituent. Specific examples of the "unsubstituted haloalkyl group" include examples of the above-mentioned "alkyl group" (Group G3 of specific examples) in which one or more hydrogen atoms are substituted with halogen atom(s). The haloalkyl group may also be referred to as a halogenoalkyl group.

"Substituted or Unsubstituted Alkoxy Group"

Specific examples of the "substituted or unsubstituted alkoxy group" referred to in this description include groups represented by —O(G3), in which G3 is a "substituted or unsubstituted alkyl group" of Group G3 of specific examples. The carbon number of the "unsubstituted alkoxy group" is, unless otherwise specifically noted in this description, 1 to 50, preferably 1 to 30, more preferably 1 to 18.

"Substituted or Unsubstituted Alkylthio Group"

Specific examples of the "substituted or unsubstituted alkylthio group" referred to in this description include groups represented by —S(G3), in which G3 is a "substituted or unsubstituted alkyl group" of Group G3 of specific examples. The carbon number of the "unsubstituted alkylthio group" is, unless otherwise specifically noted in this description, 1 to 50, preferably 1 to 30, more preferably 1 to 18.

"Substituted or Unsubstituted Aryloxy Group"

Specific examples of the "substituted or unsubstituted aryloxy group" referred to in this description include groups represented by —O(G1), in which G1 is a "substituted or unsubstituted aryl group" of Group G1 of specific examples. The ring carbon number of the "unsubstituted aryloxy group" is, unless otherwise specifically noted in this description, 6 to 50, preferably 6 to 30, more preferably 6 to 18.

"Substituted or Unsubstituted Arylthio Group"

Specific examples of the "substituted or unsubstituted arylthio group" referred to in this description include groups represented by —S(G1), in which G1 is a "substituted or unsubstituted aryl group" of Group G1 of specific examples. The ring carbon number of the "unsubstituted arylthio group" is, unless otherwise specifically noted in this description, 6 to 50, preferably 6 to 30, more preferably 6 to 18.

"Substituted or Unsubstituted Trialkylsilyl Group"

Specific examples of the "trialkylsilyl group" referred to in this description include groups represented by —Si(G3)(G3)(G3), in which G3 is a "substituted or unsubstituted alkyl group" of Group G3 of specific examples. Plural G3's in —Si(G3)(G3)(G3) are the same as or different from each other. The carbon number of each alkyl group of the "trialkylsilyl group" is, unless otherwise specifically noted in this description, 1 to 50, preferably 1 to 20, more preferably 1 to 6.

"Substituted or Unsubstituted Aralkyl Group"

Specific examples of the "substituted or unsubstituted aralkyl group" referred to in this description include groups represented by -(G3)-(G1), in which G3 is a "substituted or unsubstituted alkyl group" of Group G3 of specific examples, and G1 is a "substituted or unsubstituted aryl group" of Group G1 of specific examples. Accordingly, the "aralkyl group" is a group of an "alkyl group" in which the hydrogen atom is substituted with a substituent "aryl group", and is one embodiment of a "substituted alkyl group". The "unsubstituted aralkyl group" is an "unsubstituted alkyl group" substituted with an "unsubstituted aryl group, and the carbon number of the "unsubstituted aralkyl group" is, unless otherwise specifically noted in this description, 7 to 50, preferably 7 to 30, more preferably 7 to 18.

Specific examples of the "substituted or unsubstituted aralkyl group" include a benzyl group, a 1-phenylethyl group, a 2-phenylethyl group, a 1-phenyl-isopropyl group, a 2-phenyl-isopropyl group, a phenyl-t-butyl group, an α-naphthylmethyl group, a 1-α-naphthylethyl group, a 2-α-naphthylethyl group, a 1-α-naphthyl-isopropyl group, a 2-α-naphthyl-isopropyl group, a β-naphthylmethyl group, a 1-β-naphthylethyl group, a 2-β-naphthylethyl group, a 1-β-naphthyl-isopropyl group and a 2-β-naphthyl-isopropyl group.

Preferred examples of the substituted or unsubstituted aryl group referred to in this description include, unless otherwise specifically indicated in this description, a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an p-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, and a 9,9-diphenylfluorenyl group.

Preferred examples of the substituted or unsubstituted heterocyclic group referred to in this description include, unless otherwise specifically indicated in this description, a pyridyl group, a pyrimidinyl group, a triazinyl group, a quinolyl group, an isoquinolyl group, a quinazolyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, and a phenyldibenzothiophenyl group.

In this description, the carbazolyl group is, unless otherwise specifically indicated in this description, a group of any of the following:

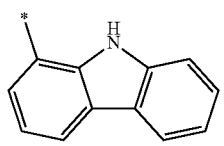
(TEMP-Cz1)

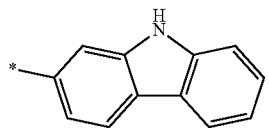
(TEMP-Cz2)

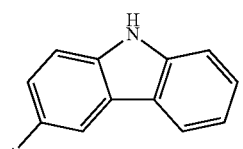
(TEMP-Cz3)

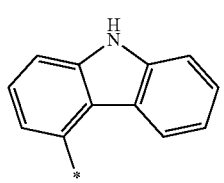
(TEMP-Cz4)

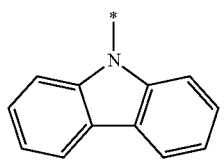
(TEMP-Cz5)

In this description, the (9-phenyl)carbazolyl group is, unless otherwise specifically indicated in this description, a group of any of the following:

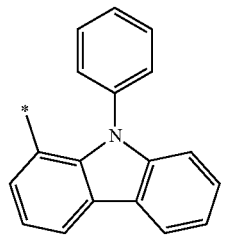
(TEMP-Cz6)

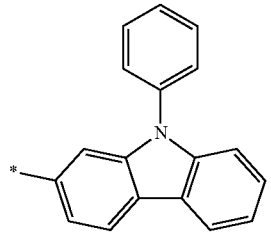
(TEMP-Cz7)

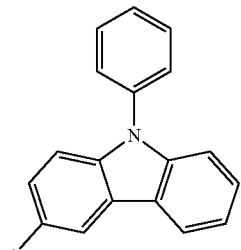
(TEMP-Cz8)

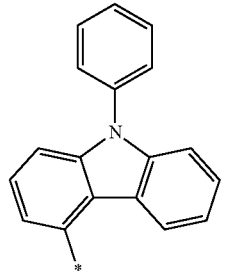
(TEMP-Cz9)

In the general formulae (TEMP-Cz1) to (TEMP-Cz9), * indicates a bonding position.

In this description, the dibenzofuranyl group and the dibenzothiophenyl group are, unless otherwise specifically indicated in this description, groups of any of the following:

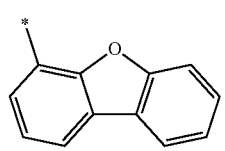
(TEMP-34)

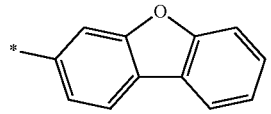
(TEMP-35)

-continued

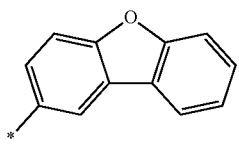
(TEMP-36)

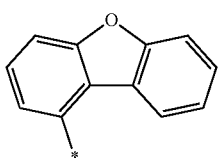
(TEMP-37)

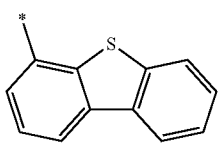
(TEMP-38)

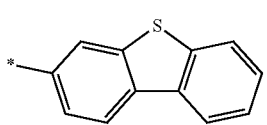
(TEMP-39)

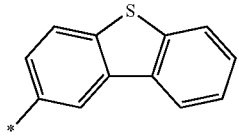
(TEMP-40)

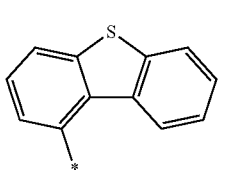
(TEMP-41)

In the general formulae (TEMP-34) to (TEMP-41), * indicates a bonding position.

Preferred examples of the substituted or unsubstituted alkyl group referred to in this description include, unless otherwise specifically indicated in this description, a methyl group, an ethyl group, a propyl group, an isopropyl group, an n-butyl group, an isobutyl group, and a t-butyl group.

"Substituted or Unsubstituted Arylene Group"

The "substituted or unsubstituted arylene group" referred to in this description is, unless otherwise specifically indicated, a divalent group derived from the above-mentioned "substituted or unsubstituted aryl group" by removing one hydrogen atom from the aryl ring therein. Specific examples of the "substituted or unsubstituted arylene group" (Group G12 of specific examples) include a divalent group derived from the "substituted or unsubstituted aryl group" of Group G1 of specific examples by removing one hydrogen atom from the aryl ring therein.

"Substituted or Unsubstituted Divalent Heterocyclic Group"

The "substituted or unsubstituted divalent heterocyclic group" referred to in this description is, unless otherwise specifically indicated, a divalent group derived from the above-mentioned "substituted or unsubstituted heterocyclic group" by removing one hydrogen atom from the hetero ring therein. Specific examples of the "substituted or unsubstituted divalent heterocyclic group" (Group G13 of specific examples) include a divalent group derived from the "substituted or unsubstituted heterocyclic group" of Group G2 of specific examples by removing one hydrogen atom from the hetero ring therein.

"Substituted or Unsubstituted Alkylene Group"

The "substituted or unsubstituted alkylene group" referred to in this description is, unless otherwise specifically indicated, a divalent group derived from the above-mentioned "substituted or unsubstituted alkyl group" by removing one hydrogen atom from the alkyl chain therein. Specific examples of the "substituted or unsubstituted alkylene group" (Group G14 of specific examples) include a divalent group derived from the "substituted or unsubstituted alkyl group" of Group G3 of specific examples by removing one hydrogen atom from the alkyl chain therein.

The substituted or unsubstituted arylene group referred to in this description is, unless otherwise specifically noted in this description, preferably a group of any of the following general formulae (TEMP-42) to (TEMP-67).

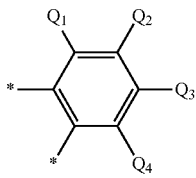
(TEMP-42)

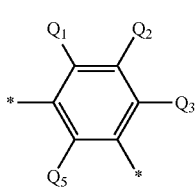
(TEMP-43)

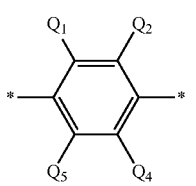
(TEMP-44)

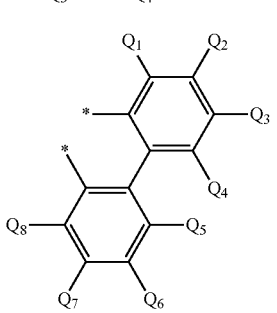
(TEMP-45)

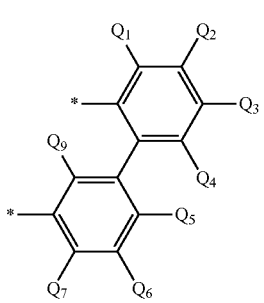
(TEMP-46)

(TEMP-47)
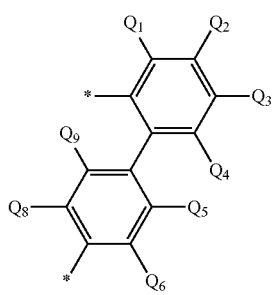
(TEMP-48)
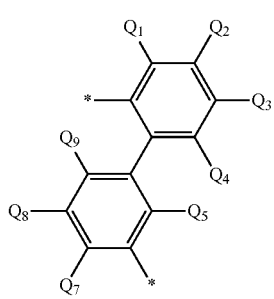
(TEMP-49)
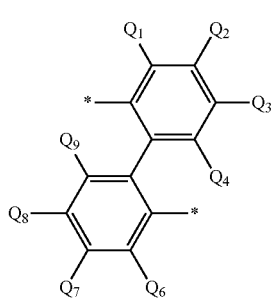
(TEMP-50)
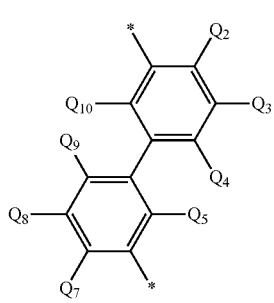
(TEMP-51)
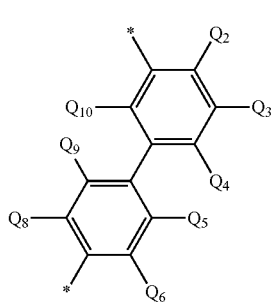
(TEMP-52)
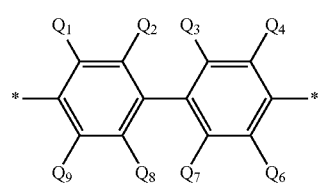
In the general formulae (TEMP-42) to (TEMP-52), $Q_1$ to $Q_{10}$ each independently represent a hydrogen atom or a substituent.
In the general formulae (TEMP-42) to (TEMP-52), * indicates a bonding position.
(TEMP-53)
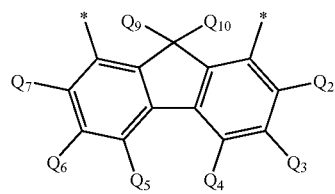
(TEMP-54)
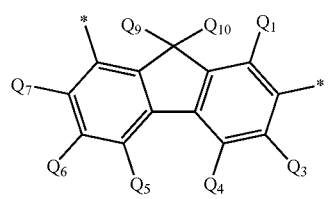
(TEMP-55)
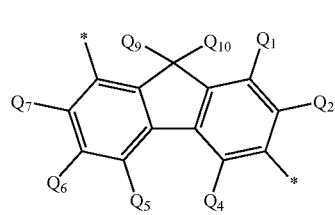
(TEMP-56)
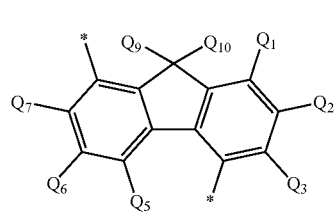
(TEMP-57)
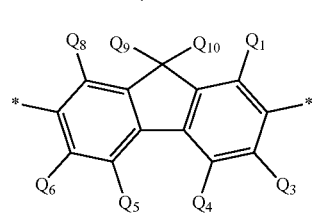
(TEMP-58)
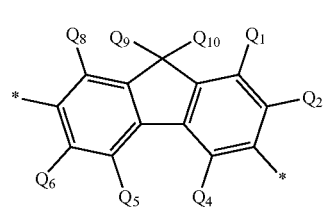

(TEMP-59)
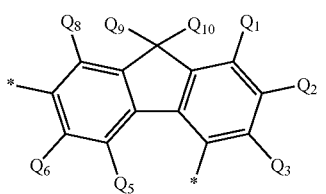

(TEMP-60)
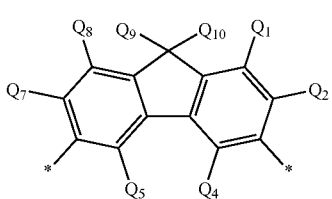

(TEMP-61)
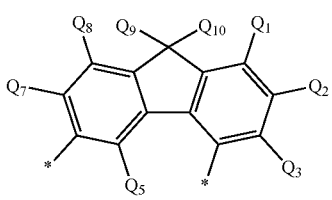

(TEMP-62)
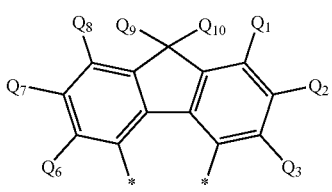

In the general formulae (TEMP-53) to (TEMP-62), $Q_1$ to $Q_{10}$ each independently represent a hydrogen atom or a substituent.

$Q_9$ and $Q_{10}$ may bond to each other via a single bond to form a ring.

In the general formulae (TEMP-53) to (TEMP-62), * indicates a bonding position.

(TEMP-63)
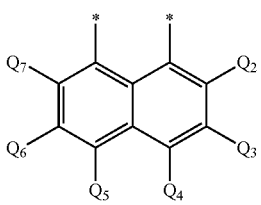

(TEMP-64)
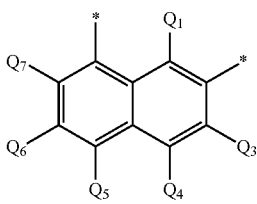

(TEMP-65)
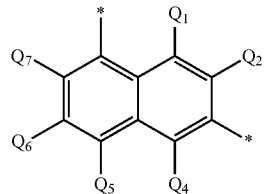

(TEMP-66)
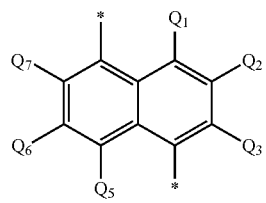

(TEMP-67)
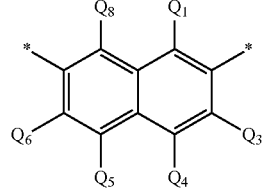

(TEMP-68)
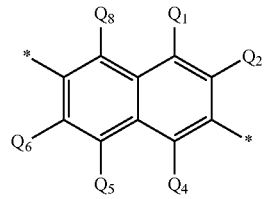

In the general formulae (TEMP-63) to (TEMP-68), $Q_1$ to $Q_8$ each independently represent a hydrogen atom or a substituent.

In the general formulae (TEMP-63) to (TEMP-68), * indicates a bonding position.

Preferably, the substituted or unsubstituted divalent heterocyclic group referred to in this description is, unless otherwise specifically noted in this description, a group of any of the following general formulae (TEMP-69) to (TEMP-102).

(TEMP-69)
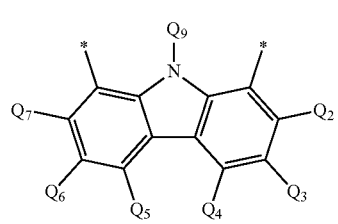

(TEMP-70)
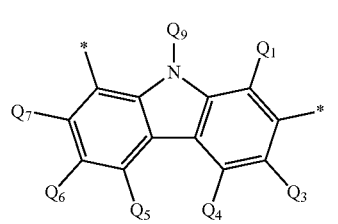

(TEMP-71)
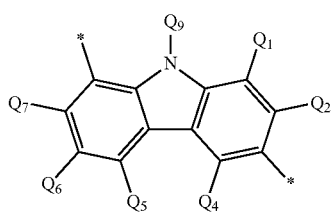
(TEMP-72)
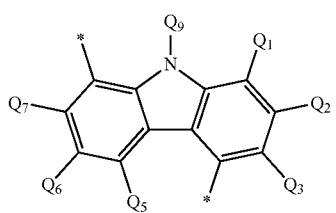
(TEMP-73)
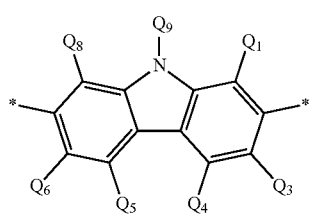
(TEMP-74)
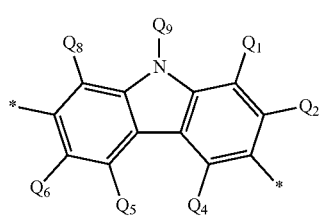
(TEMP-75)
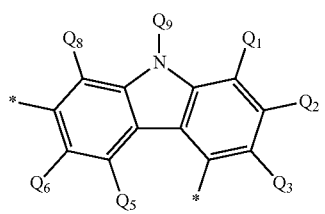
(TEMP-76)
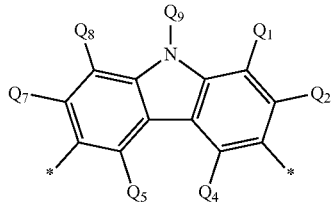
(TEMP-77)
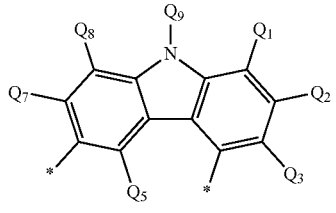
(TEMP-78)
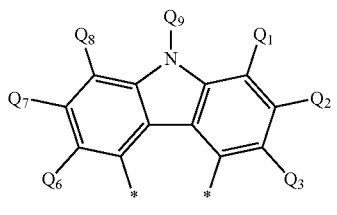
(TEMP-79)
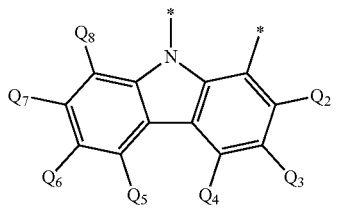
(TEMP-80)
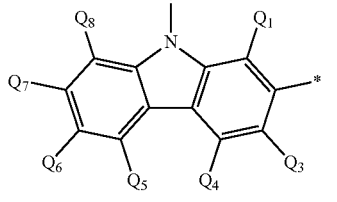
(TEMP-81)
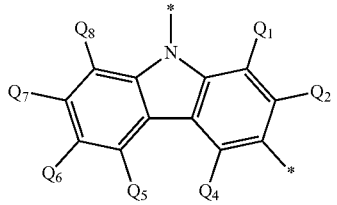
(TEMP-82)
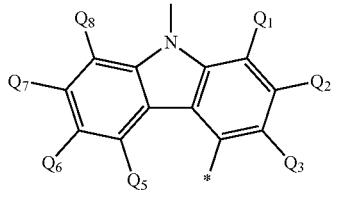
In the general formulae (TEMP-69) to (TEMP-82), $Q_1$ to $Q_9$ each independently represent a hydrogen atom or a substituent.
(TEMP-83)
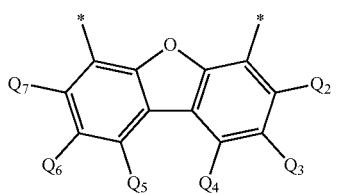
(TEMP-84)
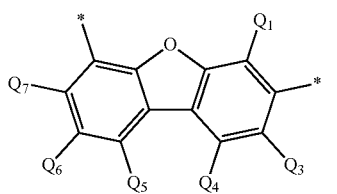

(TEMP-85)
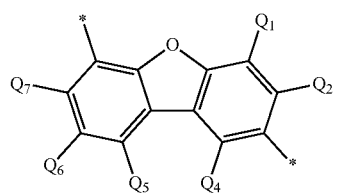
(TEMP-86)
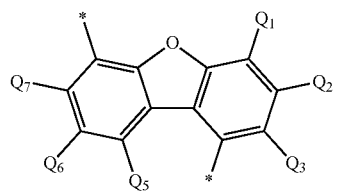
(TEMP-87)
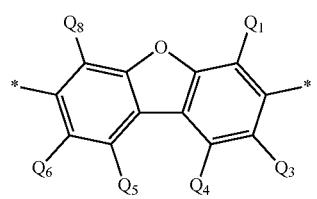
(TEMP-88)
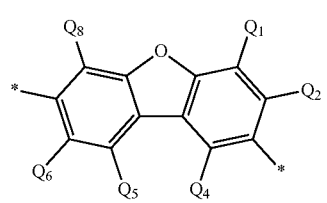
(TEMP-89)
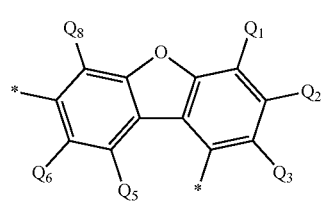
(TEMP-90)
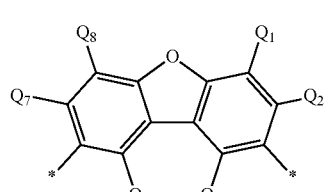
(TEMP-91)
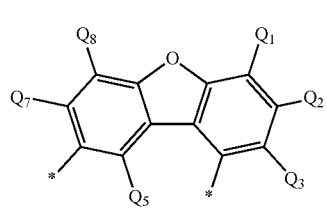
(TEMP-92)
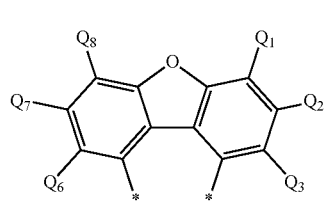
(TEMP-93)
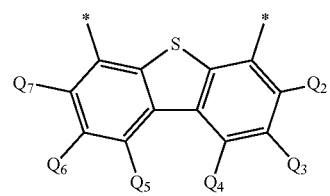
(TEMP-94)
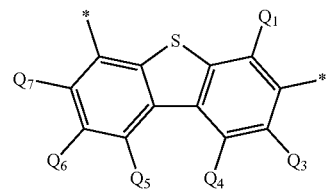
(TEMP-95)
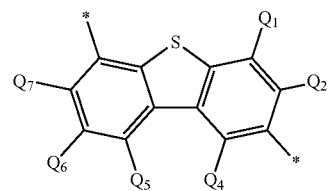
(TEMP-96)
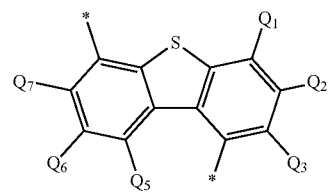
(TEMP-97)
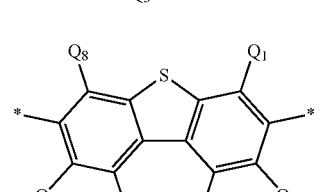
(TEMP-98)
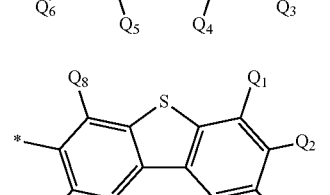
(TEMP-99)
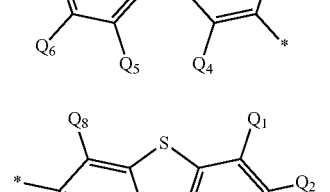
(TEMP-100)
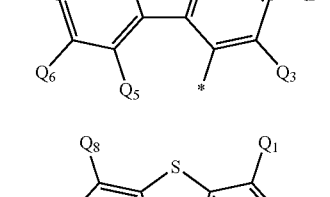
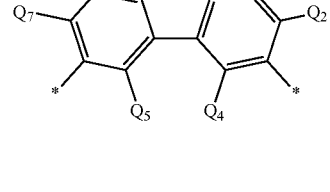

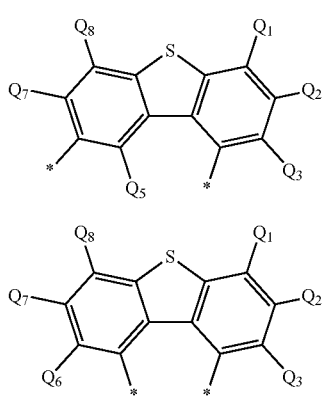

(TEMP-101)

(TEMP-102)

In the general formulae (TEMP-83) to (TEMP-102), $Q_1$ to $Q_8$ each independently represent a hydrogen atom or a substituent.

The above is a description of the "substituents referred to in this description".

"Case of Bonding to Form Ring"

In this description, a case where "one pair or more of combinations formed of neighboring two or more bond to each other to form a substituted or unsubstituted single ring, or bond to each other to form a substituted or unsubstituted condensed ring, or do not bond to each other" means a case where "one pair or more of combinations formed of neighboring two or more bond to each other to form a substituted or unsubstituted single ring", a case where "one pair or more of combinations formed of neighboring two or more bond to each other to form a substituted or unsubstituted condensed ring", and a case where "one pair or more of combinations formed of neighboring two or more do not bond to each other".

As referred to in this description, the case where "one pair or more of combinations formed of neighboring two or more bond to each other to form a substituted or unsubstituted single ring", and the case where "one pair or more of combinations formed of neighboring two or more bond to each other to form a substituted or unsubstituted condensed ring" (hereinafter these cases may be collectively referred to as "a case of bonding to form a ring") are described. A case of an anthracene compound having an anthracene ring as a mother skeleton, as represented by the following general formula (TEMP-103) is described as one example.

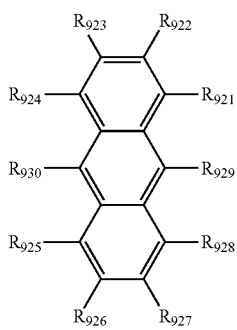

(TEMP-103)

For example, in the case where "one pair or more of combinations formed of neighboring two or more bond to each other to form a ring" among $R_{921}$ to $R_{930}$, the neighboring two to form one pair includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The above-mentioned expression "one pair or more" means that two or more pairs of combinations formed of neighboring two or more may form a ring at the same time. For example, in the case where $R_{921}$ and $R_{922}$ bond to each other to form a ring $Q_A$ and at the same time where $R_{925}$ and $R_{926}$ bond to each other to form a ring $Q_B$, the anthracene compound represented by the general formula (TEMP-103) is represented by the following general formula (TEMP-104).

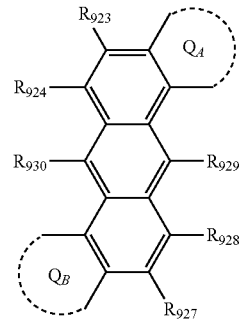

(TEMP-104)

The case where "a combination of neighboring two or more" forms a ring includes not only the case where the neighboring "two" bond like the above-mentioned case, but also a case where neighboring "three or more" bond. Examples of the case include a case where $R_{921}$ and $R_{922}$ bond to each other to form a ring $Q_A$, and $R_{922}$ and $R_{923}$ bond to each other to form a ring $Q_C$, and further the neighboring three ($R_{921}$, $R_{922}$ and $R_{923}$) bond to each other to form a ring to be condensed with the anthracene mother skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

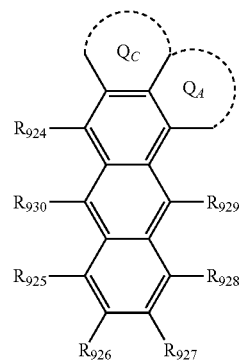

(TEMP-105)

The formed "single ring" or "condensed ring" may be a saturated ring or an unsaturated ring as a structure of the formed ring alone. Also in the case where "one pair of neighboring two" form "a single ring" or "a condensed ring", the "single ring" or the "condensed ring" may form a saturated ring or an unsaturated ring. For example, the ring $Q_A$ and the ring $Q_B$ formed in the general formula (TEMP-104) each are a "single ring" or a "condensed ring". The ring $Q_A$ and the ring $Q_C$ formed in the general formula (TEMP-105) each are a "condensed ring". In the general formula (TEMP-105), the $Q_A$ and the $Q_C$ are condensed to form a condensed ring. When the ring $Q_A$ in the general formula (TEMP-104) is a benzene ring, the ring $Q_A$ is a single ring. When the ring $Q_A$ in the general formula (TEMP-104) is a naphthalene ring, the ring $Q_A$ is a condensed ring.

The "unsaturated ring" means an aromatic hydrocarbon ring or an aromatic hetero ring. The "saturated ring" means an aliphatic hydrocarbon ring or a nonaromatic hetero ring.

Specific examples of the aromatic hydrocarbon ring include structures formed by terminating the groups listed as specific examples in Group G1 of specific examples with a hydrogen atom.

Specific examples of the aromatic hetero ring include structures formed by terminating the groups listed as specific examples in Group G2 of specific examples with a hydrogen atom.

Specific examples of the aliphatic hydrocarbon ring include structures formed by terminating the groups listed as specific examples in Group G6 of specific examples with a hydrogen atom.

"To form a ring" means that plural atoms alone of the mother skeleton, or plural atoms of the mother skeleton and any other one or more elements form a ring. For example, in the general formula (TEMP-104), the ring $Q_A$ formed by $R_{921}$ and $R_{922}$ bonding to each other means a ring formed of the carbon atom of the anthracene skeleton to which $R_{921}$ bonds, the carbon atom of the anthracene skeleton to which $R_{922}$ bonds, and one or more other elements. One example is described. In the case where $R_{921}$ and $R_{922}$ form the ring $Q_A$, the carbon atom of the anthracene skeleton to which $R_{991}$ bonds, the carbon atom of the anthracene skeleton to which $R_{922}$ bonds, and four carbon atoms form a monocyclic unsaturated ring, the ring formed of $R_{921}$ and $R_{922}$ is a benzene ring.

Here, "any other element" is, unless otherwise specifically noted in this description, preferably at least one element selected from the group consisting of a carbon element, a nitrogen element, an oxygen element, and a sulfur element. In the case where the other element (for example, a carbon element or a nitrogen element) does not form a ring, the structure may be terminated with a hydrogen atom, or may be substituted with "an arbitrary substituent" to be mentioned hereinunder. In the case of containing any other element than a carbon element, the ring to be formed is a hetero ring.

The number of "one or more other elements" constituting a single ring or a condensed ring is, unless otherwise specifically noted in this description, preferably 2 or more and 15 or less, more preferably 3 or more and 12 or less, even more preferably 3 or more and 5 or less.

Unless otherwise specifically noted in this description, among the "single ring" and the "condensed ring", the "single ring" is preferred.

Unless otherwise specifically noted in this description, among the "saturated ring" and the "unsaturated ring", the "unsaturated ring" is preferred.

Unless otherwise specifically noted in this description, the "single ring" is preferably a benzene ring.

Unless otherwise specifically noted in this description, the "unsaturated ring" is preferably a benzene ring.

In the case where "one pair or more of combinations formed of neighboring two or more" "bond to each other to form a substituted or unsubstituted single ring", or "bond to each other to form a substituted or unsubstituted condensed ring", unless otherwise specifically noted in this description, preferably, one pair or more of combinations formed of neighboring two or more bond to each other to form a substituted or unsubstituted "unsaturated ring" composed of plural atoms of the mother skeleton, and 1 or more and 15 or less, at least one element selected from a group consisting of a carbon element, a nitrogen element, an oxygen element and a sulfur element.

In the case where the "single ring" or the "condensed ring" has a substituent, the substituent may be "any arbitrary substituent" to be mentioned below. Specific examples of the substituent in the case where the "single ring" or the "condensed ring" has a substituent include the substituents referred to in the section of "substituents referred to in this description" given hereinabove.

In the case where the "saturated ring" or the "unsaturated ring" has a substituent, the substituent may be "any arbitrary substituent" to be mentioned below. Specific examples of the substituent in the case where the "single ring" or the "condensed ring" has a substituent include the substituents referred to in the section of "substituents referred to in this description" given hereinabove.

The above is a description of a case "where one pair or more of combinations formed of neighboring two or more bond to each other to form a substituted or unsubstituted single ring", and a case "where one pair or more of combinations formed of neighboring two or more bond to each other to form a substituted or unsubstituted condensed ring" ("a case of bonding to form a ring").

Substituent in a Case of "Substituted or Unsubstituted"

In one embodiment of this description, examples of the substituent in a case of the above-mentioned "substituted or unsubstituted" (in this description, this may be referred to as "any arbitrary substituent") include groups selected from the group consisting of:

an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group having 6 to 50 ring carbon atoms, and
an unsubstituted heterocyclic group having 5 to 50 ring atoms.

In the above, $R_{901}$ to $R_{907}$ each independently represent:
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted heterocyclic group having 5 to 50 ring toms.

In the case of having two or more $R_{901}$'s, the two or more $R_{901}$'s are the same as or different from each other,
in the case of having two or more $R_{902}$'S, the two or more $R_{902}$'S are the same as or different from each other,
in the case of having two or more $R_{903}$'s, the two or more $R_{903}$'s are the same as or different from each other, in the case of having two or more $R_{904}$'s, the two or more $R_{904}$'s are the same as or different from each other, in the case of having two or more $R_{905}$'s, the two or more $R_{905}$'s are the same as or different from each other, in the case of having two or more $R_{906}$'s, the two or more $R_{906}$'s are the same as or different from each other, in the case of having two or more $R_{907}$'s, the two or more $R_{907}$'s are the same as or different from each other.

In one embodiment, the substituent in the case of "substituted or unsubstituted" is a group selected from the group consisting of:
an alkyl group having 1 to 50 carbon atoms,
an aryl group having 6 to 50 ring carbon atoms, and
a heterocyclic group having 5 to 50 ring atoms.

In one embodiment, the substituent in the case of "substituted or unsubstituted" is a group selected from the group consisting of an alkyl group having 1 to 18 carbon atoms, an aryl group having 6 to 18 ring carbon atoms, and a heterocyclic group having 5 to 18 ring atoms.

Specific examples of the group of the above-mentioned arbitrary substituent are the specific examples of the substituent described in the section of "substituents referred to in this description" given hereinabove.

Unless otherwise specifically indicated in this description, arbitrary neighboring substituents together may form "a saturated ring" or "an unsaturated ring", and preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring.

Unless otherwise specifically indicated in this description, arbitrary substituents may further have a substituent. The substituents that arbitrary substituents may further have are the same as the arbitrary substituents mentioned above.

In this description, the numeral range expressed as "to" means a range that includes the numeral value before "to" as the lower limit and the numeral value after "to" as the upper limit.

The compound of the present invention is described below.

The compound of the present invention is represented by the following formula (1). The compound of the present invention, as expressed by the formula (1) and as expressed by formulae belonging to the subordinate to the formula (1) may be simply referred to as "the inventive compound".

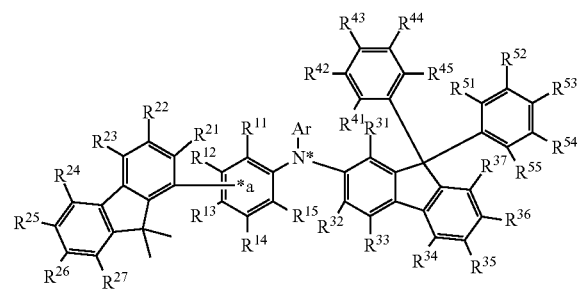

(1)

The formula (1) is expressed by any of the following formulae (5) to (7).

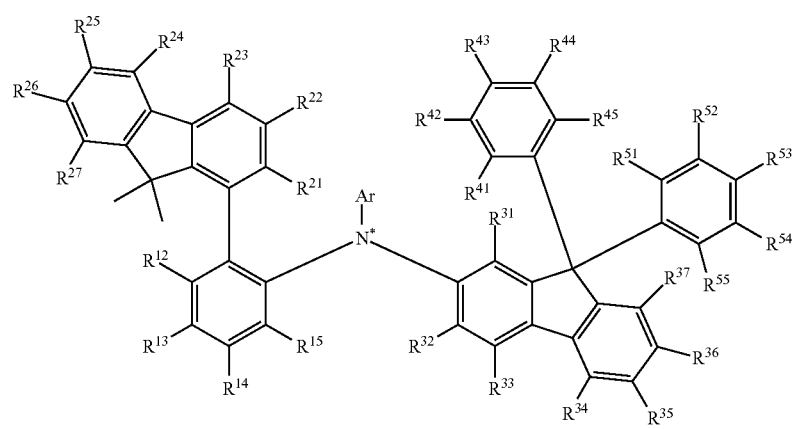

(5)

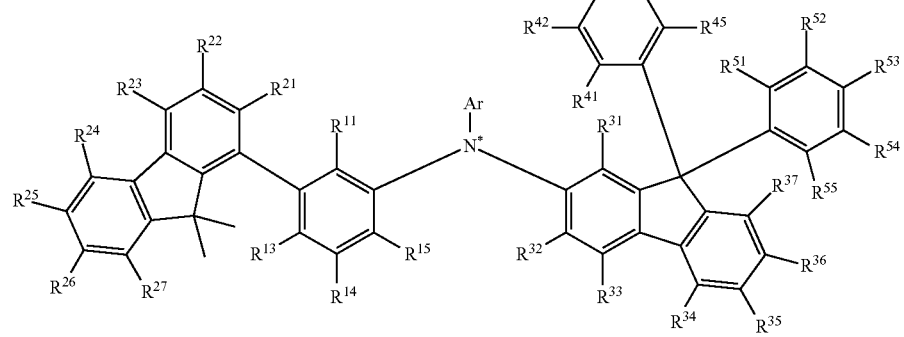

(6)

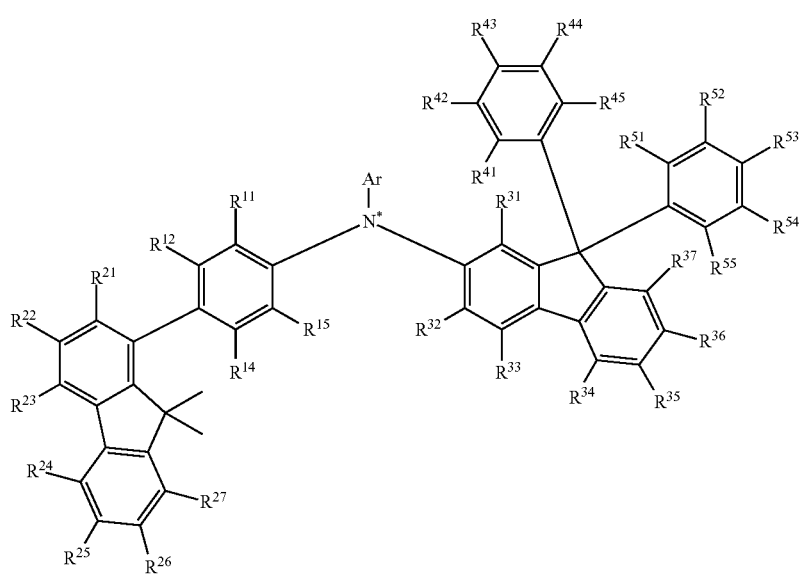
(7)
Hereinunder the symbols in the above formulae and in the formulae to be mentioned below are described.
N* represents a center nitrogen atom.
Ar is a group represented by any of the following formulae (2) to (4).
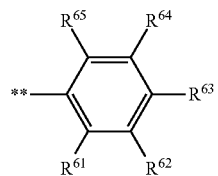
(2)
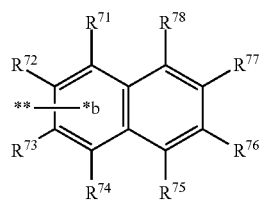
(3)
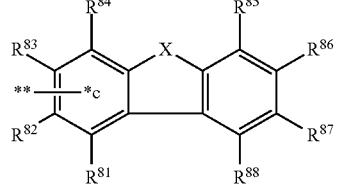
(4)
Accordingly, the inventive compound includes compounds represented by any of the following formulae (8) to (16).
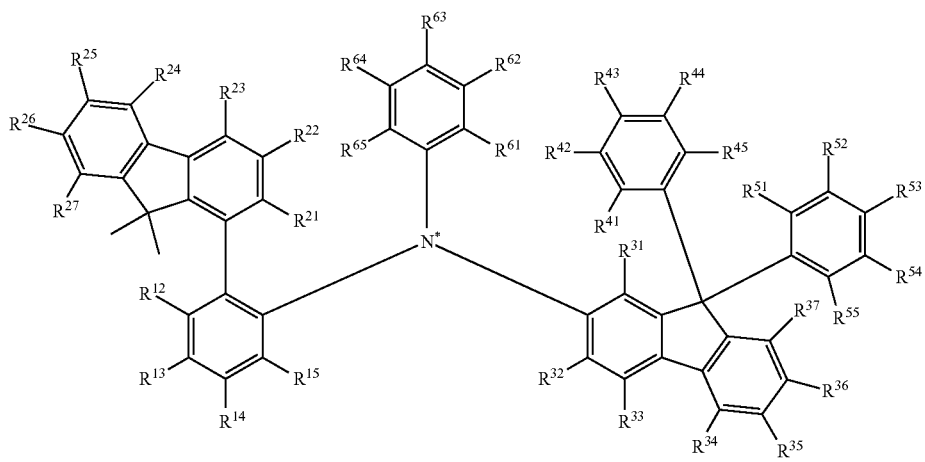
(8)

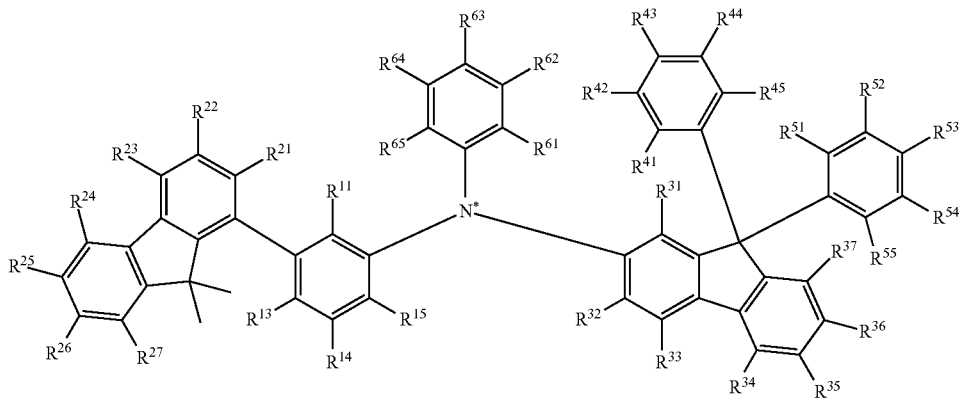
(9)
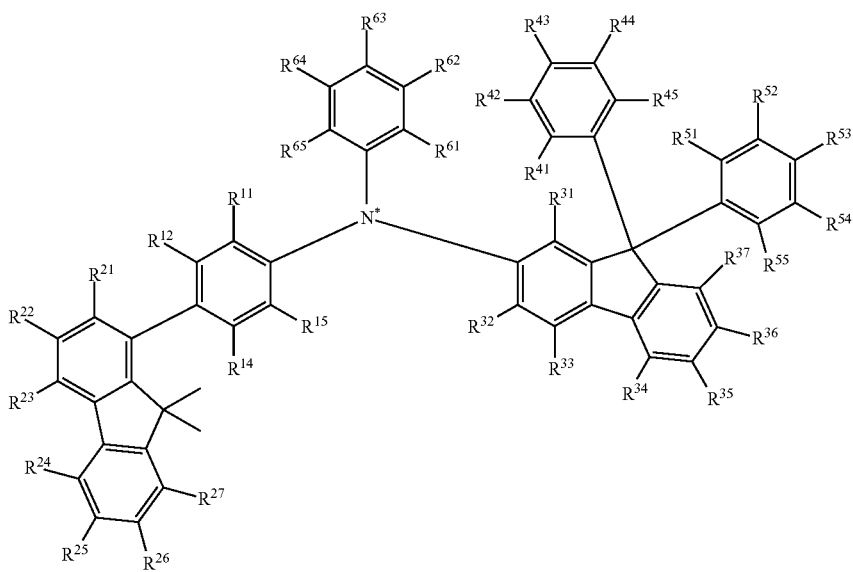
(10)
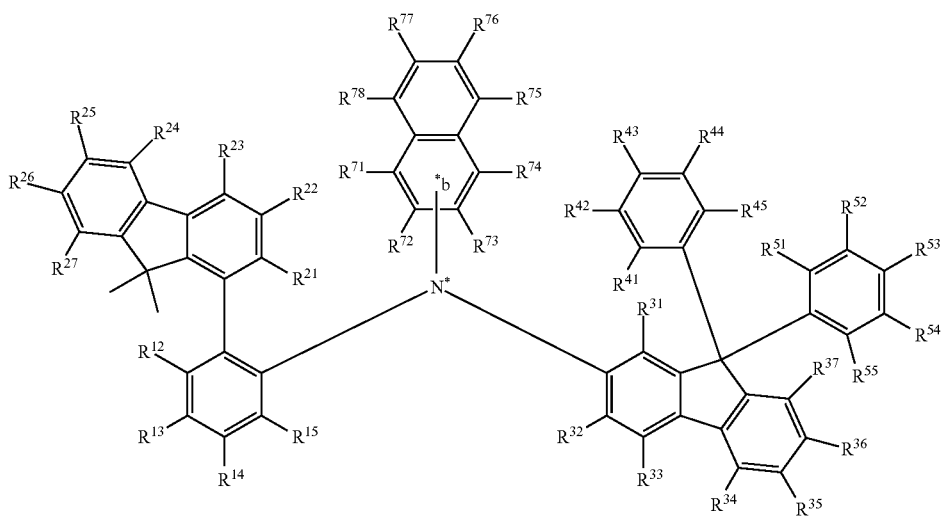
(11)

-continued
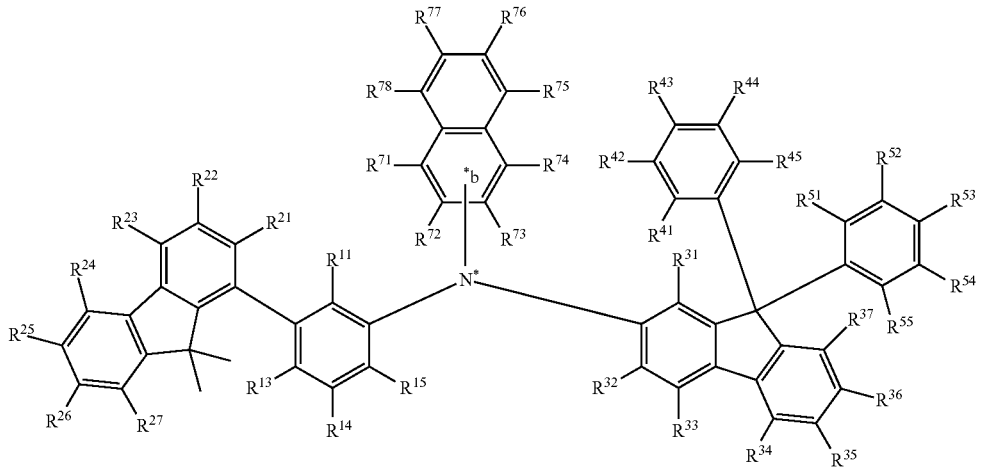
(12)
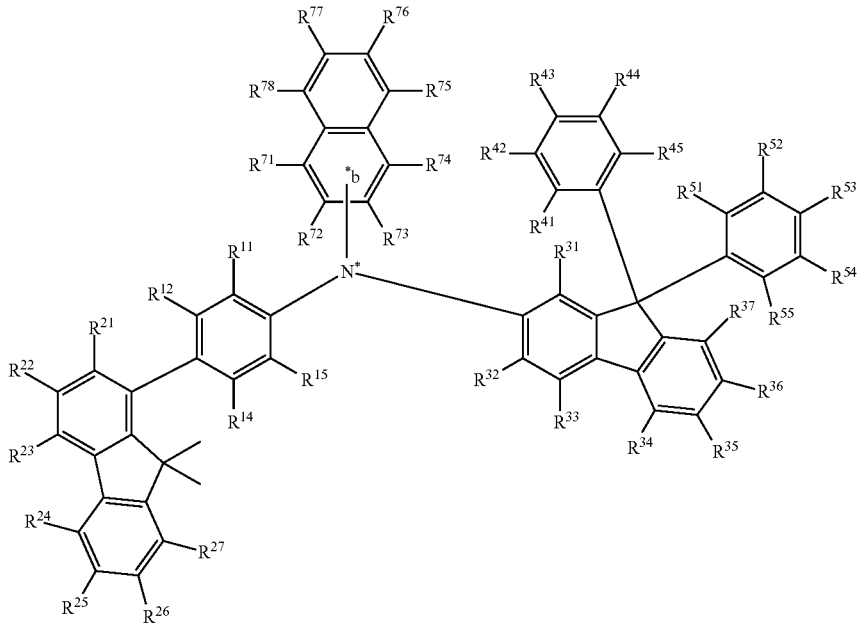
(13)

(14)
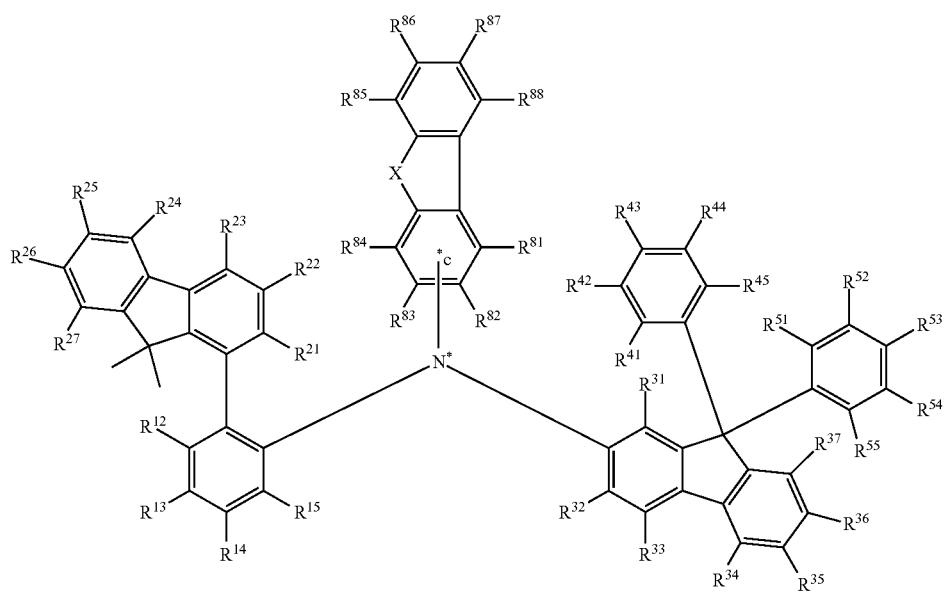
(15)
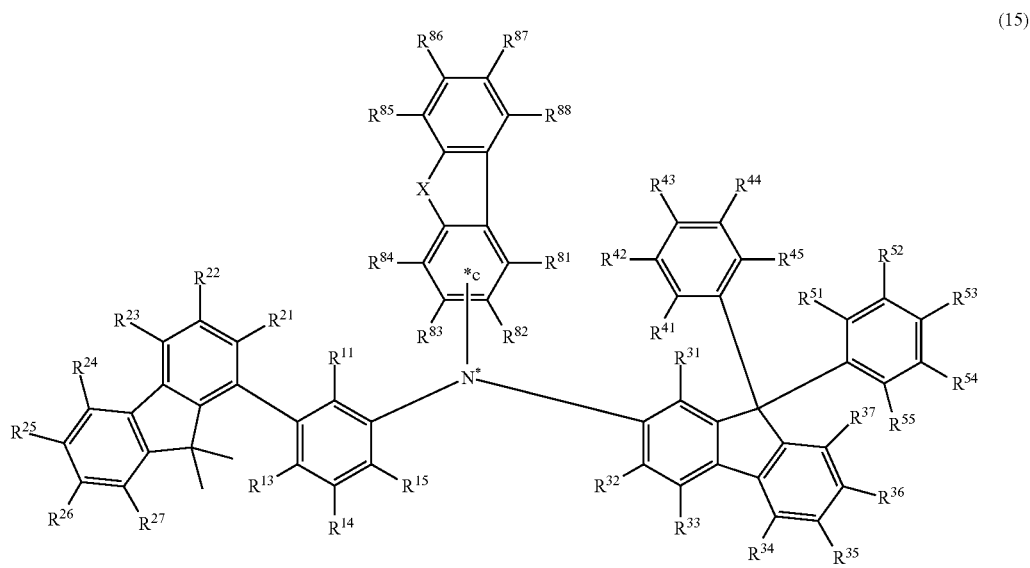

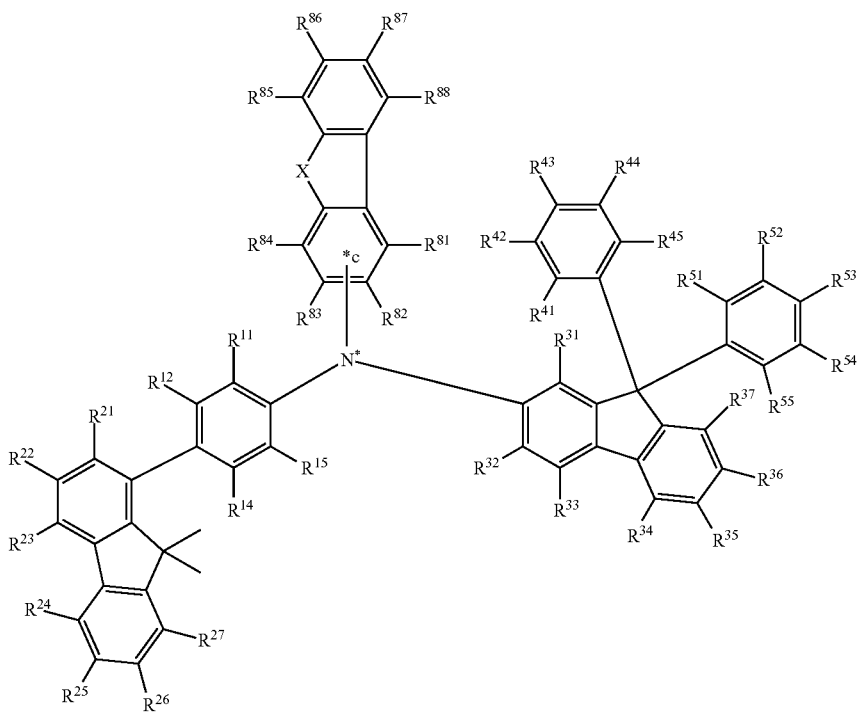

(16)

X represents an oxygen atom or a sulfur atom.

In one embodiment of the present invention, X is preferably an oxygen atom. In another embodiment of the present invention, X is preferably a sulfur atom.

$R^{61}$ to $R^{65}$, $R^{71}$ to $R^{78}$, and $R^{81}$ to $R^{88}$ each are independently selected from a hydrogen atom, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group and a cyano group;

preferably each independently represent a hydrogen atom, a substituted or unsubstituted alkyl group having 1 to 50 carbon atoms, a substituted or unsubstituted cycloalkyl group having 3 to 50 ring carbon atoms, or a cyano group;

more preferably each independently represent a hydrogen atom or a substituted or unsubstituted alkyl group having 1 to 50 carbon atoms.

One selected from $R^{71}$ to $R^{78}$ is a single bond bonding to *b, and one selected from $R^{81}$ to $R^{88}$ is a single bond bonding to *c. ** indicates a bonding position to the center nitrogen atom N*.

The formula (3) is represented by the following formula (3a) or (3b), preferably the following formula (3a).

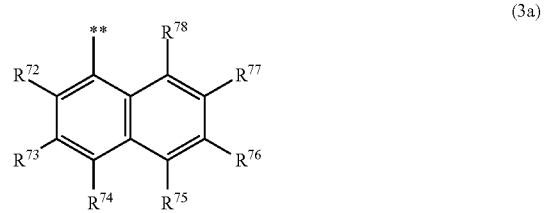

The formula (4) is represented by any of the following formulae (4a) to (4d).

(4a)

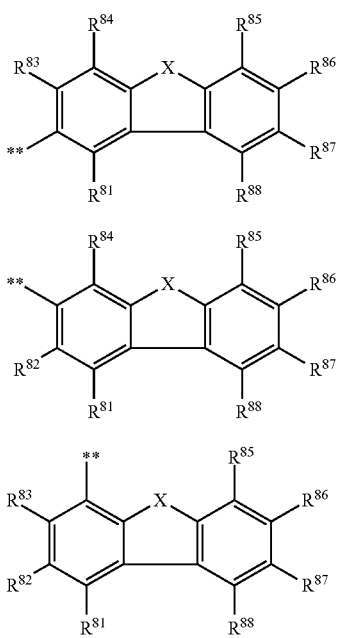

In one embodiment of the present invention, all $R^{61}$ to $R^{65}$ may be hydrogen atoms, all $R^{71}$ to $R^{78}$ not a single bond bonding to *b may be hydrogen atoms, and all $R^{81}$ to $R^{88}$ not a single bond bonding to *c may be hydrogen atoms.

Details of the substituted or unsubstituted alkyl group having 1 to 50 carbon atoms are as described in the section of "substituents referred to in this description", and the alkyl group is preferably a methyl group, an ethyl group, an n-propyl group, an isopropyl group, an n-butyl group, an isobutyl group, an s-butyl group, or a t-butyl group, more preferably a methyl group, an isopropyl group or a t-butyl group.

Details of the substituted or unsubstituted cycloalkyl group having 3 to 50 ring carbon atoms are as described in the section of "substituents referred to in this description", and the cycloalkyl group is preferably a cyclopropyl group, a cyclobutyl group, a cyclopentyl group, or a cyclohexyl group, more preferably a cyclopropyl group, a cyclopentyl group or a cyclohexyl group.

$R_{901}$, $R_{902}$ and $R_{903}$ in the group represented by —Si($R_{901}$)($R_{902}$)($R_{903}$) each are independently selected from a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms, and details thereof are as described in the section of "substituents referred to in this description".

The group represented by —Si($R_{901}$)($R_{902}$)($R_{903}$) is preferably a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group, more preferably a trimethylsilyl group or a triphenylsilyl group.

Details of the halogen atom are as described in the section of "substituents referred to in this description", and halogen atom is preferably a fluorine atom.

Details of the substituted or unsubstituted haloalkyl group having 1 to 50 carbon atoms are as described in the section of "substituents referred to in this description", and the haloalkyl group is preferably a substituted or unsubstituted fluoroalkyl group having 1 to 50 carbon atoms, more preferably a trifluoromethyl group, a 2,2,2-trifluoroethyl group, a pentafluoroethyl group, or a heptafluoropropyl group, more preferably a trifluoromethyl group.

Details of the substituted or unsubstituted alkoxy group having 1 to 50 carbon atoms are as described in the section of "substituents referred to in this description", and the alkoxy group is preferably a methoxy group, an ethoxy group, a propoxy group, or a t-butoxy group, more preferably a methoxy group or an ethoxy group, even more preferably a methoxy group.

Details of the substituted or unsubstituted aryloxy group having 6 to 50 ring carbon atoms are as described in the section of "substituents referred to in this description", and the aryloxy group is preferably a phenoxy group, a biphenyloxy group, or a terphenyloxy group, more preferably a phenoxy group or a biphenyloxy group, even more preferably a phenoxy group.

Details of the substituted or unsubstituted haloalkoxy group having 1 to 50, preferably 1 to 30, more preferably 1 to 18 carbon atoms is a group represented by —O(G12), in which G12 is a substituted or unsubstituted haloalkyl group referred to in the section of "substituents referred to in this description".

The substituted or unsubstituted haloalkoxy group having 1 to 50 carbon atoms is preferably a substituted or unsubstituted fluoroalkoxy group having 1 to carbon atoms, more preferably a trifluoromethoxy group, a 2,2,2-trifluoroethoxy group, a pentafluoroethoxy group, or a heptafluoropropoxy group, even more preferably a trifluoromethoxy group, a 2,2,2-trifluoroethoxy group or a pentafluoroethoxy group, further more preferably a trifluoromethoxy group.

Details of the substituted or unsubstituted aralkyl group having 7 to 50 carbon atoms are as described in the section of "substituents referred to in this description", and the aralkyl group is preferably a benzyl group, a phenyl-t-butyl group, an α-naphthylmethyl group, a β-naphthylmethyl group, a 1-β-naphthylisopropyl group, or a 2-β-naphthylisopropyl group, more preferably a benzyl group, a phenyl-t-butyl group, an α-naphthylmethyl group or a β-naphthylmethyl group.

$R^{11}$ to $R^{15}$, $R^{21}$ to $R^{27}$, $R^{41}$ to $R^{45}$, and $R^{51}$ to $R^{55}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group;

preferably each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), and a cyano group;

more preferably each are independently selected from a hydrogen atom, a substituted or unsubstituted aryl group having 6 to 50 ring carbon atoms, a substituted or unsubstituted heterocyclic group having 5 to 50 ring atoms, and a substituted or unsubstituted alkyl group having 1 to 50 carbon atoms.

One selected from $R^{11}$ to $R^{13}$ is a single bond bonding to *a.

Details of the substituted or unsubstituted alkyl group having 1 to 50 carbon atoms, the substituted or unsubstituted cycloalkyl group having 3 to 50 ring carbon atoms, the group represented by —Si($R_{901}$)($R_{902}$)($R_{903}$), the halogen atom, the substituted or unsubstituted haloalkyl group having 1 to 50 carbon atoms, the substituted or unsubstituted alkoxy group having 1 to 50 carbon atoms, the substituted or unsubstituted aryloxy group having 6 to 50 ring carbon atoms, the substituted or unsubstituted haloalkoxy group having 1 to 50 carbon atoms, and the substituted or unsubstituted aralkyl group having 7 to 50 carbon atoms are the same as the details of the corresponding groups represented by $R^{61}$ to $R^{65}$, $R^{71}$ to $R^{78}$, and $R^{81}$ to $R^{88}$.

Details of the substituted or unsubstituted aryl group having 6 to 50 ring carbon atoms are as described in the section of "substituents referred to in this description", and the aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, a fluorenyl group, a 9,9'-spirobifluorenyl group, a 9,9-dimethylfluorenyl group, or a 9,9-diphenylfluorenyl group, more preferably a phenyl group, a p-biphenyl group, a m-biphenyl group, an o-biphenyl group, a 1-naphthyl group, a 2-naphthyl group, a fluorenyl group, a 9,9'-spirobifluorenyl group, a 9,9-dimethylfluorenyl group or a 9,9-diphenylfluorenyl group.

Details of the substituted or unsubstituted heterocyclic group having 5 to 50 ring atoms are as described in the section of "substituents referred to in this description", and the heterocyclic group is more preferably a carbazolyl group (a 1-carbazolyl group, a 2-carbazolyl group, a 3-carbazolyl group, a 4-carbazolyl group or a 9-carbazolyl group), a dibenzofuranyl group, a naphthobenzofuranyl group, a dibenzothiophenyl group, a naphthobenzothiophenyl group, a phenyldibenzofuranyl group, or a phenyldibenzothiophenyl group, even more preferably a carbazolyl group (a 1-carbazolyl group, a 2-carbazolyl group, a 3-carbazolyl group, a 4-carbazolyl group, or a 9-carbazolyl group), a dibenzofuranyl group, or a dibenzothiophenyl group.

$R^{31}$ to $R^{37}$ each are independently selected from a hydrogen atom, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group;

preferably each are independently selected from a hydrogen atom, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), and a cyano group:

more preferably each are independently selected from a hydrogen atom, and a substituted or unsubstituted alkyl group having 1 to 50 carbon atoms.

Details of the substituted or unsubstituted alkyl group having 1 to 50 carbon atoms, the substituted or unsubstituted cycloalkyl group having 3 to 50 ring carbon atoms, the group represented by —Si($R_{901}$)($R_{902}$)($R_{903}$), the halogen atom, the substituted or unsubstituted haloalkyl group having 1 to 50 carbon atoms, the substituted or unsubstituted alkoxy group having 1 to 50 carbon atoms, the substituted or unsubstituted aryloxy group having 6 to 50 ring carbon atoms, the substituted or unsubstituted haloalkoxy group having 1 to 50 carbon atoms, and the substituted or unsubstituted aralkyl group having 7 to 50 carbon atoms are the same as the details of the corresponding groups referred to hereinabove relative to $R^{61}$ to $R^{65}$, $R^{71}$ to $R^{78}$, and $R^{81}$ to $R^{88}$.

Details of the substituted or unsubstituted heterocyclic group having 5 to 50 ring atoms are the same as the details of the substituted or unsubstituted heterocyclic group having 5 to 50 ring atoms referred to hereinabove relative to $R^{11}$ to $R^{15}$, $R^{21}$ to $R^{27}$, $R^{41}$ to $R^{45}$, and $R^{51}$ to $R^{55}$.

In one embodiment of the present invention,
(1) all RH to $R^{15}$ not a single bond bonding to *a may be hydrogen atoms,
(2) all $R^{21}$ to $R^{27}$ may be hydrogen atoms,
(3) all $R^{31}$ to $R^{37}$ may be hydrogen atoms,
(4) all $R^{41}$ to $R^{45}$ (but $R^{41}$ to $R^{44}$ when $R^{45}$ and $R^{51}$ bond to each other) may be hydrogen atoms
(5) all $R^{51}$ to $R^{55}$ (but $R^{52}$ to $R^{55}$ when $R^{45}$ and $R^{51}$ bond to each other) may be hydrogen atoms.

The inventive compound may satisfy all the above-mentioned requirements (1) to (5) at the same time, or may satisfy a part of the requirements (1) to (5).

One pair or more of combinations formed of neighboring two or more selected from $R^{21}$ to $R^{27}$ and $R^{31}$ to $R^{37}$ bond to each other to form a substituted or unsubstituted single ring, or bond to each other to form a substituted or unsubstituted condensed ring, or do not bond to each other. Namely, the neighboring two of one pair or more selected from $R^{21}$ and $R^{22}$, $R^{22}$ and $R^{23}$, $R^{24}$ and $R^{25}$, $R^{25}$ and $R^{26}$, $R^{26}$ and $R^{27}$, $R^{32}$ and $R^{33}$, $R^{34}$ and $R^{35}$, $R^{35}$ and $R^{36}$, and $R^{36}$ and $R^{37}$ bond to each other to form a substituted or unsubstituted single ring, or bond to each other to form a substituted or unsubstituted condensed ring, or do not bond to each other.

For example, in one or more pairs of combinations of the neighboring two selected from $R^{21}$ to $R^{27}$ and $R^{31}$ to $R^{37}$, the neighboring two contained in each pair bond to each other to form a substituted or unsubstituted single ring, or bond to each other to form a substituted or unsubstituted condensed ring, or do not bond to each other.

The above-mentioned one pair or more may be selected in such a manner that one pair (the first pair) and the other one pair (second pair) can share one ring carbon atom (the ring carbon atom to which $R^{22}$ bonds), such as a pair of, $R^{21}$ and $R^{22}$, and a pair of $R^{22}$ and $R^{23}$, or the neighboring two contained in each pair ($R^{21}$ and $R^{22}$, and $R^{22}$ and $R^{23}$) may bond to each other to form a substituted or unsubstituted single ring, or a substituted or unsubstituted condensed ring. In this case, the ring formed by the neighboring two contained in the one pair, the ring formed by the neighboring two contained in the other one pair, and the ring to which the neighboring two contained in the one pair and in the other one pair bond form an ortho-peri-condensed structure.

The substituted or unsubstituted single ring or the substituted or unsubstituted condensed ring is selected, for example, from a substituted or unsubstituted aromatic hydrocarbon ring, a substituted or unsubstituted aliphatic hydrocarbon ring, a substituted or unsubstituted aromatic hetero ring, and a substituted or unsubstituted aliphatic hetero ring.

For example, the aromatic hydrocarbon ring is a benzene ring, a biphenylene ring, a naphthalene ring, an anthracene ring, a benzanthracene ring, a phenanthrene ring, a benzophenanthrene ring, a phenalene ring, a pyrene ring, a chrysene ring, a 1,1-dimethylindene ring, or a triphenylene ring, preferably a benzene ring or a naphthalene ring, more preferably a benzene ring.

The aliphatic hydrocarbon ring is, for example, a cyclopentene ring, a cyclopentadiene ring, a cyclohexene ring, a cyclohexadiene ring, or an aliphatic hydrocarbon ring formed by partially hydrogenating the aromatic hydrocarbon ring.

The aromatic hetero ring is, for example, a pyrrole ring, a furan ring, a thiophene ring, a pyridine ring, an imidazole ring, a pyrazole ring, an indole ring, an isoindole ring, a benzofuran ring, an isobenzofuran ring, a benzothiophene ring, a benzimidazole ring, an indazole ring, a dibenzofuran ring, a naphthobenzofuran ring, a dibenzothiophene ring, a naphthobenzothiophene ring, a carbazole ring, or a benzocarbazole ring.

The aliphatic hetero ring is, for example, an aliphatic hetero ring formed by partially hydrogenating the aromatic hetero ring.

$R^{45}$ and $R^{51}$ bond to each other to form a single bond that bonds the two benzene rings to which these bond, or do not bond to each other. In one embodiment of the present invention, preferably, $R^{45}$ and $R^{51}$ bond to each other to form the above-mentioned single bond, and in another embodiment, preferably, $R^{45}$ and $R^{51}$ do not bond to each other.

Accordingly, the inventive compound includes compounds represented by any of the following formula (17) to (25).

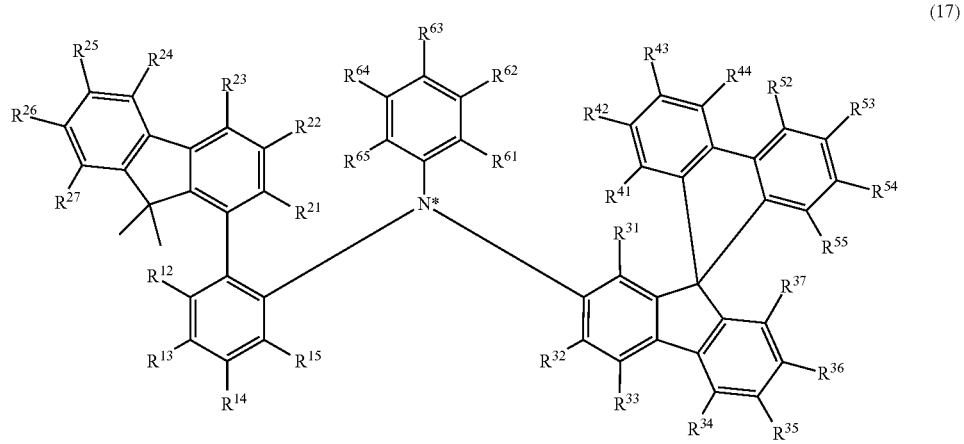

(17)

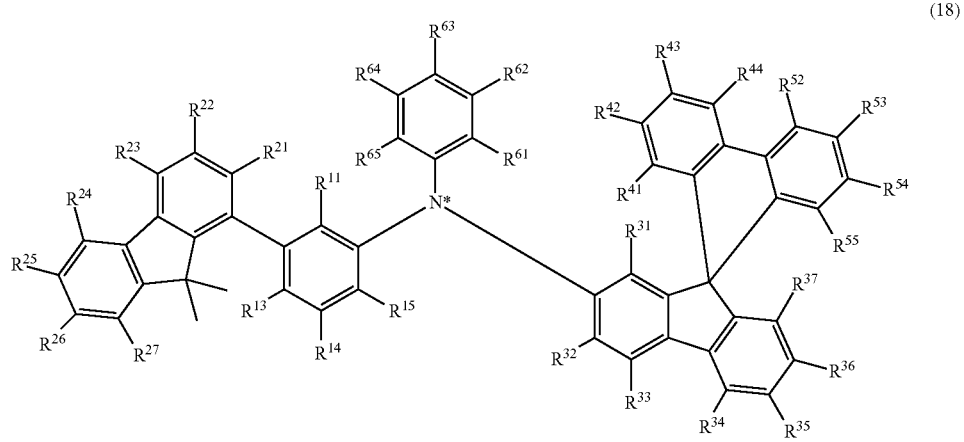

(18)

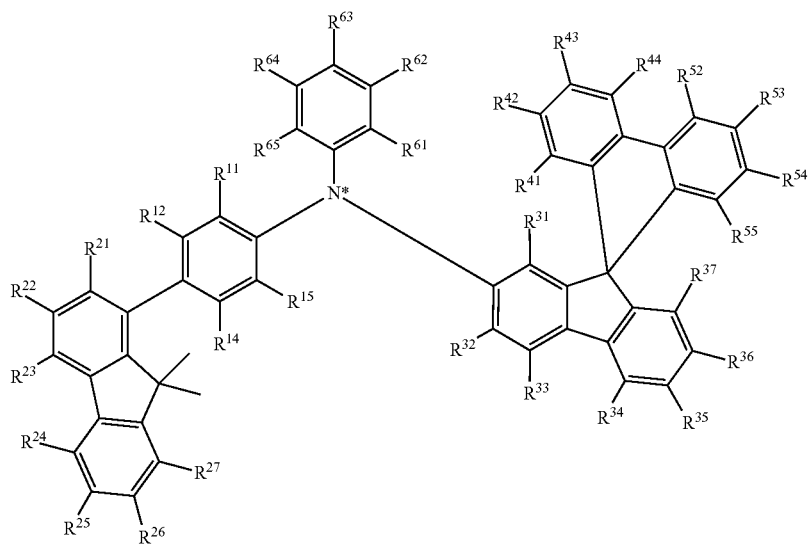
(19)
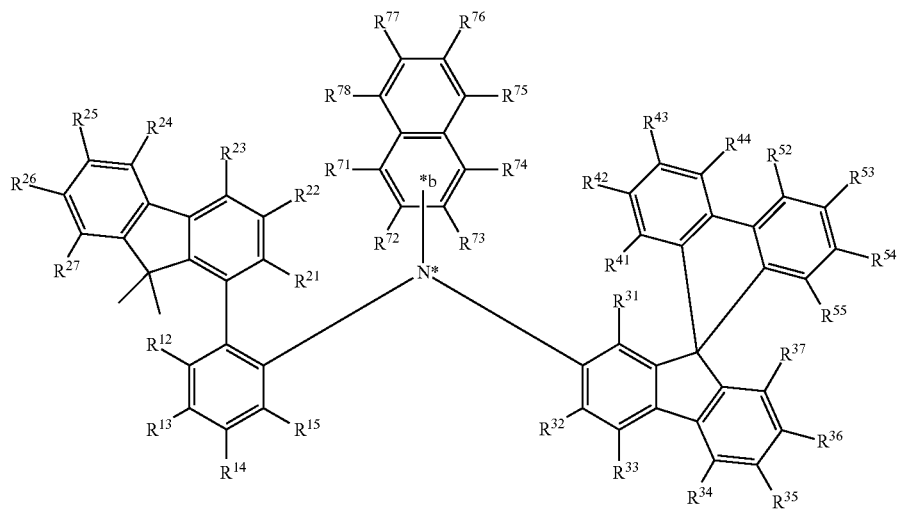
(20)
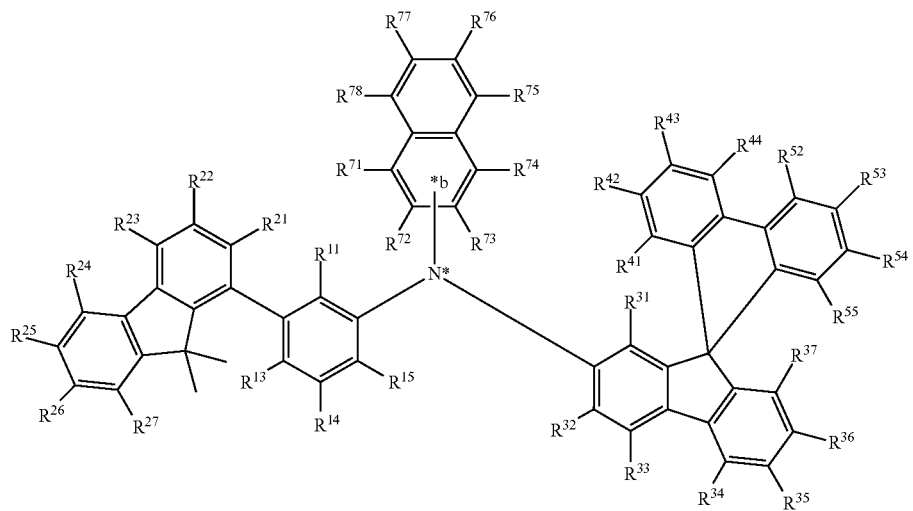
(21)

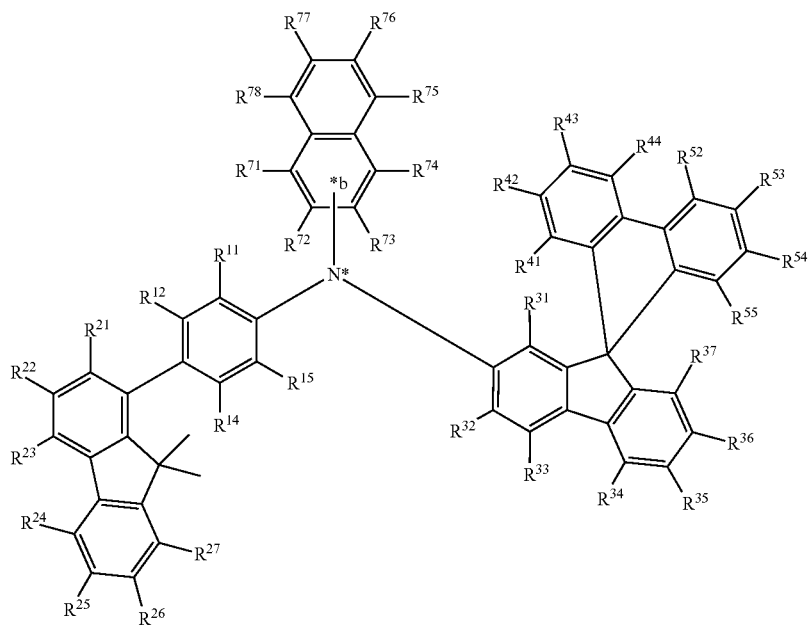
(22)
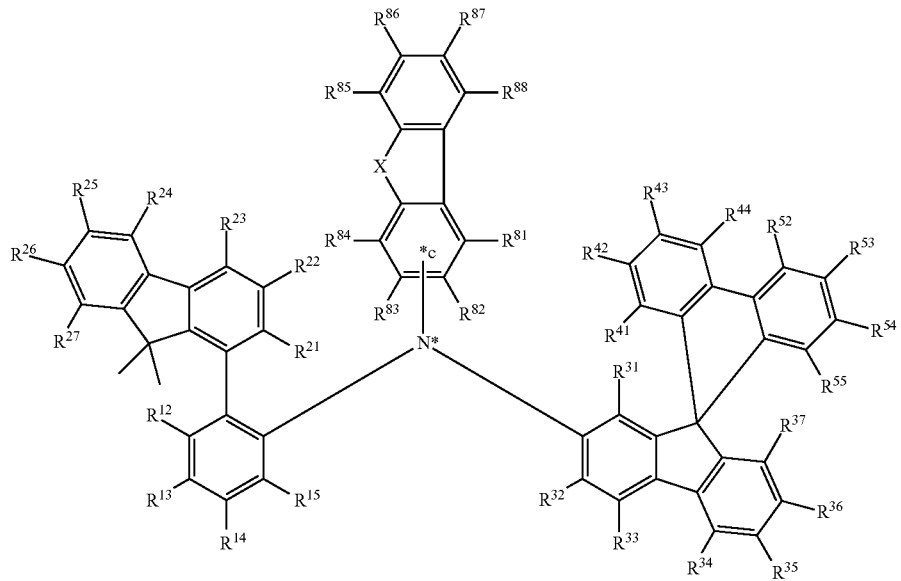
(23)

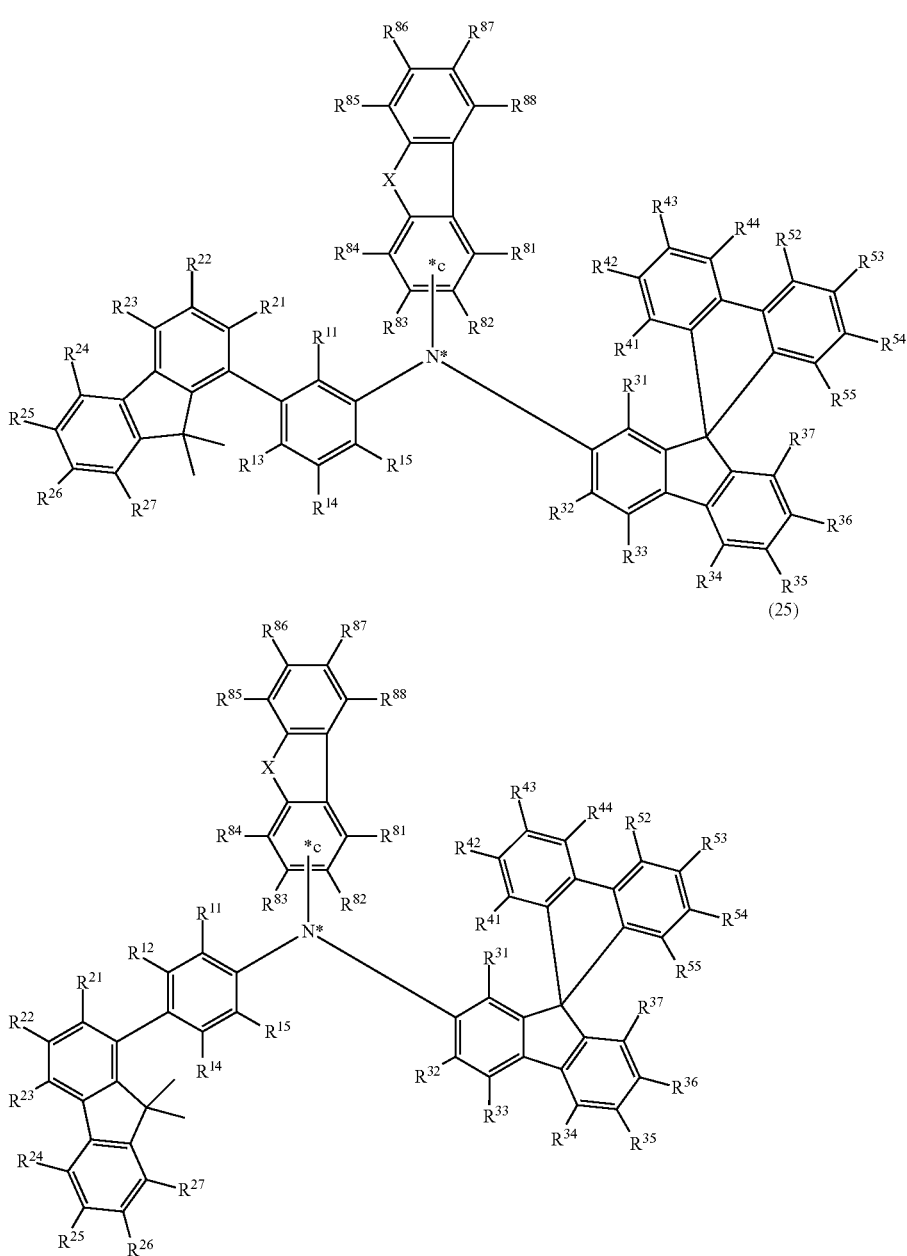

As noted above, the "hydrogen atom" referred to in this description includes a light hydrogen (protium) atom, a heavy hydrogen (deuterium) atom, and a tritium atom. Therefore, the inventive compound may include a naturally occurring heavy hydrogen atom.

In addition, a heavy hydrogen atom may be intentionally introduced into the inventive compound by using a deuterated compound as a part or whole of the raw material compounds. Thus, in an embodiment of the invention, the inventive compound comprises at least one heavy hydrogen atom. Therefore, the inventive compound may be a compound represented by the formula (1) or any other formula, in which at least one hydrogen atom contained in the compound is a heavy hydrogen atom.

At least one hydrogen atom selected from the hydrogen atom represented by any of $R^{11}$ to $R^{45}$, $R^{21}$ to $R^{27}$, $R^{41}$ to $R^{45}$, and $R^{51}$ to $R^{55}$; the hydrogen atom that a substituted or unsubstituted, aryl group, heterocyclic group, alkyl group, cycloalkyl group, haloalkyl group, alkoxy group, aryloxy group, haloalkoxy group, aralkyl group or group represented by —Si($R_{901}$)($R_{902}$)($R_{903}$), as represented by any of $R^{11}$ to $R^{15}$, $R^{21}$ to $R^{27}$, $R^{41}$ to $R^{45}$, and $R^{51}$ to $R^{55}$, has;

the hydrogen atom represented by any of $R^{31}$ to $R^{37}$; the hydrogen atom that a substituted or unsubstituted, heterocyclic group, alkyl group, cycloalkyl group, haloalkyl group, alkoxy group, aryloxy group, haloalkoxy group, aralkyl group or group represented by —Si($R_{901}$)($R_{902}$)($R_{903}$), as represented by any of $R^{31}$ to $R^{37}$, has; and the hydrogen atom represented by any of $R^{61}$ to $R^{65}$, $R^{71}$ to $R^{78}$, and $R^{81}$ to $R^{88}$; and the hydrogen atom that a substituted or unsubstituted, alkyl group, cycloalkyl group, haloalkyl group, alkoxy group, aryloxy group, haloalkoxy group, aralkyl group or group represented by —Si($R_{901}$)($R_{902}$)($R_{903}$), as represented by any of $R^{61}$ to $R^{65}$, $R^{71}$ to $R^{78}$, and $R^{81}$ to $R^{88}$, has may be a heavy hydrogen atom.

The deuteration rate of the inventive compound (the ratio of the number of heavy hydrogen atoms to the total number of hydrogen atoms in the inventive compound) depends on the deuteration rate of the raw material compound to be used. It is generally difficult to use the raw material compounds each having a deuteration rate of 100%. Therefore, the deuteration rate of the inventive compound is less than 100% and 1% or more, preferably 3% or more, more preferably 5% or more, and still more preferably 10% or more.

The inventive compound may be a mixture of a deuterated compound (a compound into which a heavy hydrogen atom has been intentionally introduced) and a non-deuterated compound or a mixture of two or more compounds having different deuteration rates. The deuteration rate of such a mixture (the ratio of the number of heavy hydrogen atoms to the total number of hydrogen atoms in the inventive compound contained in the mixture) is 1% or more, preferably 3% or more, more preferably 5% or more, and still more preferably 10% or more, and less than 100%.

In the inventive compound, at least one hydrogen atom selected from the hydrogen atom represented by any of $R^{11}$ to $R^{15}$, $R^{21}$ to $R^{27}$, $R^{41}$ to $R^{45}$, and $R^{51}$ to $R^{55}$, as well as the hydrogen atom that a substituted or unsubstituted, aryl group, heterocyclic group, alkyl group, cycloalkyl group, haloalkyl group, alkoxy group, aryloxy group, haloalkoxy group, aralkyl group or group represented by —Si($R_{901}$)($R_{902}$)($R_{903}$), as represented by any of $R_{11}$ to $R_{15}$, $R_{21}$ to $R_{27}$, $R_{41}$ to $R_{45}$, and $R^{51}$ to $R^{55}$, has may be a heavy hydrogen atom.

The deuteration rate (the ratio of the number of heavy hydrogen atoms to the total number of hydrogen atoms that $R^{11}$ to $R^{15}$, $R^{21}$ to $R^{27}$, $R^{41}$ to $R^{45}$, and $R^{51}$ to $R^{55}$ has) is 1% or more, preferably 3% or more, more preferably 5% or more, and still more preferably 10% or more, and less than 100%.

In the inventive compound, at least one hydrogen atom selected from the hydrogen atom represented by any of $R^{31}$ to $R^{37}$, and the hydrogen atom that a substituted or unsubstituted, heterocyclic group, alkyl group, cycloalkyl group, haloalkyl group, alkoxy group, aryloxy group, haloalkoxy group, aralkyl group or group represented by —Si($R_{901}$)($R_{902}$)($R_{903}$), as represented by any of $R^{31}$ to $R^{37}$, has may be a heavy hydrogen atom.

The deuteration rate (the ratio of the number of heavy hydrogen atoms to the total number of hydrogen atoms that $R^{31}$ to $R^{37}$ has) is 1% or more, preferably 3% or more, more preferably 5% or more, and still more preferably 10% or more, and less than 100%.

In the inventive compound, at least one hydrogen atom selected from the hydrogen atom represented by any of $R^{61}$ to $R^{65}$, $R^{71}$ to $R^{78}$, and $R^{81}$ to $R^{88}$, and the hydrogen atom that a substituted or unsubstituted, alkyl group, cycloalkyl group, haloalkyl group, alkoxy group, aryloxy group, haloalkoxy group, aralkyl group or group represented by —Si($R_{901}$)($R_{902}$)($R_{903}$), as represented by any of $R^{61}$ to $R^{65}$, $R^{71}$ to $R^{78}$, and $R^{81}$ to $R^{88}$, has may be a heavy hydrogen atom.

The deuteration rate (the ratio of the number of heavy hydrogen atoms to the total number of hydrogen atoms that $R^{61}$ to $R^{55}$, $R^{71}$ to $R^{78}$, and $R^{81}$ to $R^{88}$ has) is 1% or more, preferably 3% or more, more preferably 5% or more, and still more preferably 10% or more, and less than 100%.

For the details of the substituent (arbitrary substituent) in the case of "substituted or unsubstituted" included in the definition of each formula mentioned above, reference may be made to the description referred to hereinabove for the "substituent in the case of 'substituted or unsubstituted'".

One of ordinary skill in the art could easily produce the inventive compound by referring to the Synthesis Examples mentioned below and known synthesis methods.

Specific examples of the inventive compound are shown below, although not limited thereto.

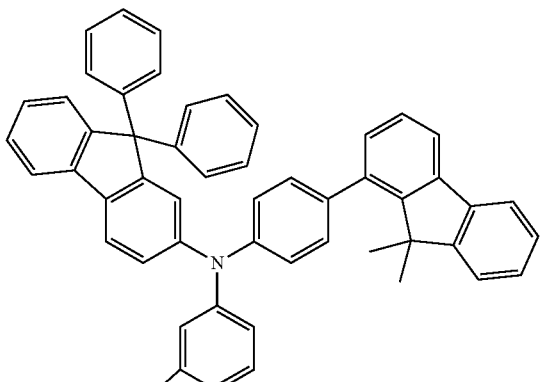

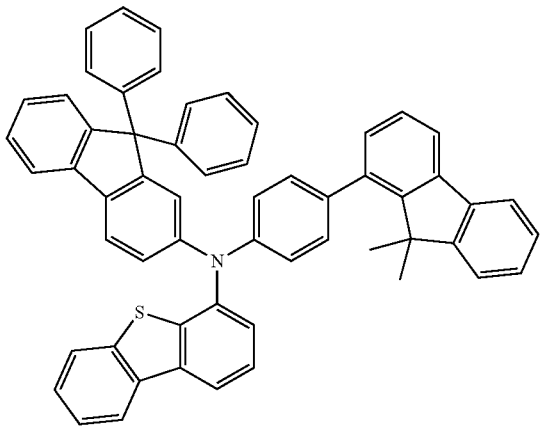

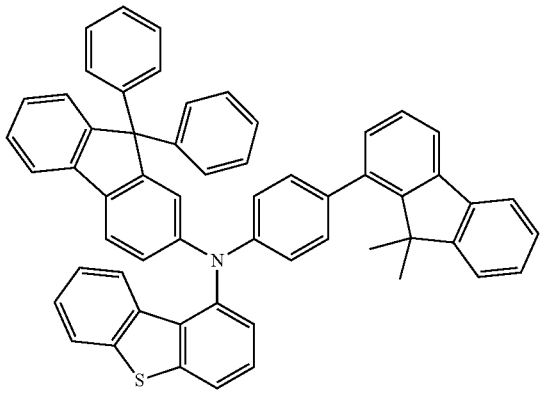

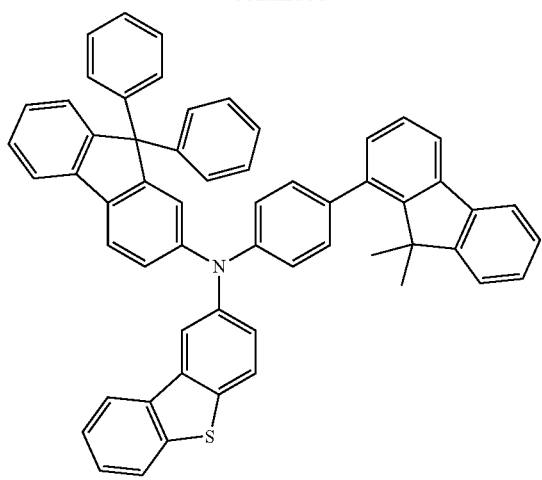
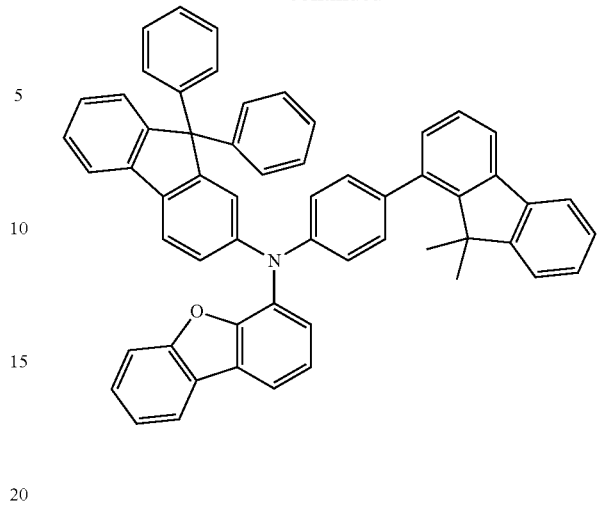
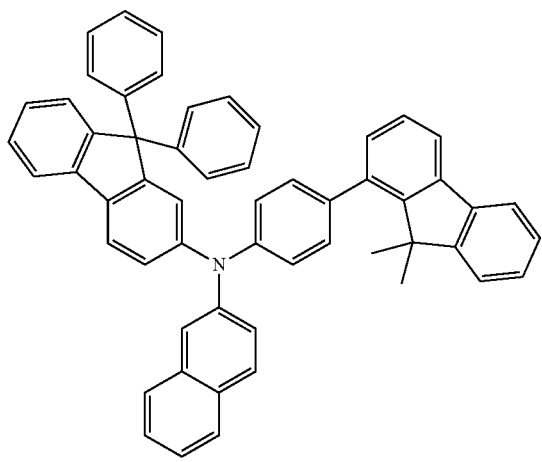
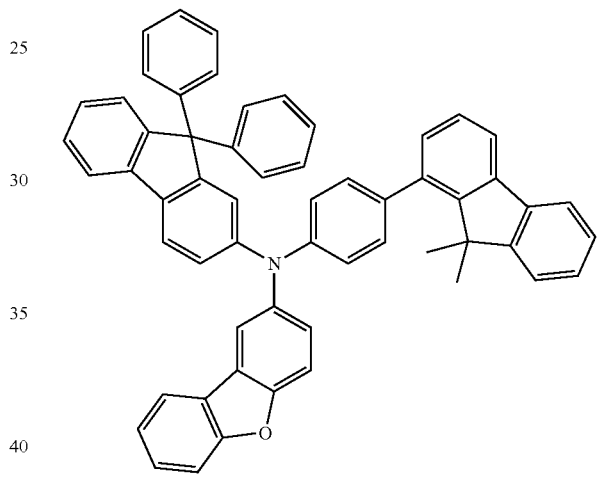
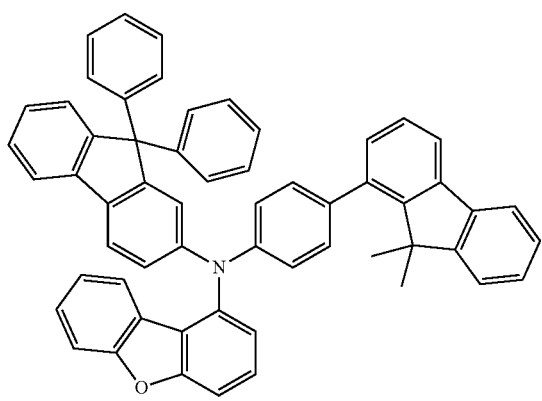
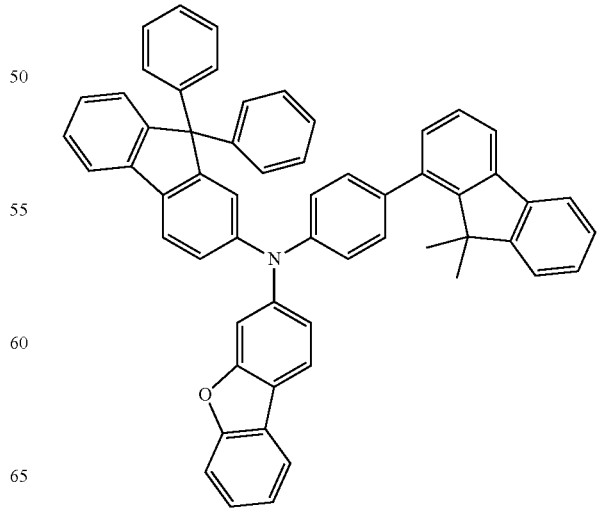

65
-continued
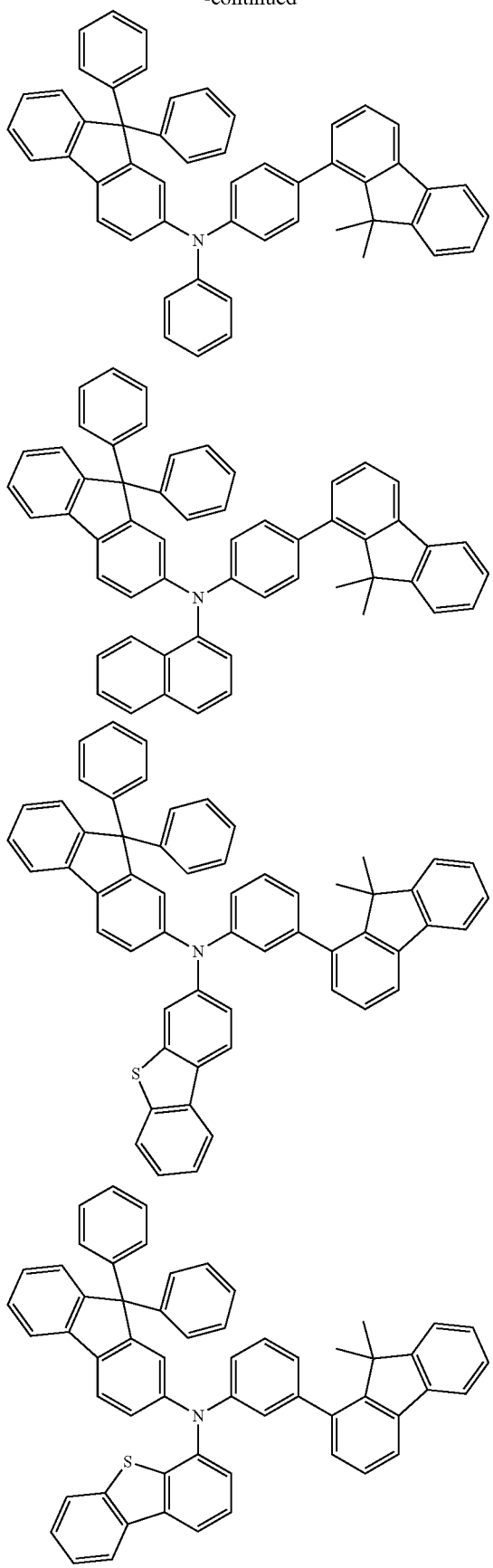
66
-continued
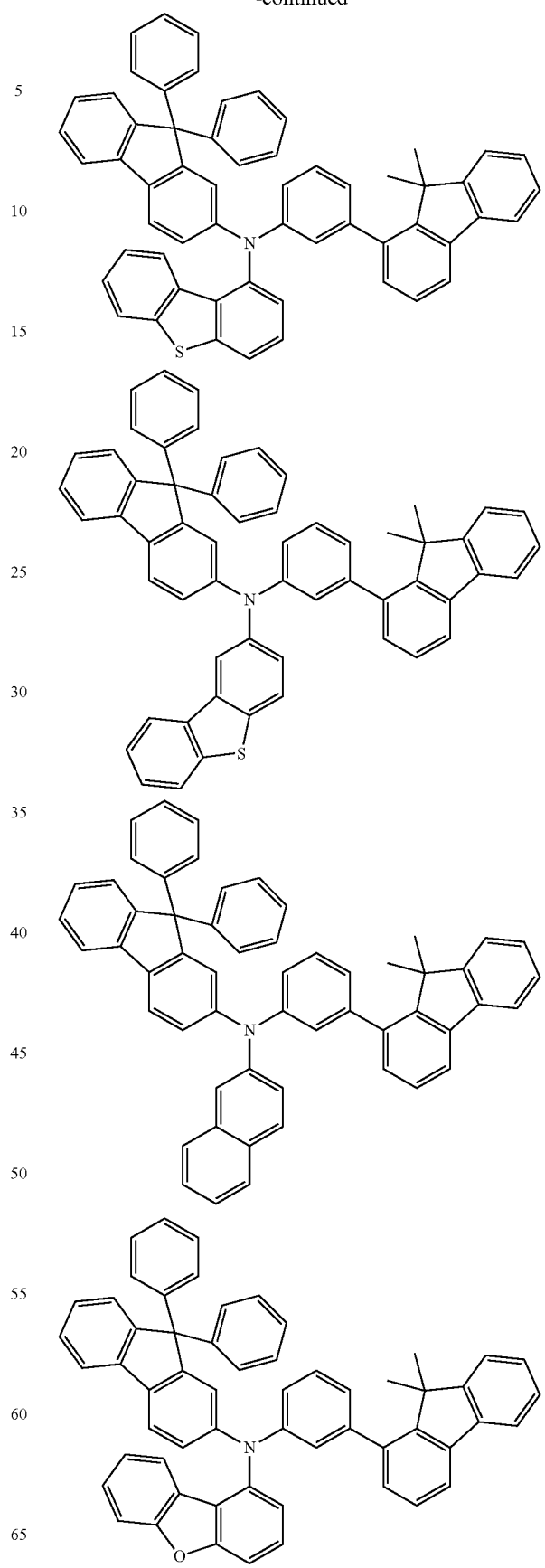

-continued
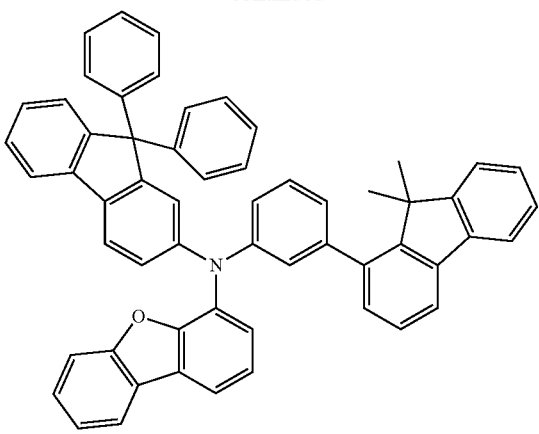
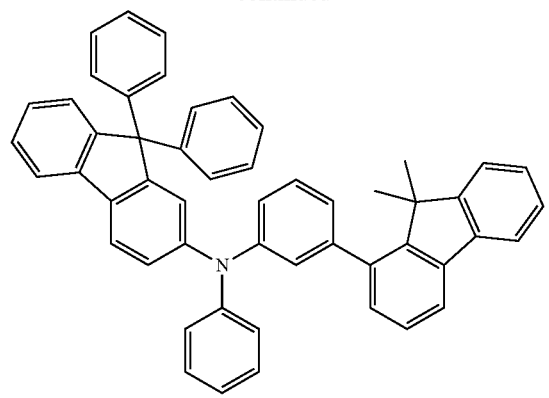
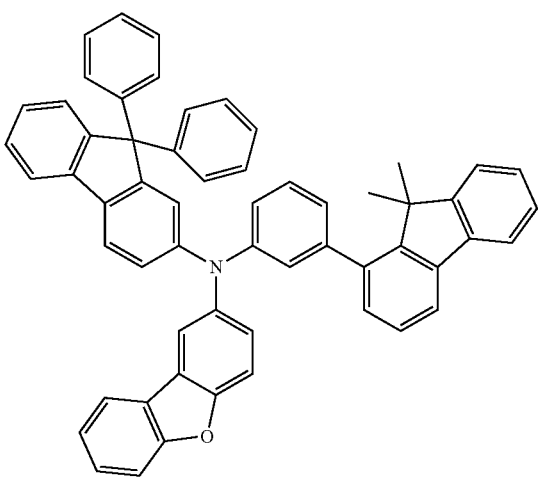
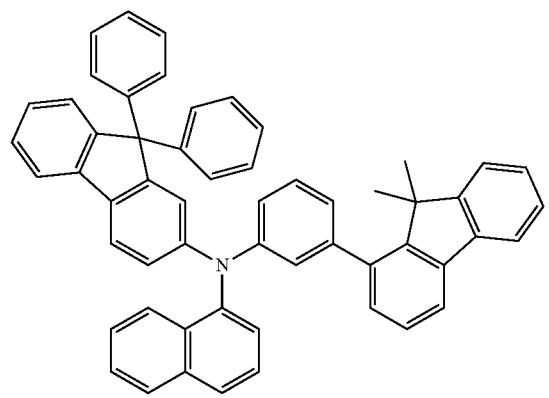
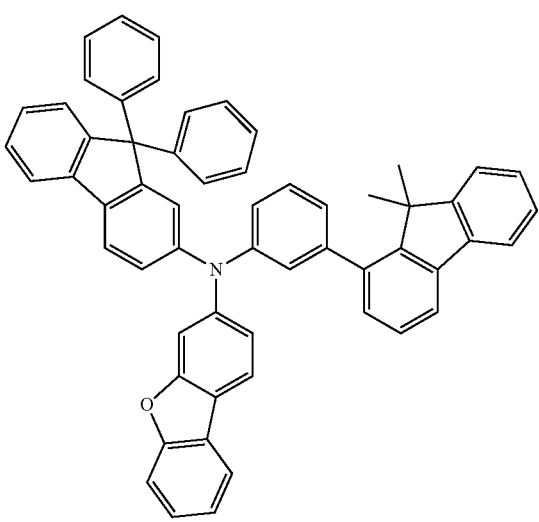
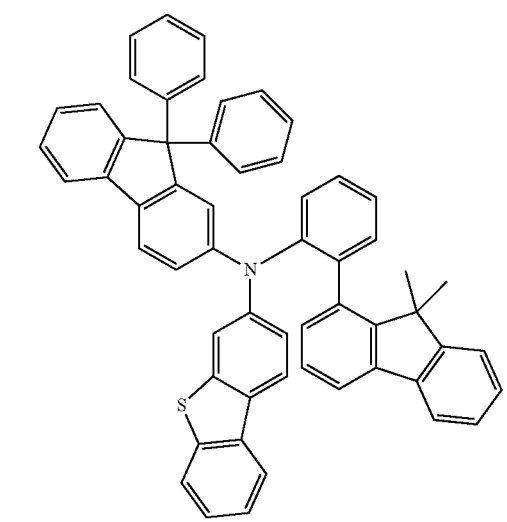

69
-continued
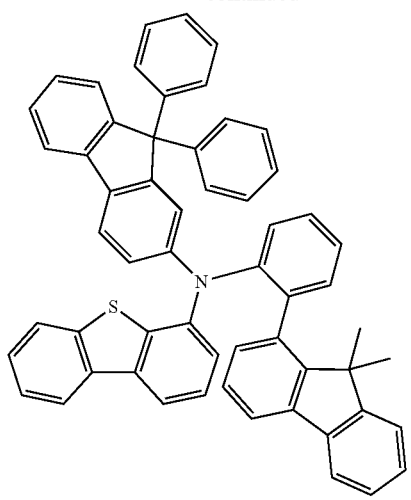
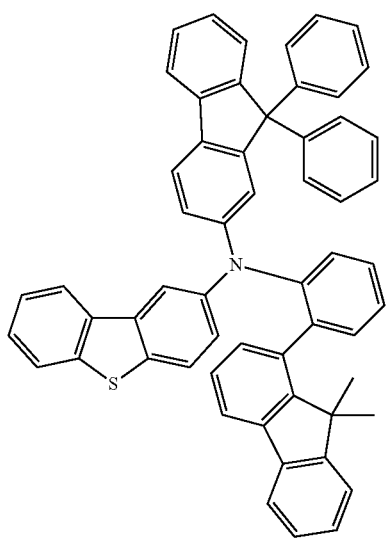
70
-continued
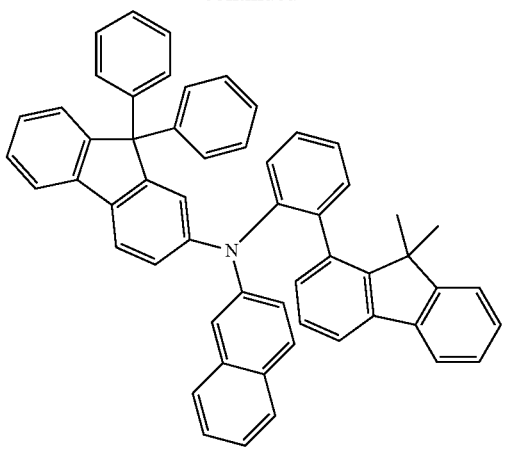
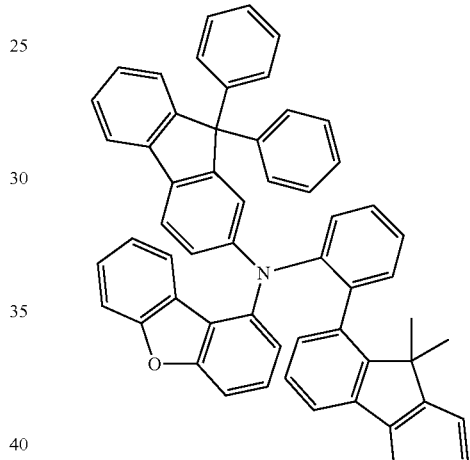
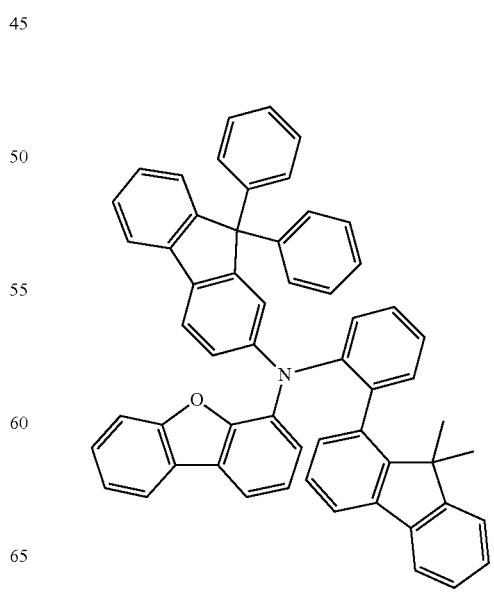

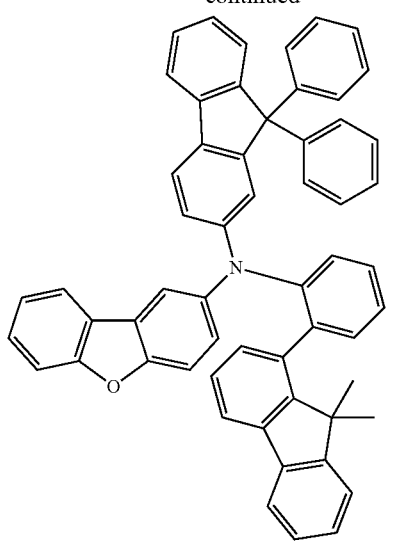
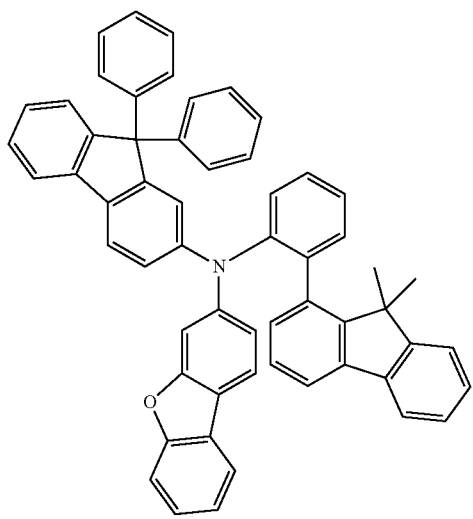
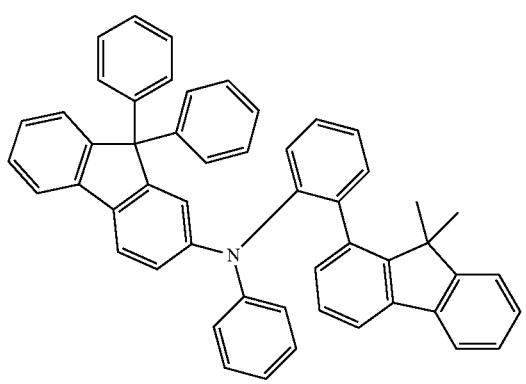
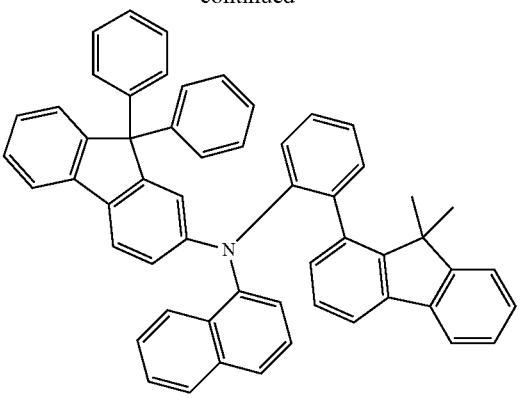
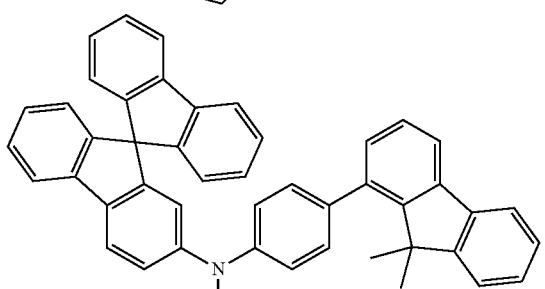
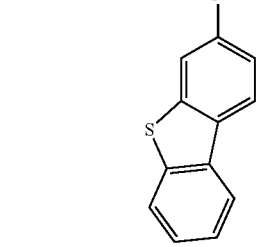
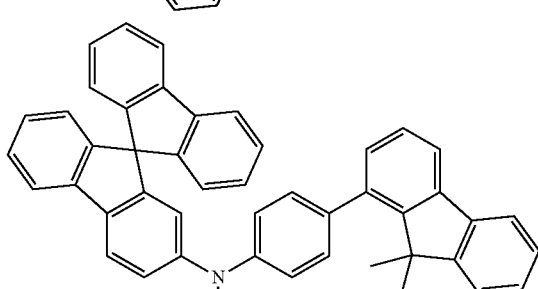
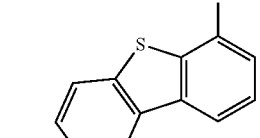
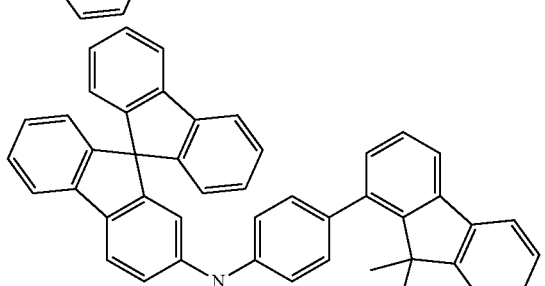
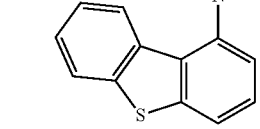

73
-continued
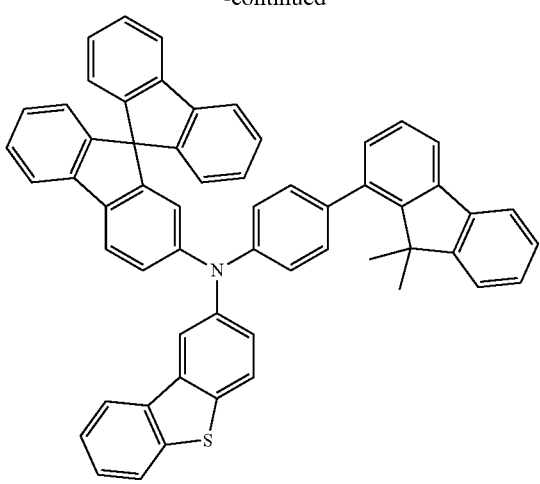
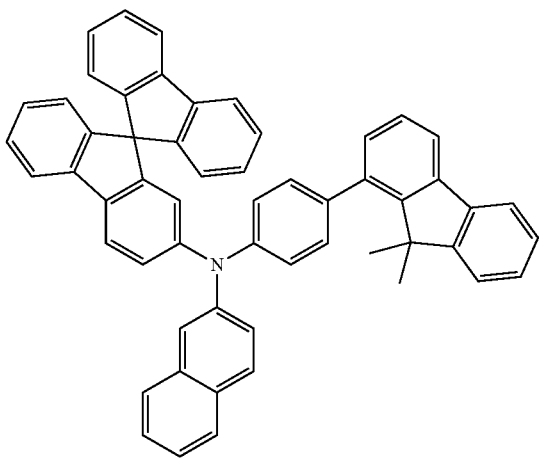
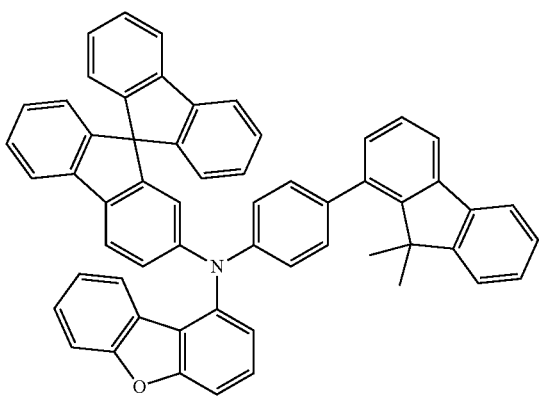
74
-continued
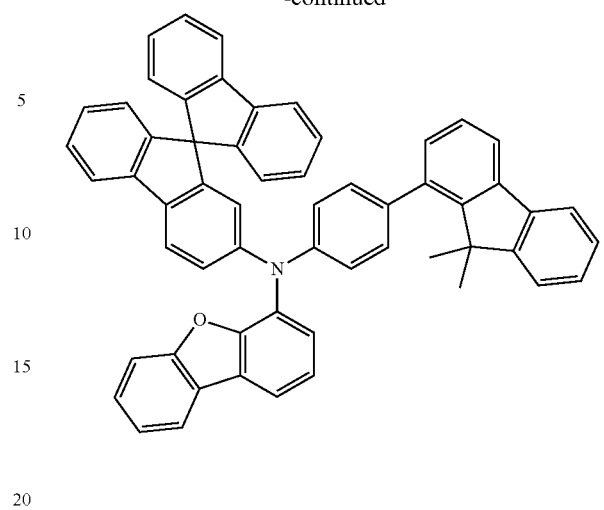
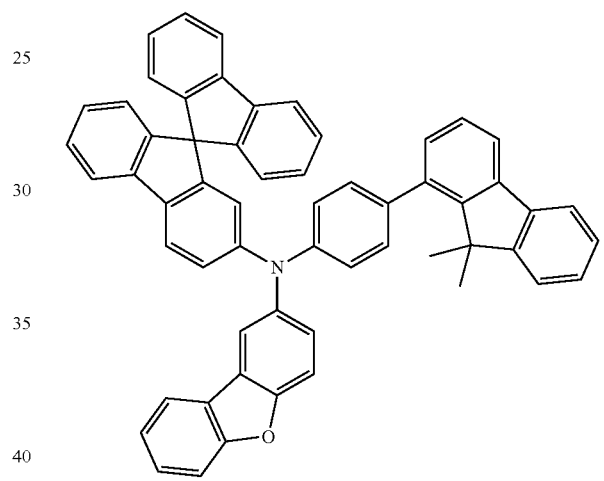
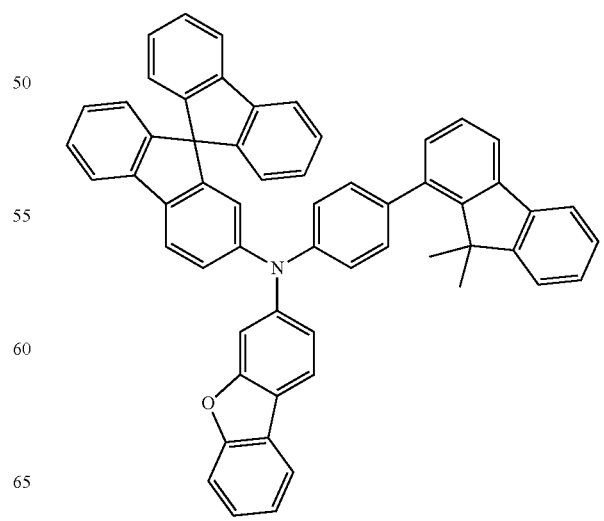

75
-continued
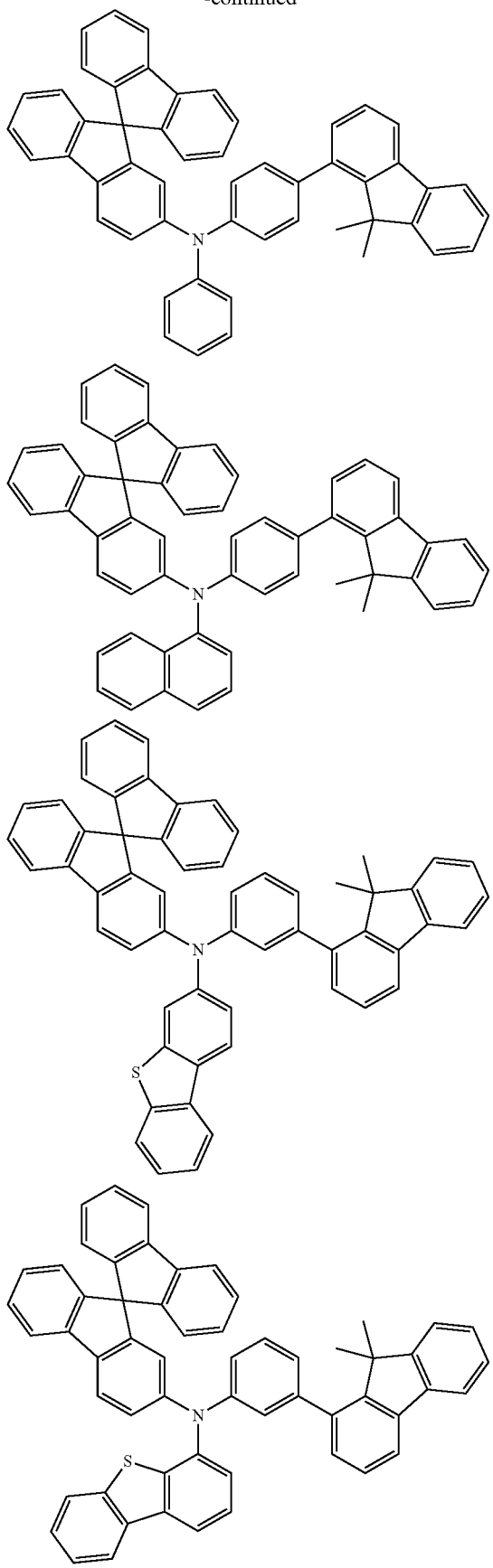
76
-continued
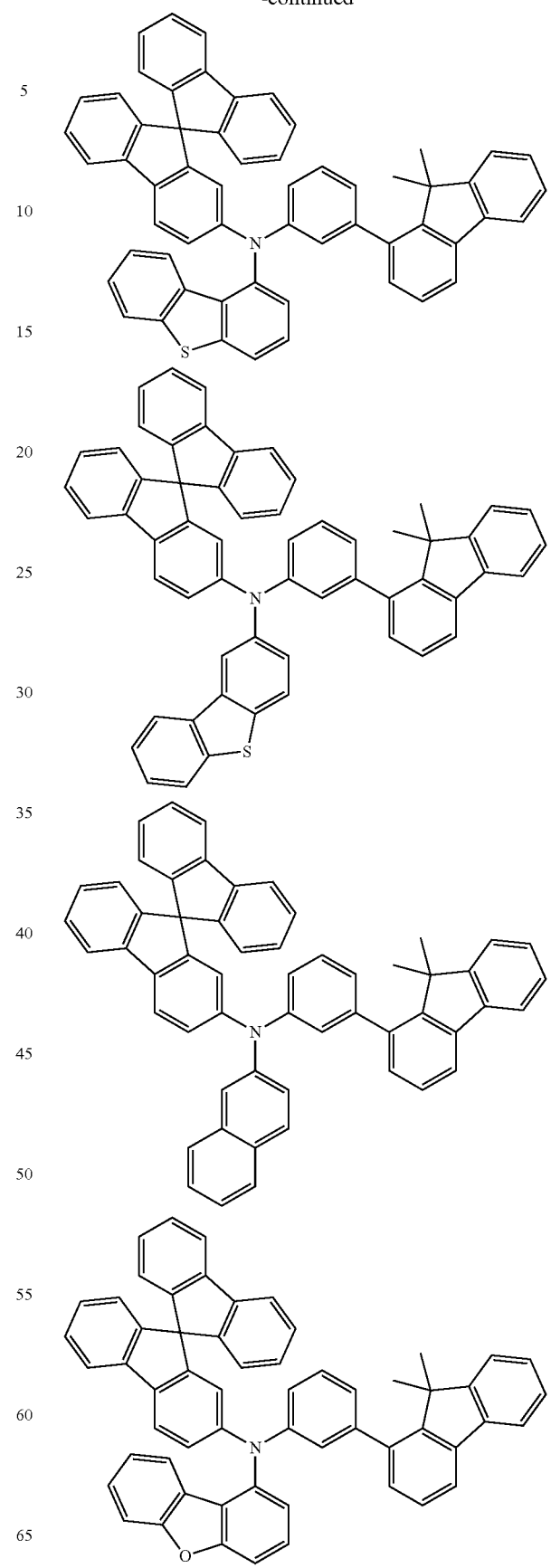

77
-continued
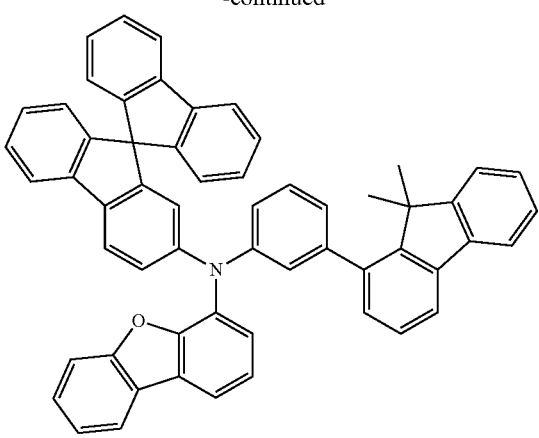
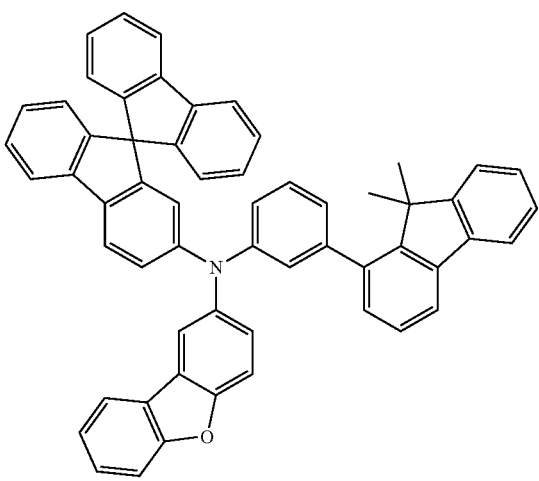
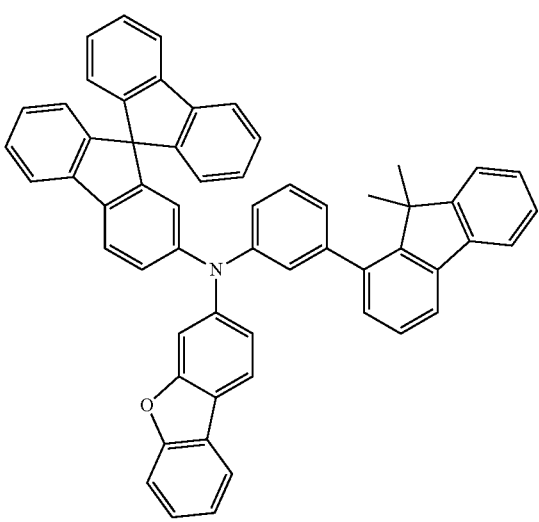
78
-continued
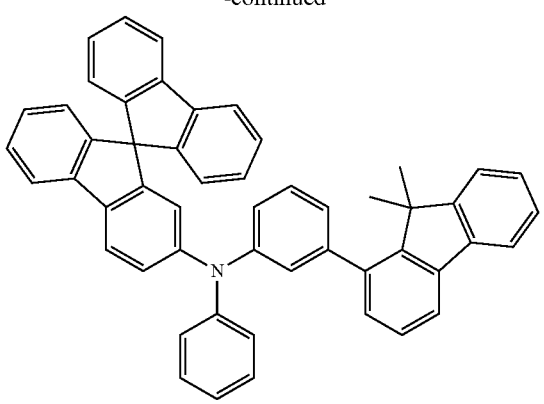
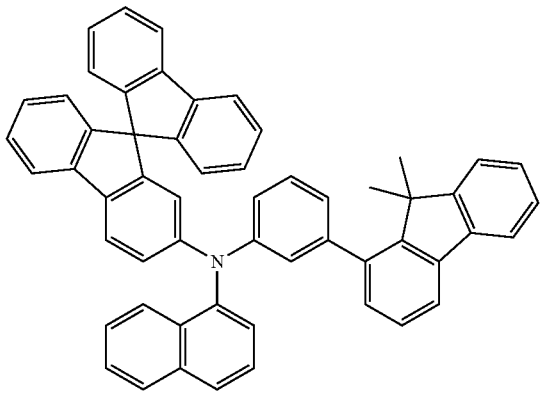
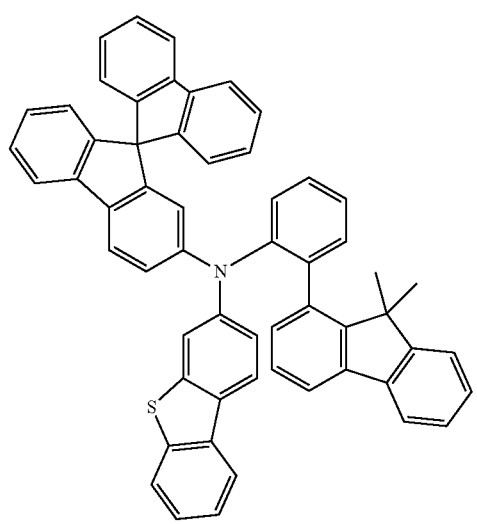

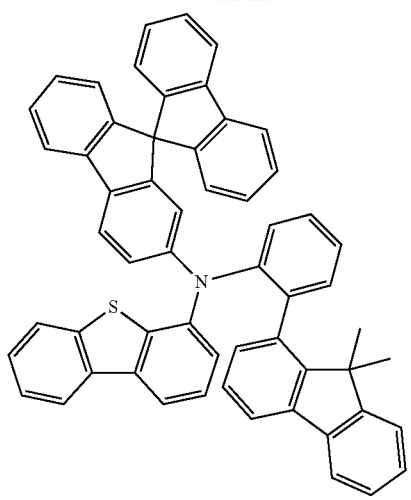
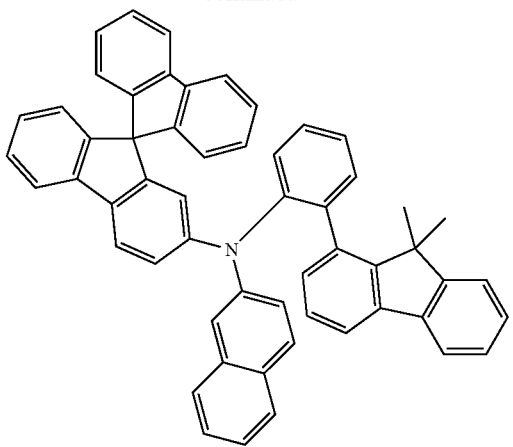
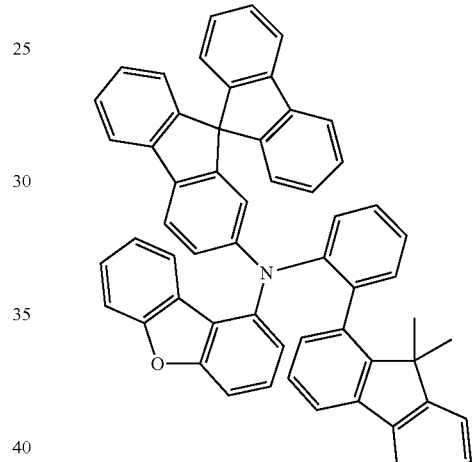
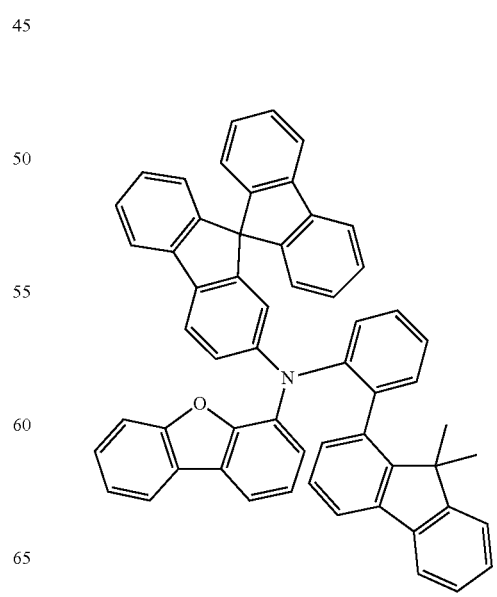
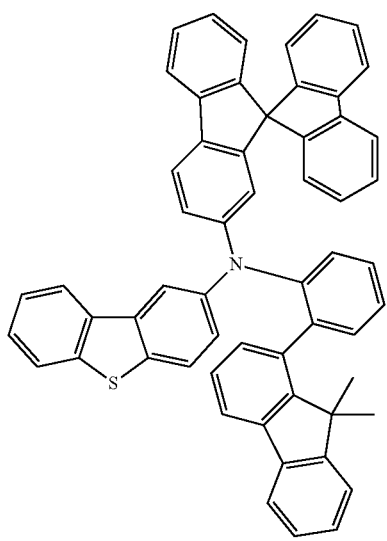

-continued
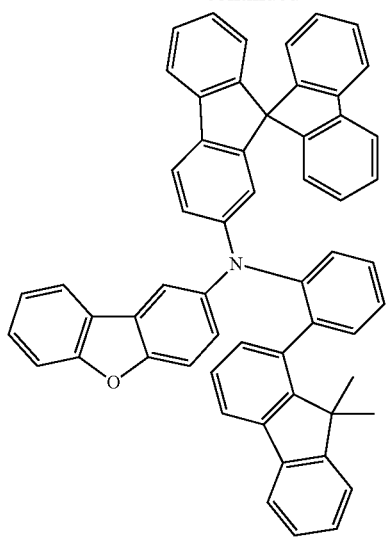
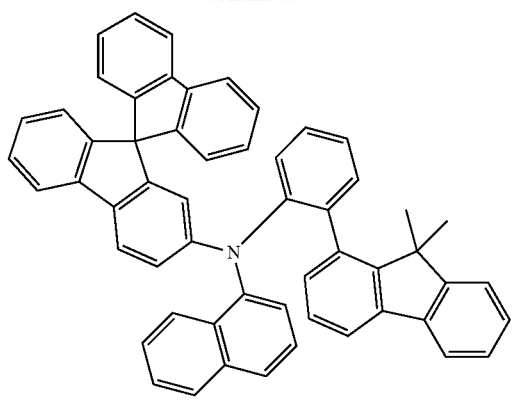
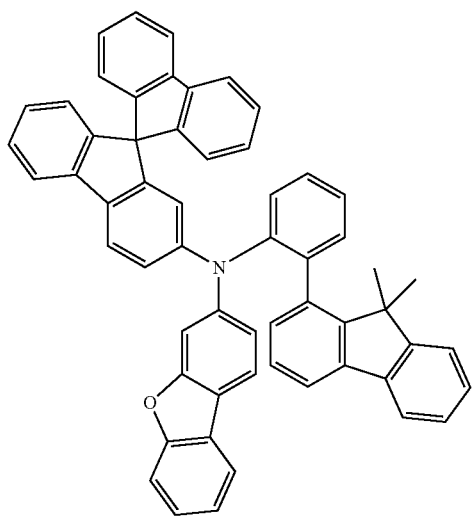
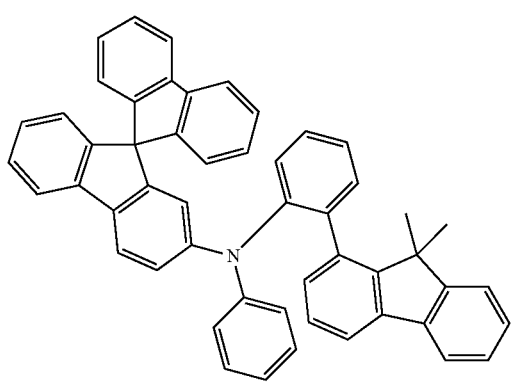
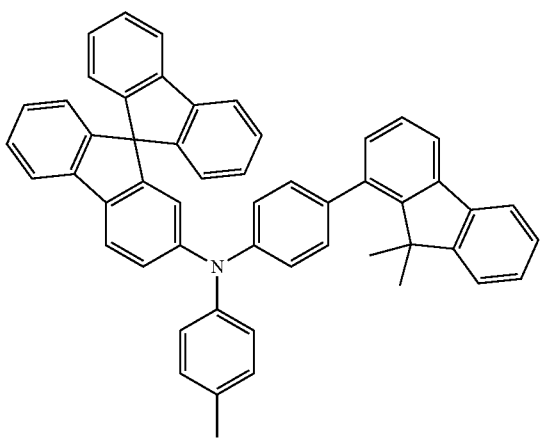

83
-continued
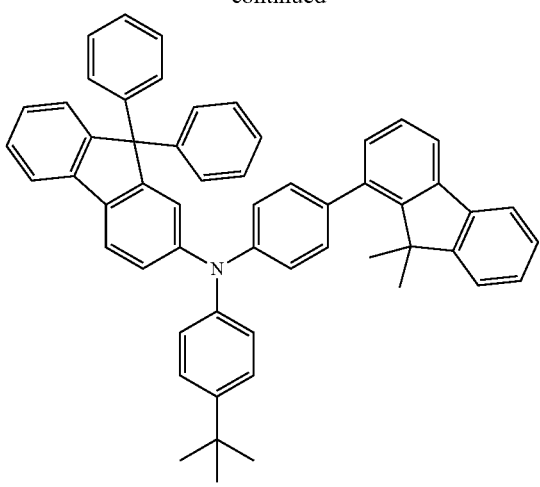
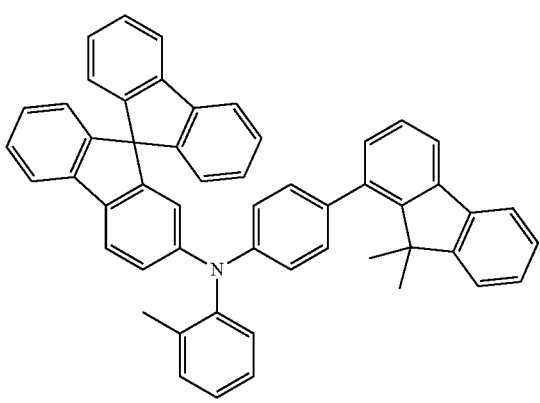
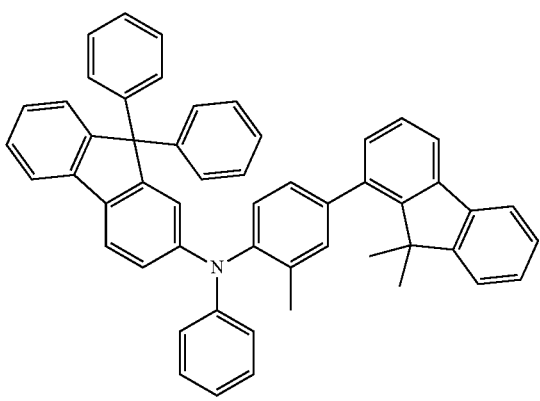
84
-continued
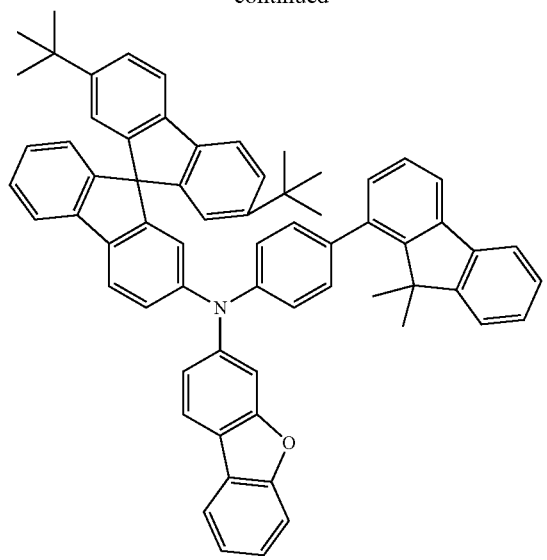
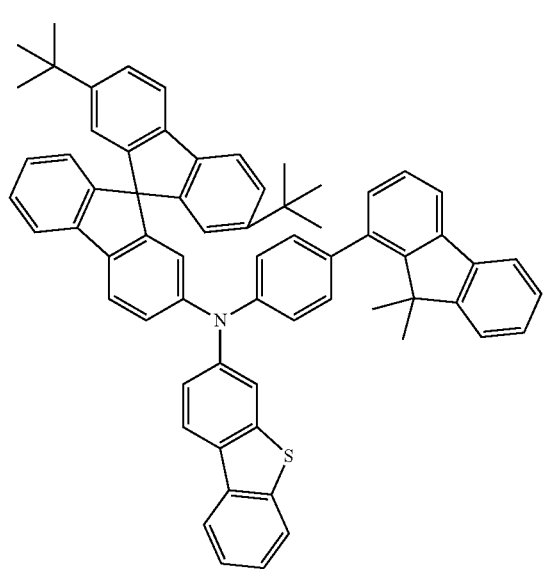
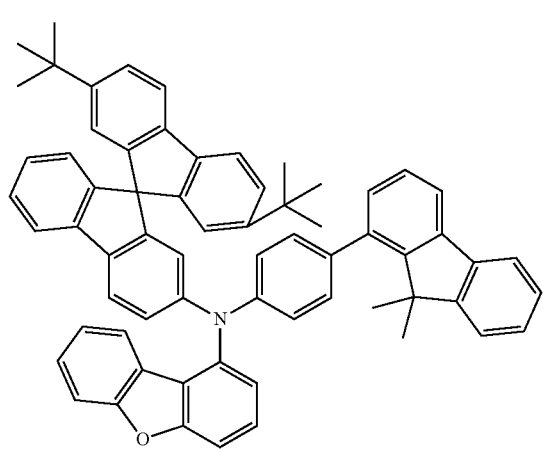

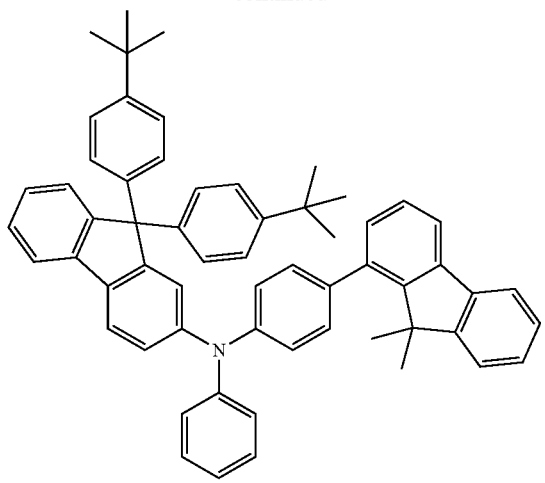
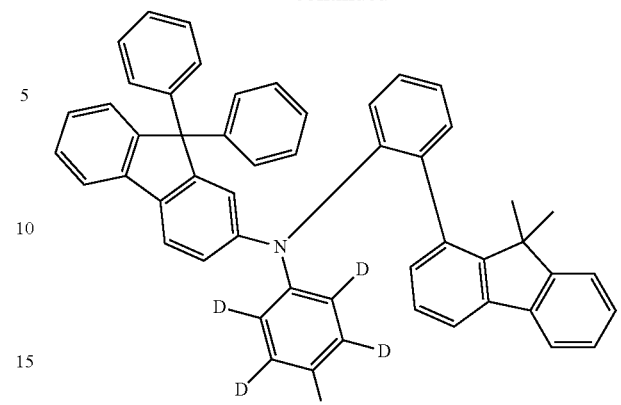
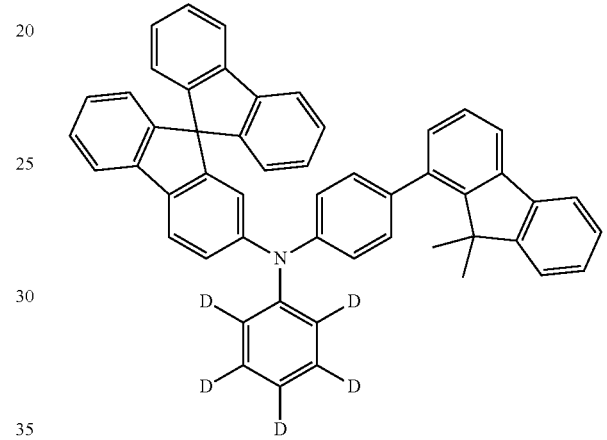
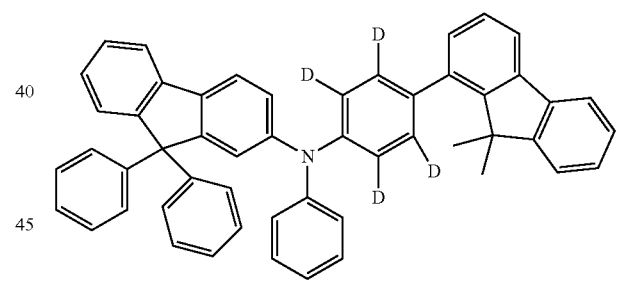
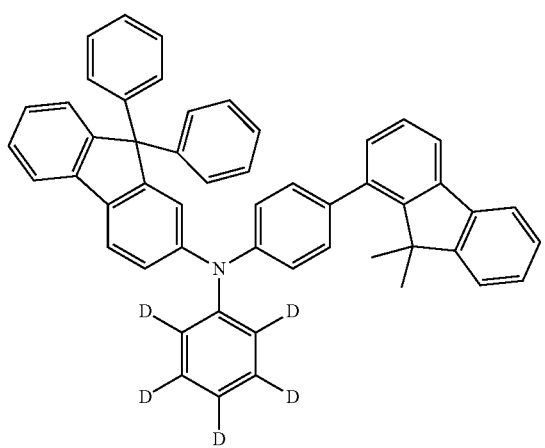
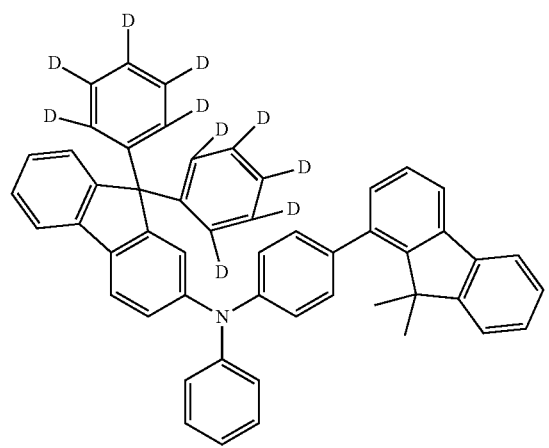

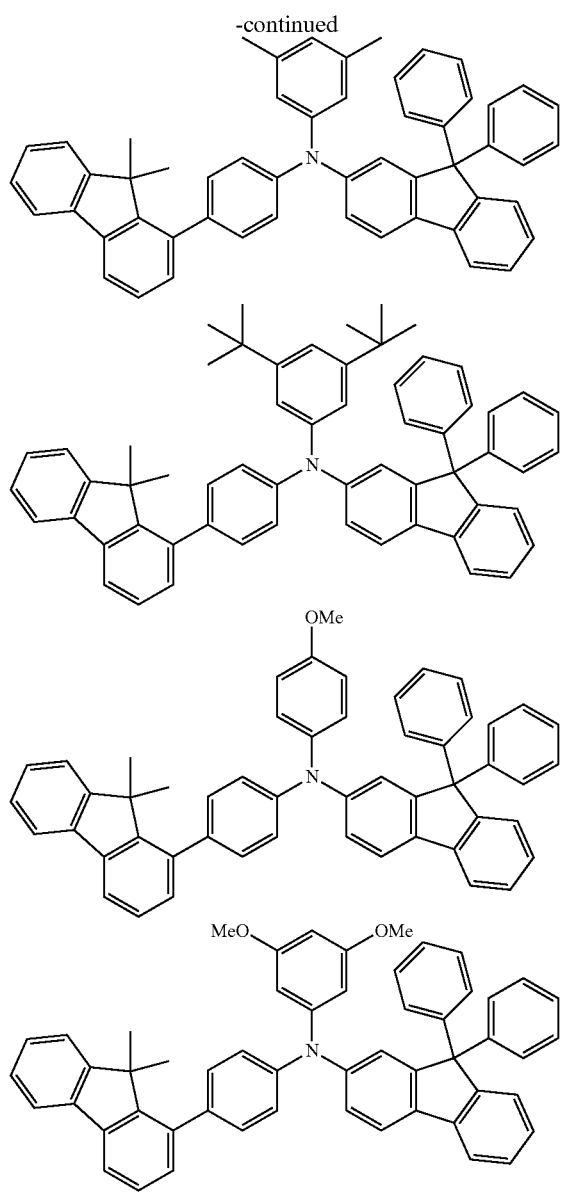

Material for Organic EL Devices

The material for organic electroluminescent devices comprises the inventive compound. The content of the inventive compound in the material for organic electroluminescent devices is 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%). The material for organic electroluminescent devices is useful for the production of organic EL devices.

Organic EL Device

The organic EL device of the invention comprises an anode, a cathode, and an organic layer disposed between the anode and the cathode. The organic layer comprises a light emitting layer and at least one layer of the organic layer comprises the inventive compound.

Examples of the organic layer which comprises the inventive compound include a hole transporting region formed between an anode and a light emitting layer, such as a hole injecting layer, a hole transporting layer, an electron blocking layer, and an exciton blocking layer, a light emitting layer, a space layer, and an electron transporting region formed between a cathode and a light emitting layer, such as an electron injecting layer, an electron transporting layer, and a hole blocking layer, although not limited thereto. The inventive compound is used for the production of a fluorescent or phosphorescent EL device preferably as a material for a hole transporting region or a light emitting layer, more preferably as a material for a hole transporting region, still more preferably as a material for a hole injecting layer, a hole transporting layer, an electron blocking layer or an exciton blocking layer, and particularly preferably as a material for a hole injecting layer or a hole transporting layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to in this description is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a multi-layered structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer/Electron transporting layer(/Electron injecting layer);

(b) (Hole injecting layer/)Hole transporting layer/Phosphorescent emitting layer/Electron transporting layer(/Electron injecting layer);

(c) (Hole injecting layer/)Hole transporting layer/First fluorescent emitting layer/Second fluorescent emitting layer/Electron transporting layer(/Electron injecting layer);

(d) (Hole injecting layer/)Hole transporting layer/First phosphorescent emitting layer/Second phosphorescent emitting layer/Electron transporting layer(/Electron injecting layer);

(e) (Hole injecting layer/)Hole transporting layer/Phosphorescent emitting layer/Space layer/Fluorescent emitting layer/Electron transporting layer(/Electron injecting layer);

(f) (Hole injecting layer/)Hole transporting layer/First phosphorescent emitting layer/Second phosphorescent emitting layer/Space layer/Fluorescent emitting layer/Electron transporting layer(/Electron injecting layer);

(g) (Hole injecting layer/)Hole transporting layer/First phosphorescent emitting layer/Space layer/Second phosphorescent emitting layer/Space layer/Fluorescent emitting layer/Electron transporting layer(/Electron injecting layer);

(h) (Hole injecting layer/)Hole transporting layer/Phosphorescent emitting layer/Space layer/First fluorescent emitting layer/Second fluorescent emitting layer/Electron transporting layer(/Electron injecting layer);

(i) (Hole injecting layer/)Hole transporting layer/Electron blocking layer/Fluorescent emitting layer/Electron transporting layer(/Electron injecting layer);
(j) (Hole injecting layer/)Hole transporting layer/Electron blocking layer/Phosphorescent emitting layer/Electron transporting layer (/Electron injecting layer);
(k) (Hole injecting layer/)Hole transporting layer/Exciton blocking layer/Fluorescent emitting layer/Electron transporting layer(/Electron injecting layer);
(l) (Hole injecting layer/)Hole transporting layer/Exciton blocking layer/Phosphorescent emitting layer/Electron transporting layer (/Electron injecting layer);
(m) (Hole injecting layer/)First hole transporting layer/Second hole transporting layer/Fluorescent emitting layer/Electron transporting layer(/Electron injecting layer);
(n) (Hole injecting layer/)First hole transporting layer/Second hole transporting layer/Phosphorescent emitting layer/Electron transporting layer (/Electron injecting layer);
(o) (Hole injecting layer/)First hole transporting layer/Second hole transporting layer/Fluorescent emitting layer/First electron transporting layer/Second electron transporting layer(/Electron injecting layer);
(p) (Hole injecting layer/)First hole transporting layer/Second hole transporting layer/Phosphorescent emitting layer/First electron transporting layer/Second electron transporting layer(/Electron injecting layer);
(q) (Hole injecting layer/)Hole transporting layer/Fluorescent emitting layer/Hole blocking layer/Electron transporting layer(/Electron injecting layer);
(r) (Hole injecting layer/)Hole transporting layer/Phosphorescent emitting layer/Hole blocking layer/Electron transporting layer(/Electron injecting layer);
(s) (Hole injecting layer/)Hole transporting layer/Fluorescent emitting layer/Exciton blocking layer/Electron transporting layer(/Electron injecting layer); and
(t) (Hole injecting layer/)Hole transporting layer/Phosphorescent emitting layer/Exciton blocking layer/Electron transporting layer(/Electron injecting layer).

The emission colors of phosphorescent emitting layers or fluorescent emitting layers may be different. For example, the layered structure of the emission unit (f) may be (Hole injecting layer)/Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may use a known material configuration in which electrons are supplied to the first emission unit and holes are supplied to the second emission unit.

FIG. 1 is a schematic illustration showing the structure of an example of the organic EL device of the invention, wherein an organic EL device 1 comprises a substrate 2, an anode 3, a cathode 4, and an emission unit 10 disposed between the anode 3 and the cathode 4. The emission unit 10 comprises a light emitting layer 5. A hole transporting region 6 (for example, a hole injecting layer or a hole transporting layer) is disposed between the light emitting layer 5 and the anode 3, and an electron transporting region 7 (for example, an electron injecting layer or an electron transporting layer) is disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

Figure 2:
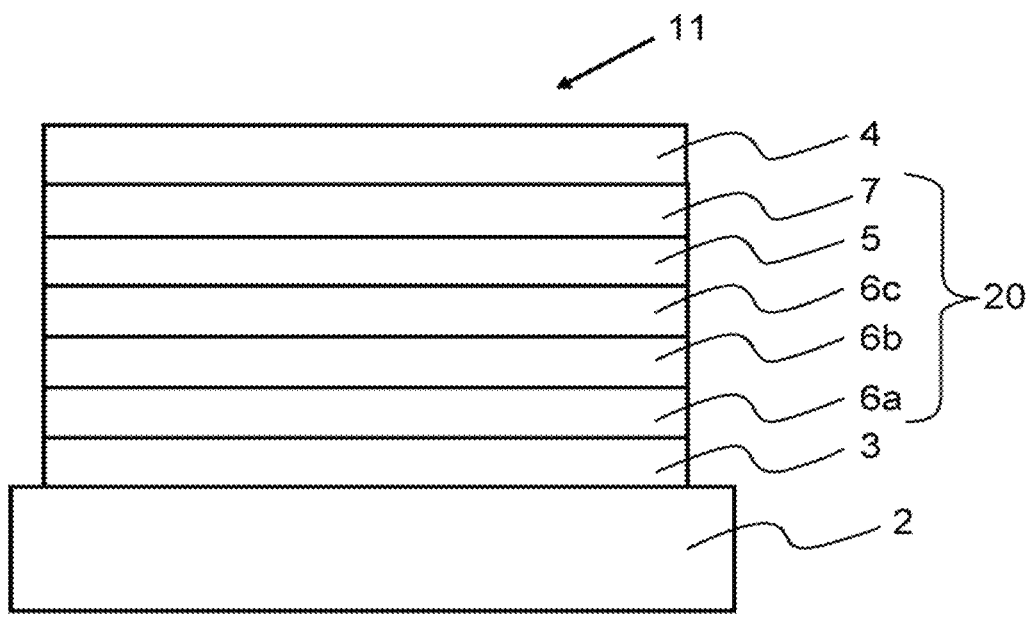
FIG. 2 is a schematic view showing another example of a layered configuration of an organic EL device of an embodiment of the invention.

FIG. 2 is a schematic illustration showing the structure of another example of the organic EL device of the present invention, wherein an organic EL device 11 comprises a substrate 2, an anode 3, a cathode 4, and an emission unit 20 disposed between the anode 3 and the cathode 5. The emission unit 20 comprises a light emitting layer 4. The hole transporting region disposed between the anode 3 and the light emitting layer 5 is formed by a hole transporting layer 6a, a first hole transporting layer 6b and a second hole transporting layer 6c. The electron transporting region disposed between the light emitting layer 5 and the cathode 4 is formed by an electron transporting layer 7.

In the present invention, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the organic EL device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode formed on the substrate is preferably made from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (w), chromium (Cr), molybdenum (Mo), iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally used as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium (Eu) and ytterbium (Yb), and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material) and formed between an anode and a light emitting layer or between an anode and a hole transporting layer, if present. The inventive compound may be used in the hole injecting layer.

Examples of the hole injecting material except the inventive compound include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following aromatic amine compounds, which are a low-molecular organic compound, are also usable as the hole injecting layer material: 4,4',4''-tris(N,N-diphenylamino)triphenylamine (TDATA), 4,4',4''-tris[N-(3-methylphenyl)-N-phenylamine]triphenylamine (MTDATA), 4,4'-bis[N-(4-diphenylaminophenyl)-N-phenylamine]biphenyl (DPAB), 4,4'-bis(N-{4-[N'-(3-methylphenyl)-N'-phenylamine]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). A macromolecular compound doped with an acid, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used:

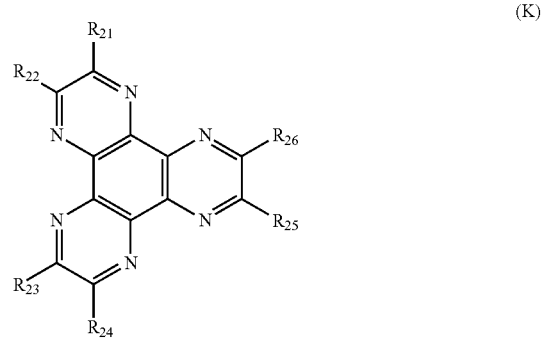

(K)

wherein:

$R_{21}$ to $R_{26}$ are each independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material) and formed between an anode and a light emitting layer or between a hole injecting layer, if present, and a light emitting layer. The inventive compound is preferably used in a hole transporting layer alone or in combination with the compound described below.

The hole transporting layer may be a single layer or a multi-layer of two or more layers. For example, the hole transporting layer may be a two-layered structure comprising a first hole transporting layer (anode side) and a second hole transporting layer (cathode side). In an embodiment of the invention, a hole transporting layer of a single-layered structure is preferably in contact with a light emitting layer and a hole transporting layer in a multi-layered structure which is closest to a cathode, for example, the second hole transporting layer in the two-layered structure mentioned above, is preferably in contact with a light emitting layer. In another embodiment of the invention, an electron blocking layer mentioned below may be disposed between the light emitting layer and the hole transporting layer of the single-layered structure or between the light emitting layer and the hole transporting layer in the multi-layered structure which is closest to the light emitting layer.

In the two-layered structure of the hole transporting layer, the inventive compound may be included in one or both of the first hole transporting layer and the second hole transporting layer.

In an embodiment of the invention, the inventive compound is preferably used only in the first hole transporting layer. In another embodiment, the inventive compound is preferably used only in the second hole transporting layer. In still another embodiment, the inventive compound is preferably used in both the first hole transporting layer and the second hole transporting layer.

Examples of the hole transporting material other than the inventive compound includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluoren-9-yl)triphenylamine (BAFLP), 4,4'-bis[N-(9,9-dimethylfluorene-2-yl)-N-phenylamino]biphenyl (DFLDPBi), 4,4',4''-tris(N,N-diphenylamino)triphenylamine (TDATA), 4,4',4''-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ cm$^2$/Vs or more.

Examples of the carbazole derivative include 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA).

Examples of the anthracene derivative include 2-t-butyl-9,10-di(2-naphthyl) anthracene (t-BuDNA), 9,10-di(2-naphthyl)anthracene (DNA), and 9,10-diphenylanthracene (DPAnth).

In addition, a macromolecular compound, such as poly(N-vinylcarbazole) (PVK) and poly(4-vinyltriphenylamine) (PVTPA) are usable.

Compounds other than those mentioned above are also usable, if their hole transporting ability is higher than their electron transporting ability.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acaa)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoro acetonato](monophenanthroline) europium(III) (Eu(TTA)$_3$(Phen)), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The host material preferably has a lowest unoccupied molecular orbital level (LUMO level) higher than that of the dopant material and a highest occupied molecular orbital level (HOMO level) lower than that of the dopant material.

The host material may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a condensed aromatic compound, such as a carbazole derivative, an anthracene derivative, a phenanthrene derivative, a pyrene derivative, and a chrysene derivative; and (4) an aromatic amine compound, such as a triarylamine derivative and a condensed polycyclic aromatic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h] quinolinato)beryllium(II) (BeBq$_2$), bis(2-methyl-8-quinolinolato)(4-phenylphenolato)aluminum (III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4- biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a condensed aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-naphthyl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

In particular, as a host material for a blue fluorescent device, the following anthracene compound is preferably used.

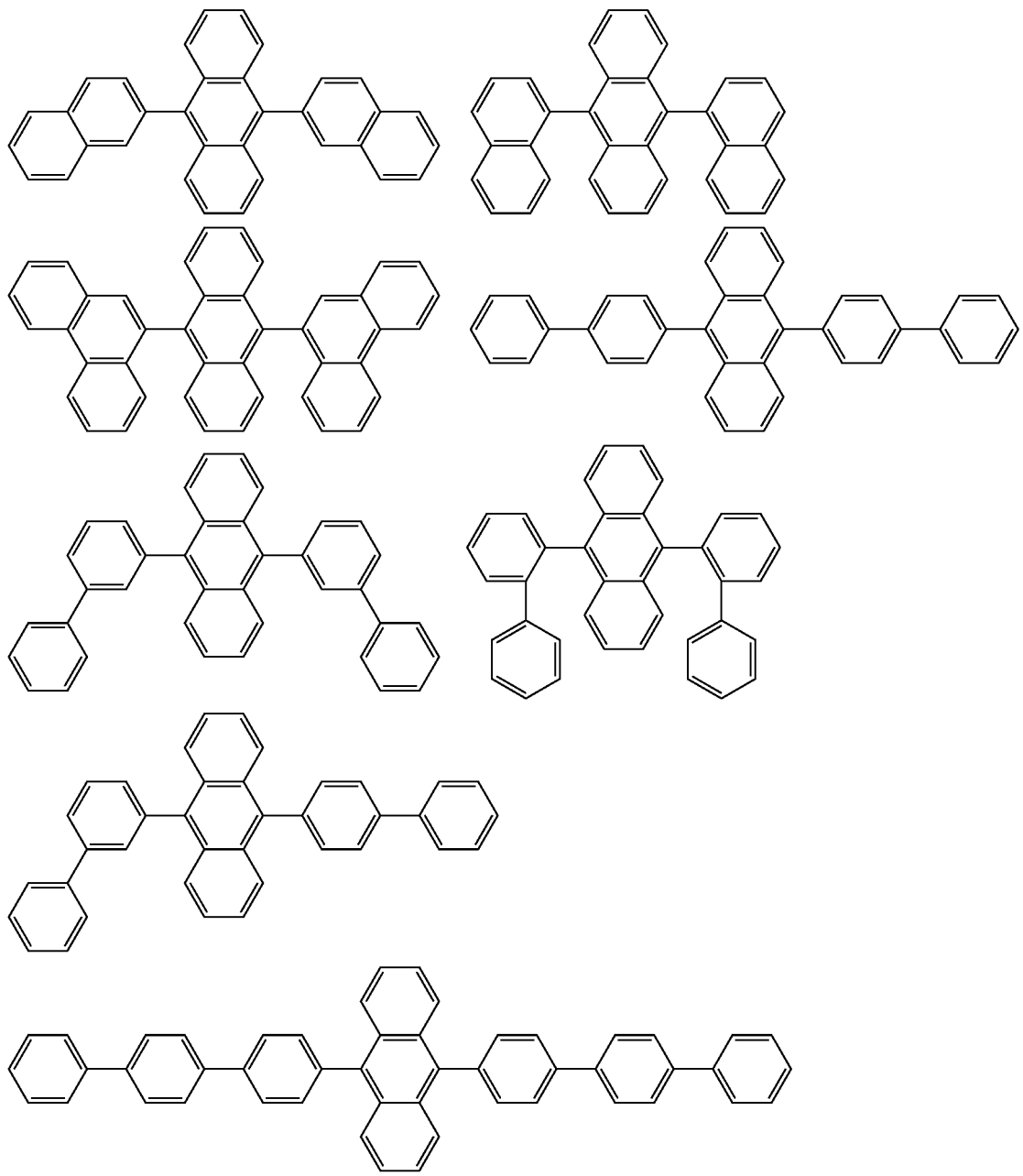

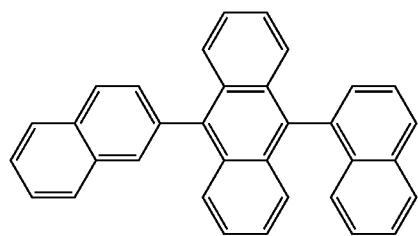
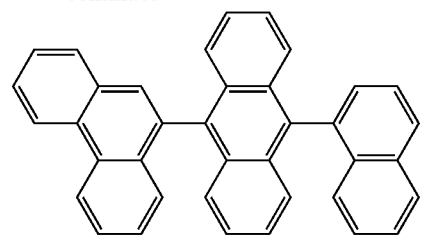
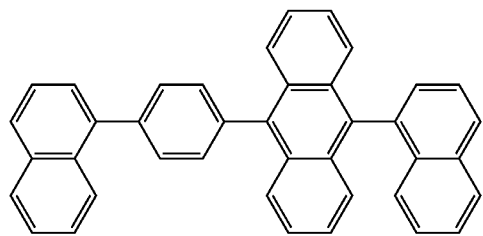
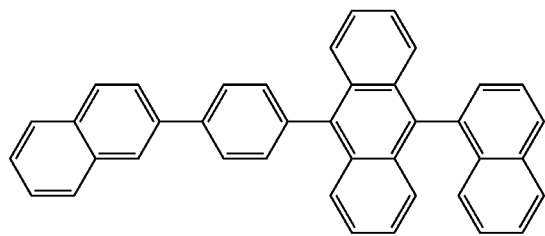
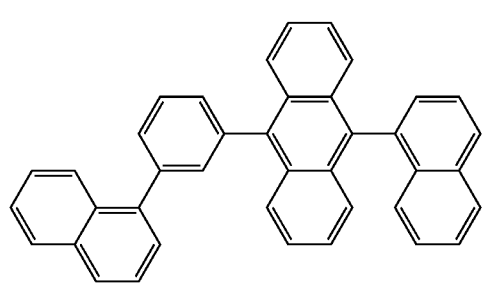
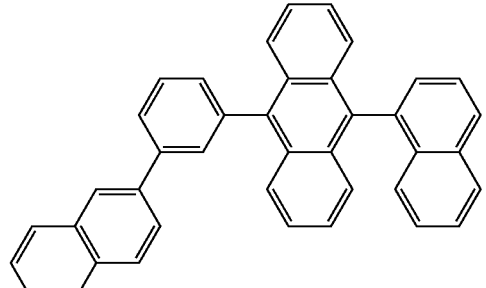
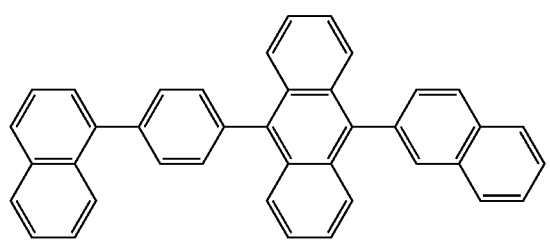
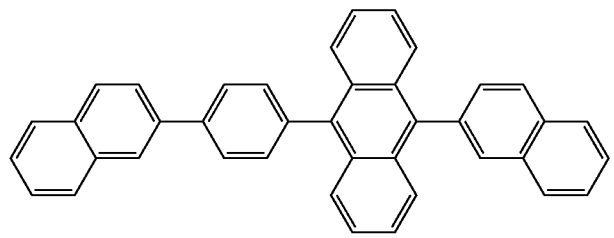
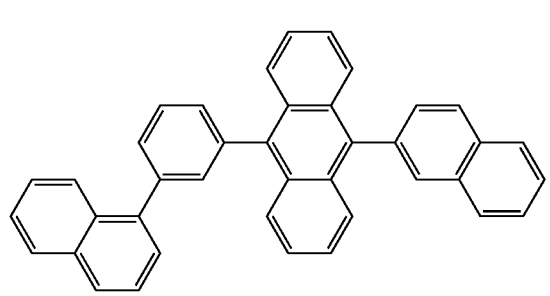
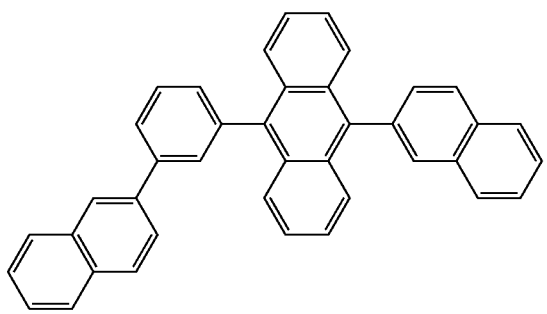

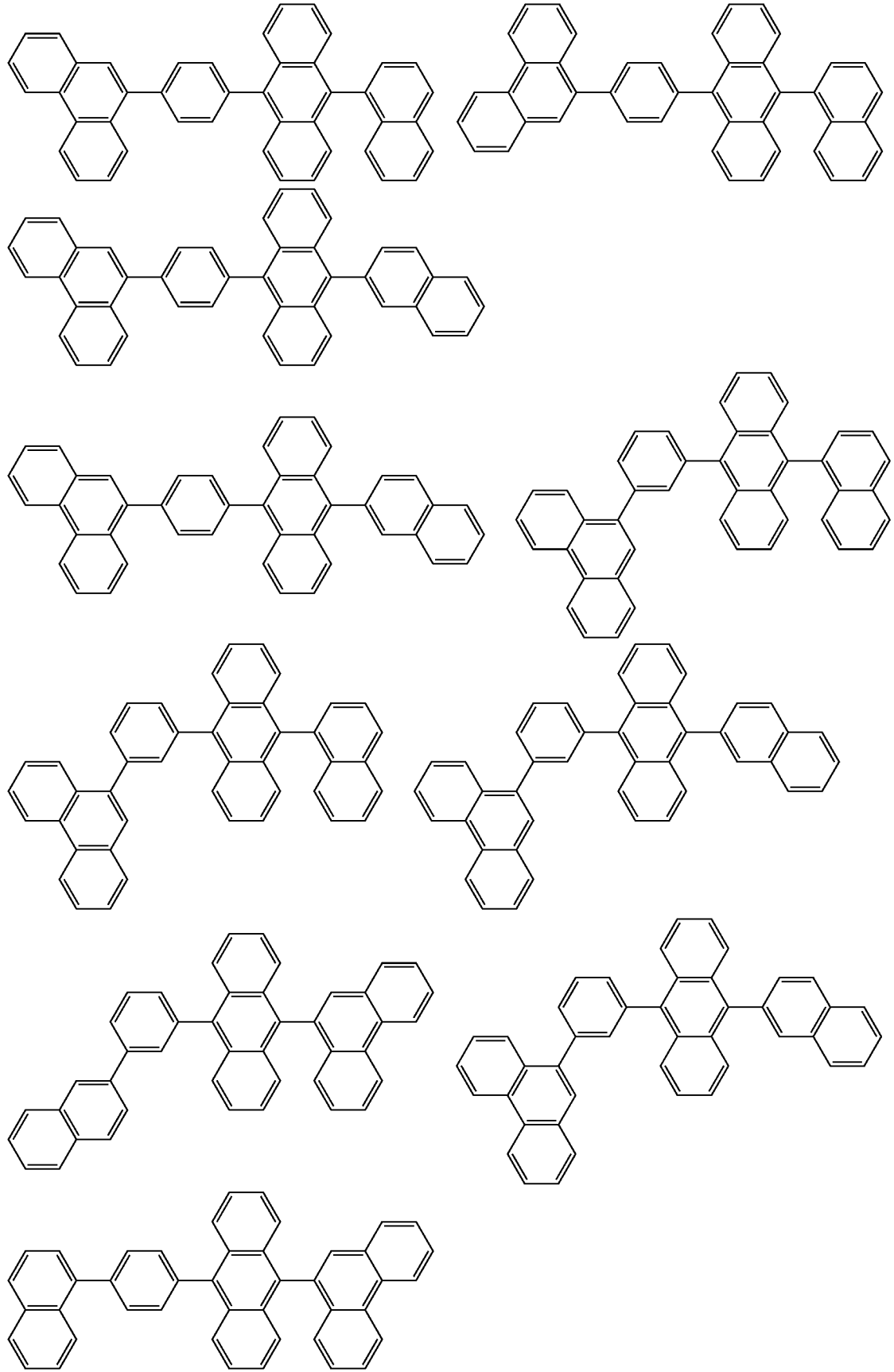

-continued
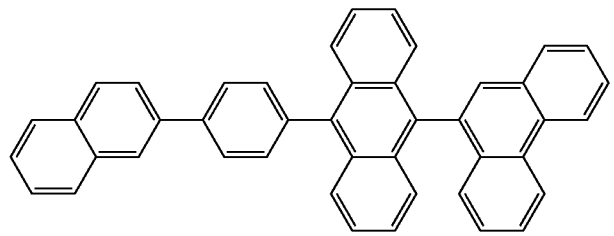
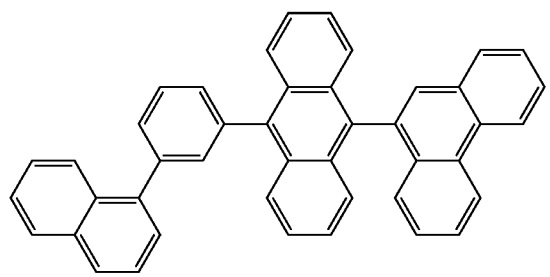
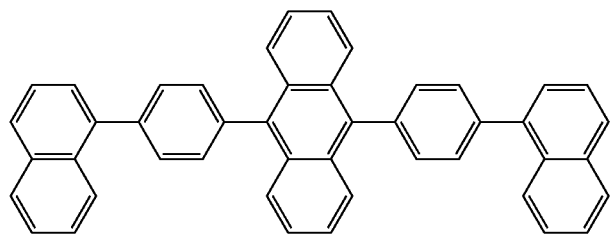
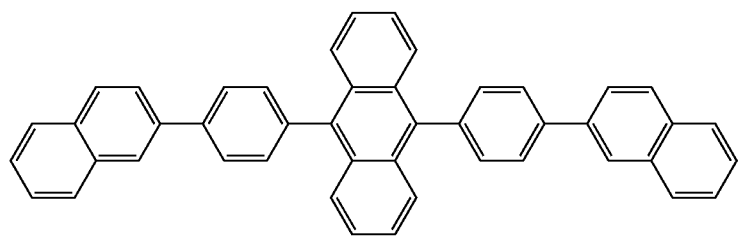
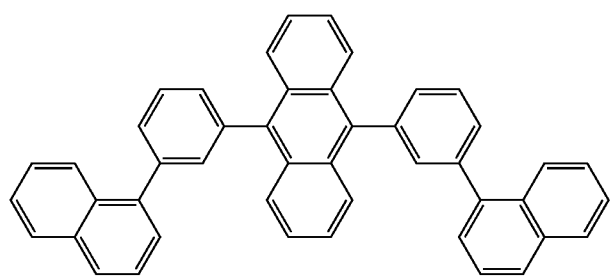
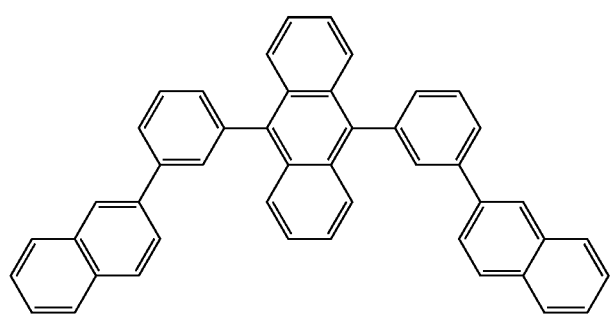

-continued
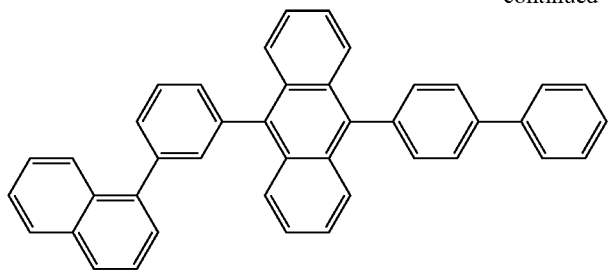
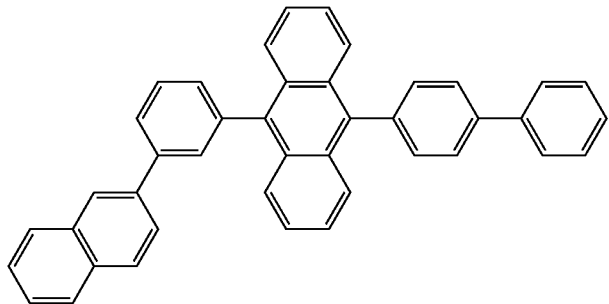
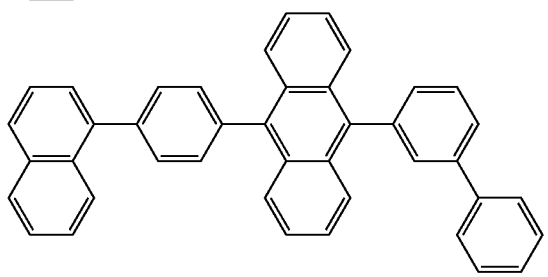
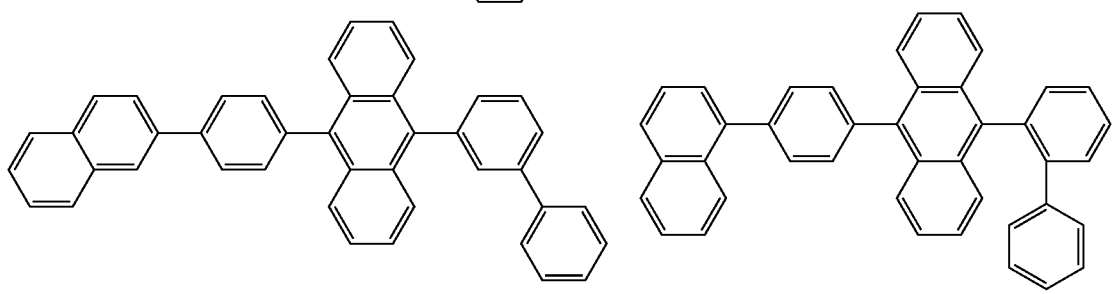
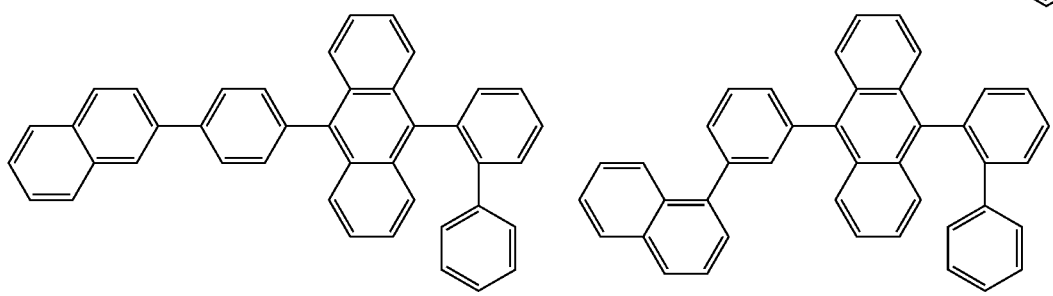
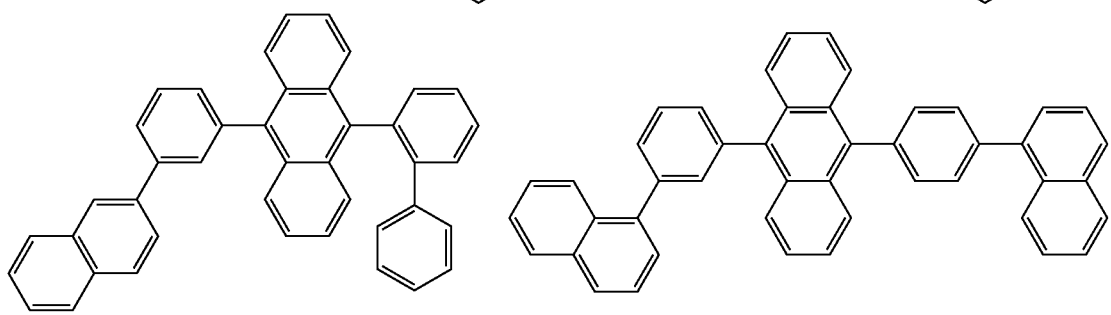

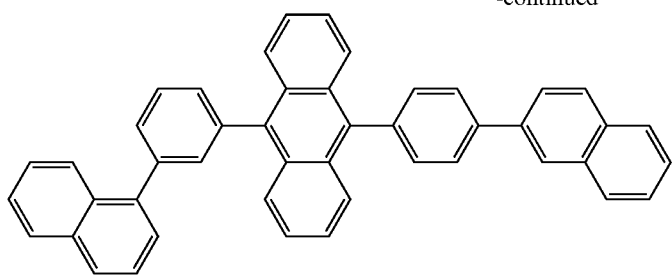
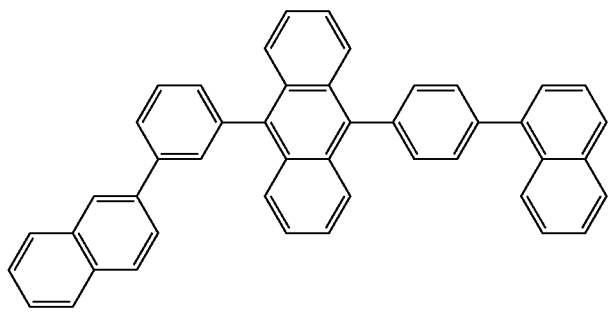
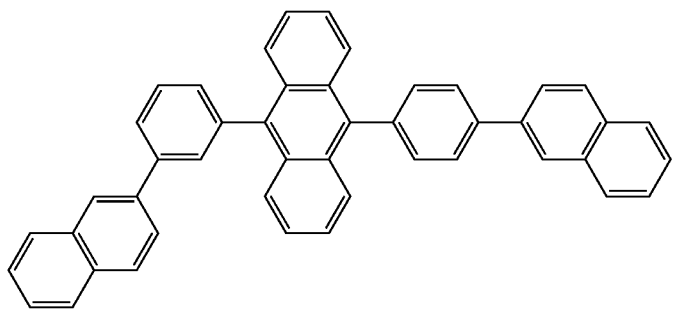
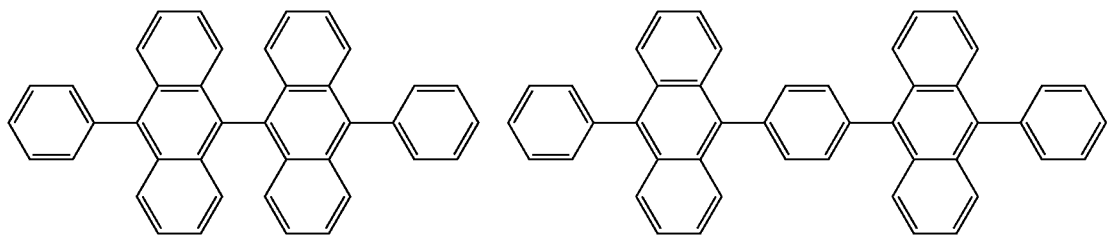
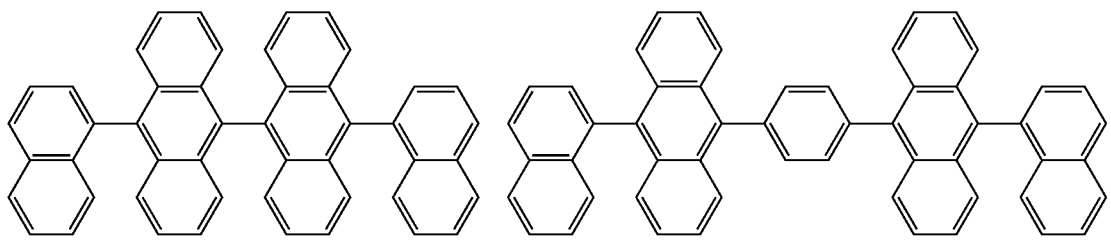
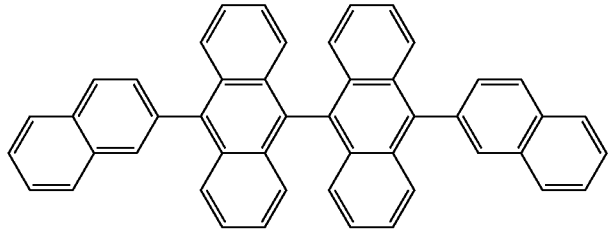

-continued
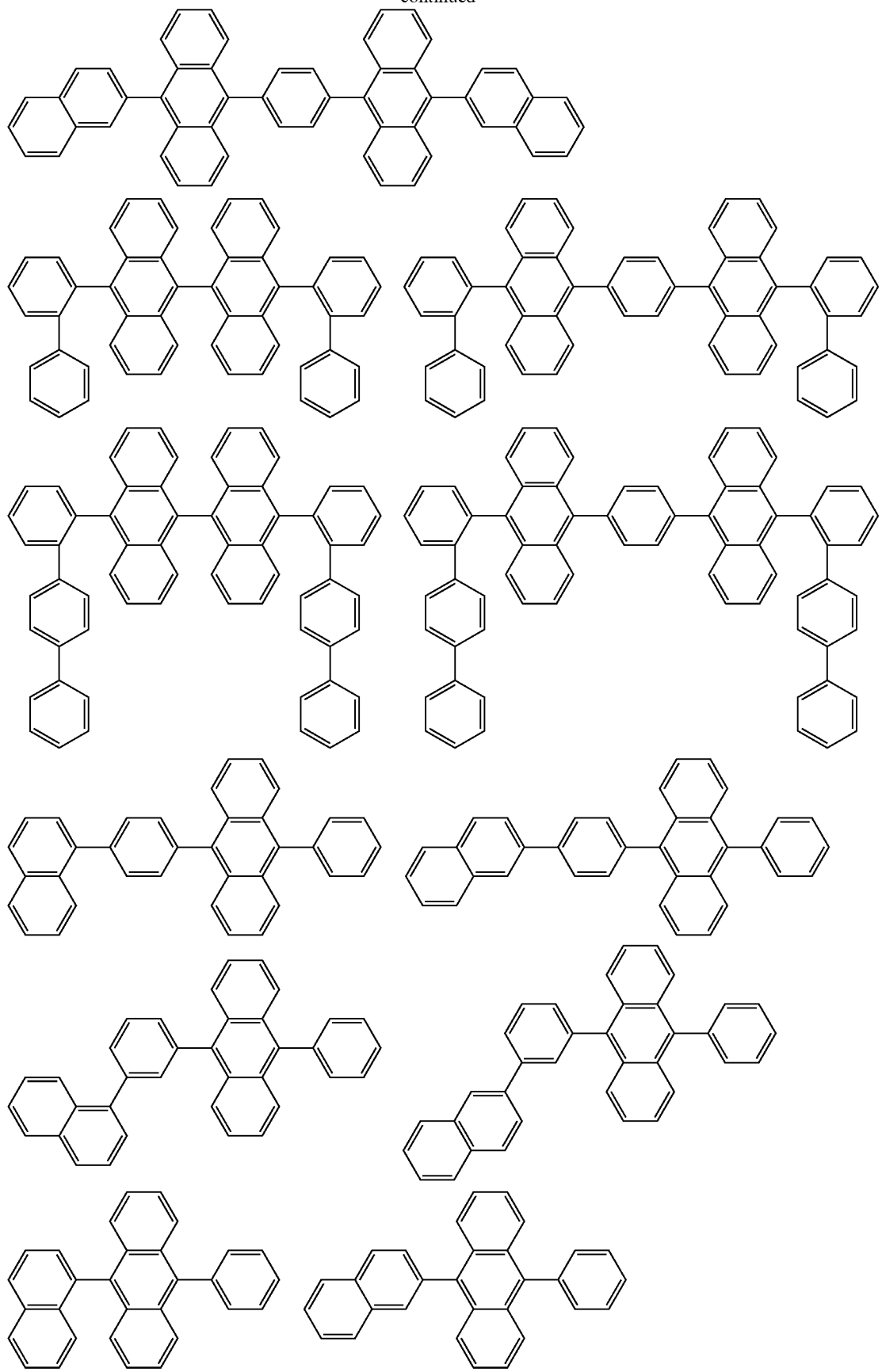

-continued
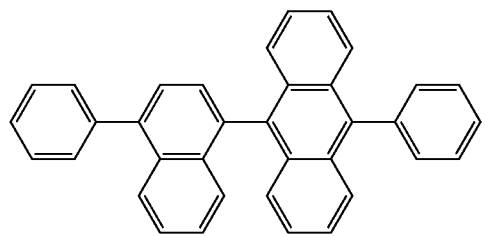
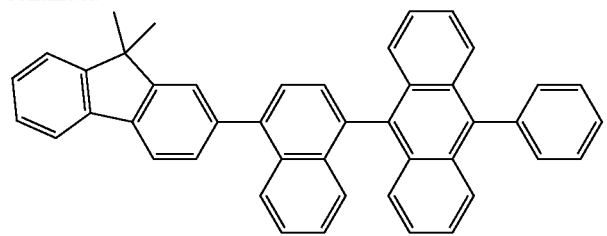
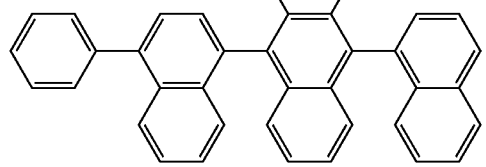
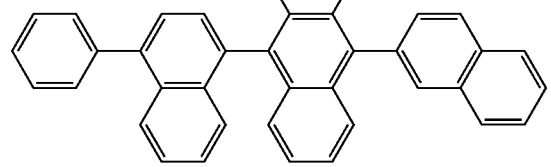
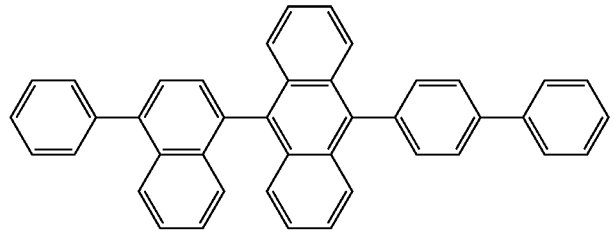
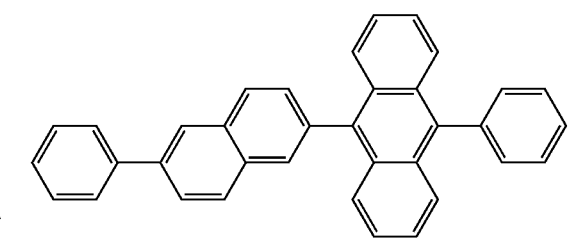
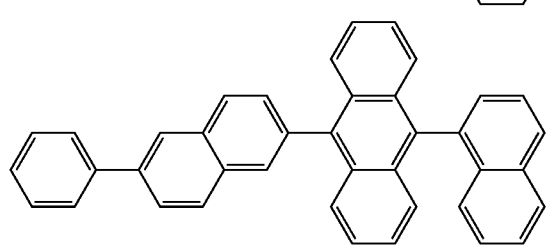
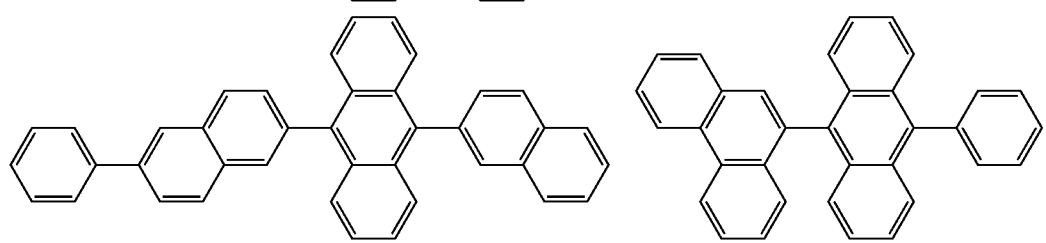
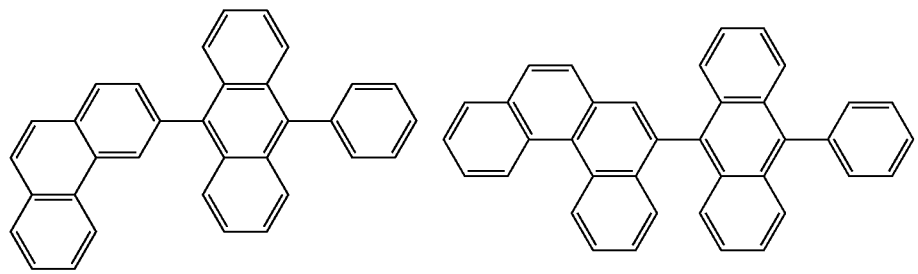

-continued
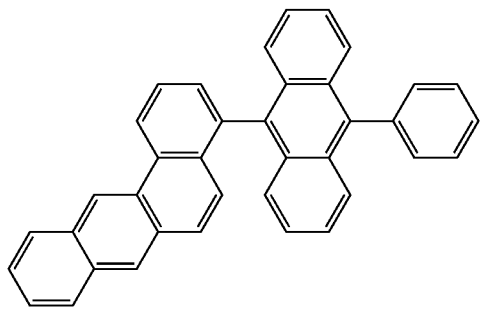
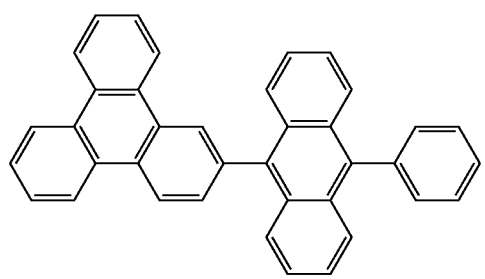
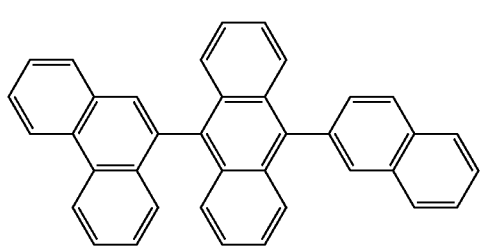
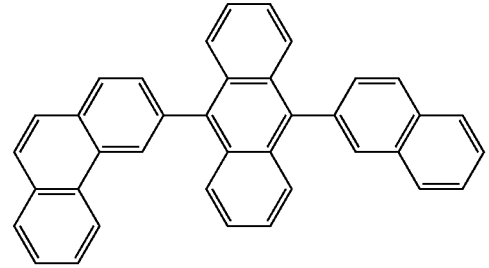
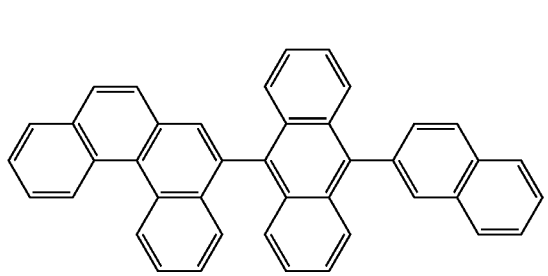
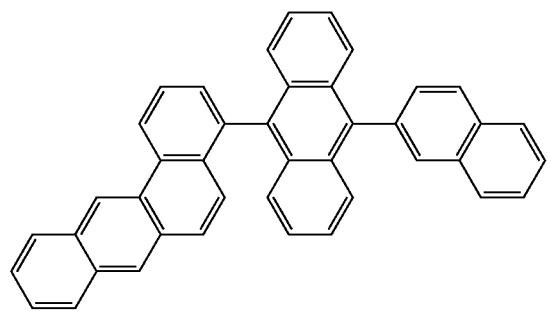
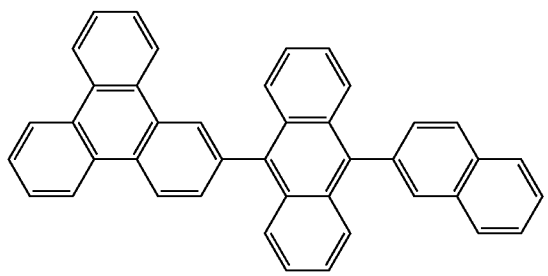
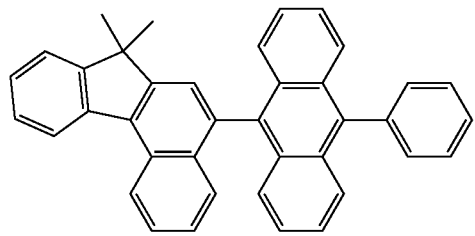
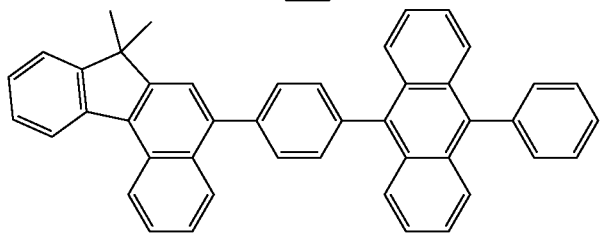
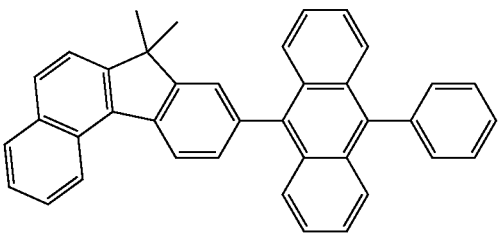
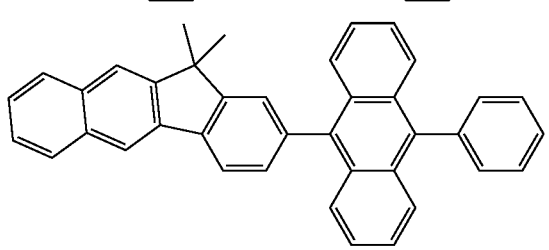
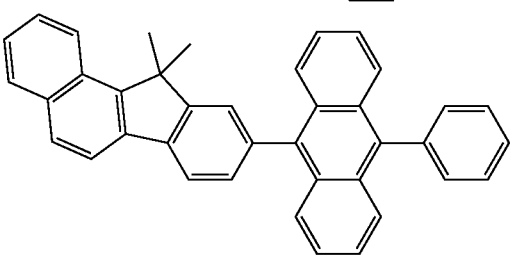

-continued
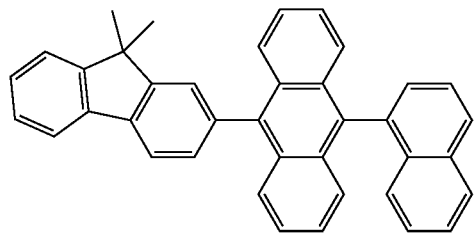
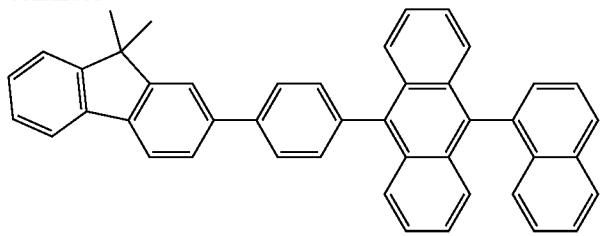
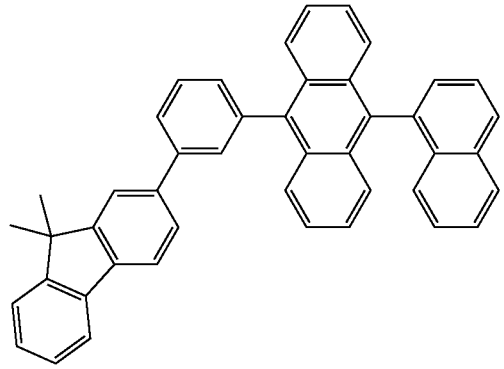
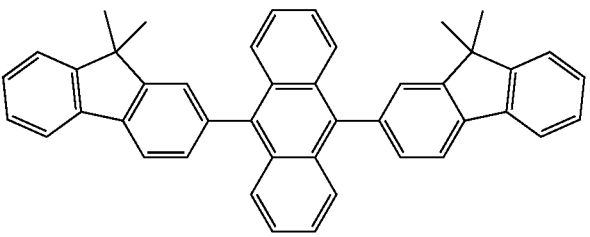
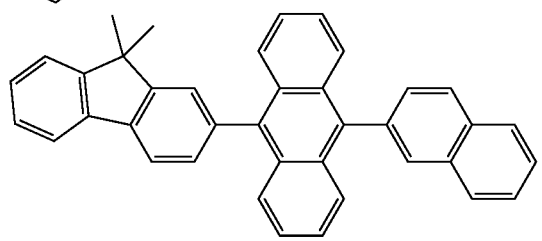
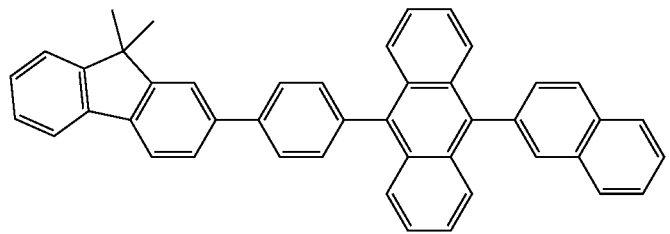
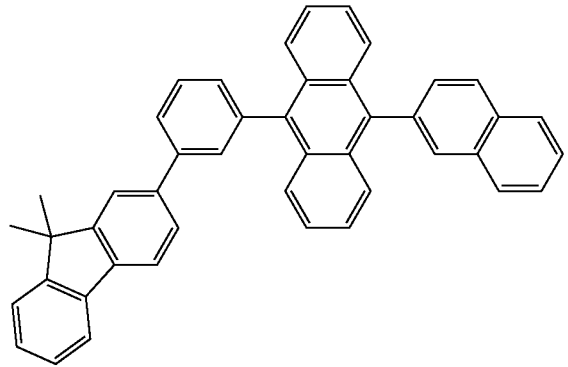
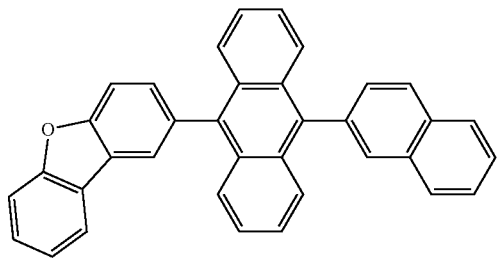
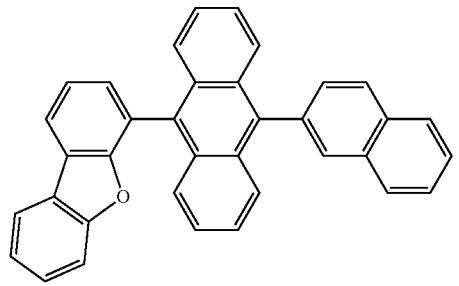
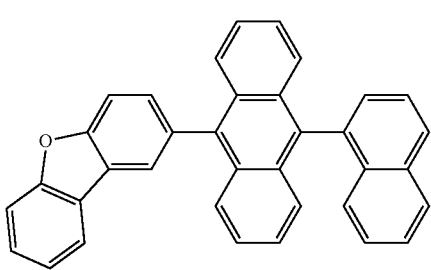

-continued
115
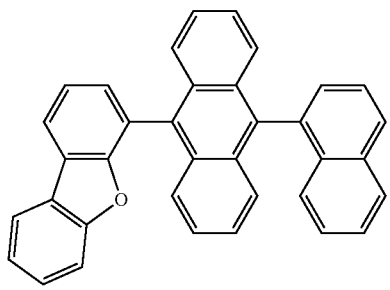
116
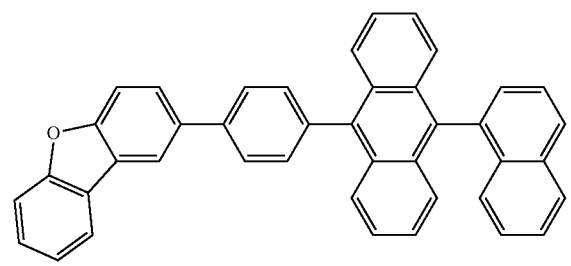
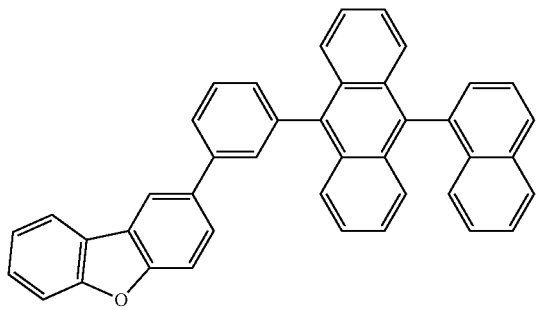
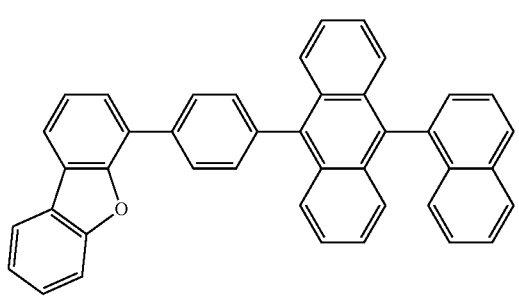
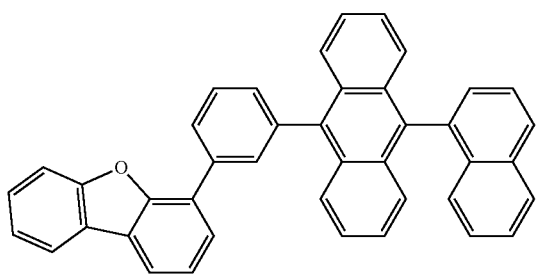
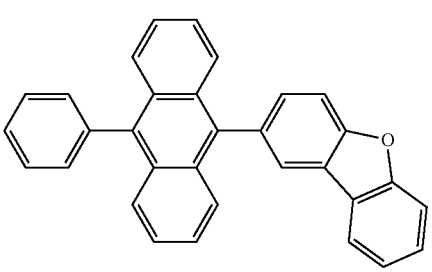
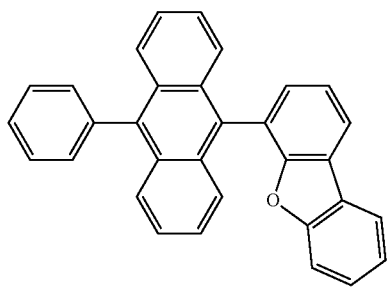
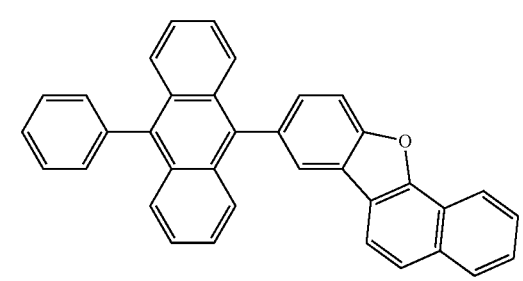
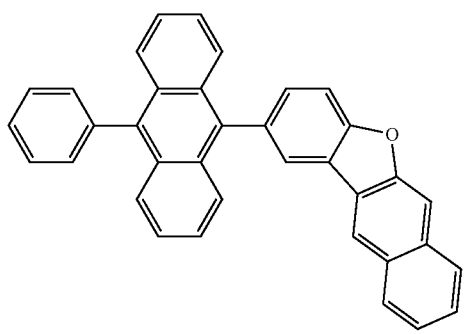
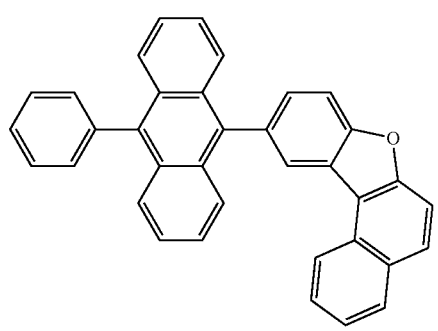

-continued
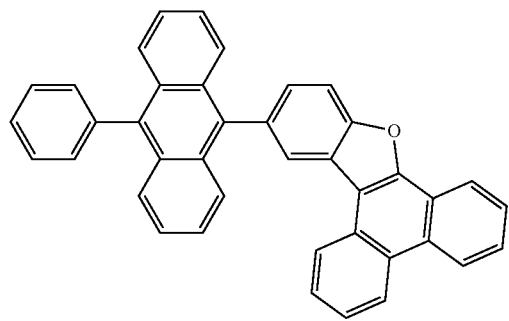
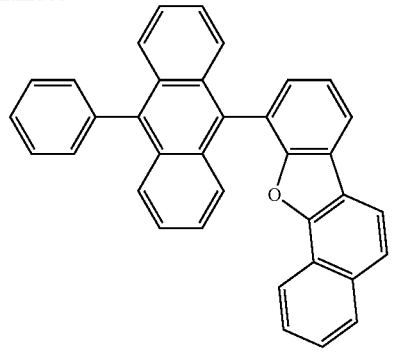
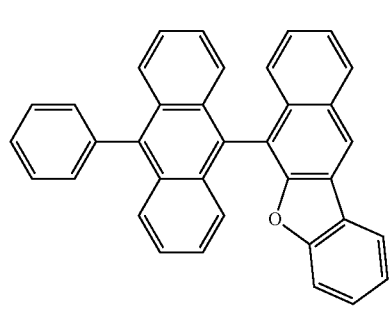
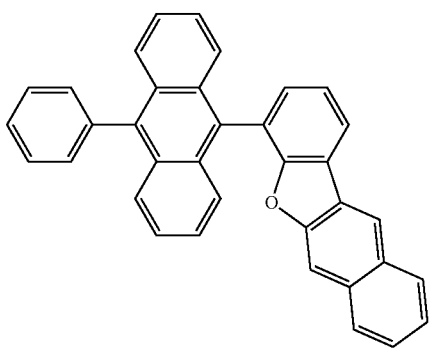
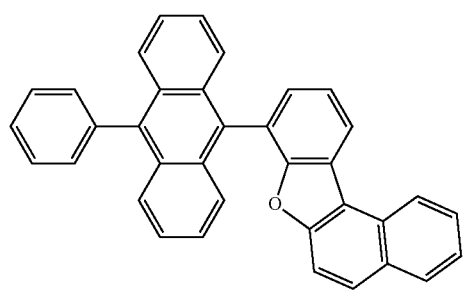
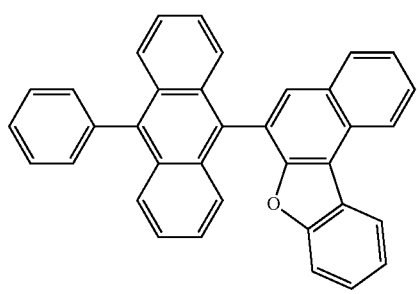
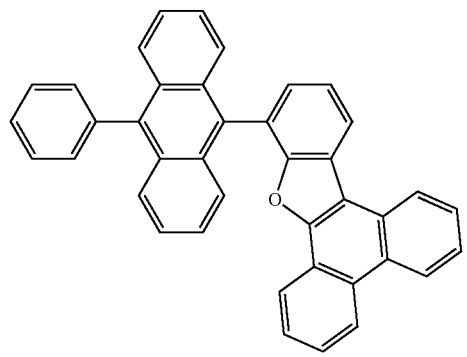
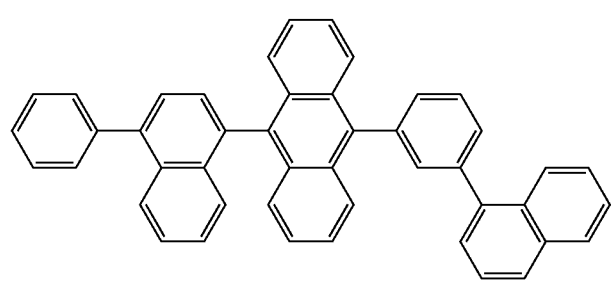
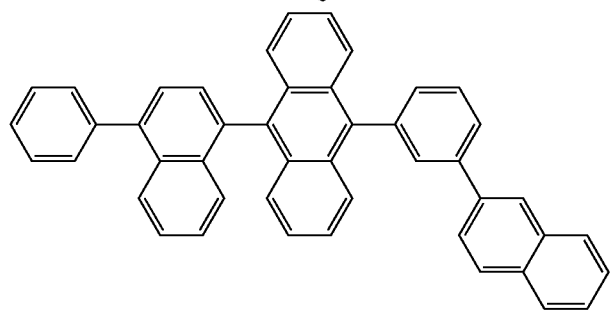

-continued
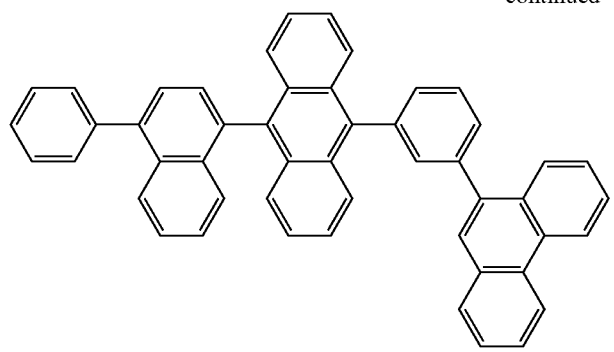
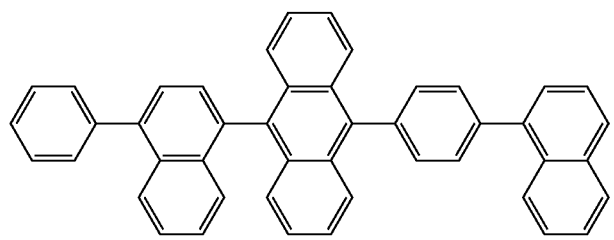
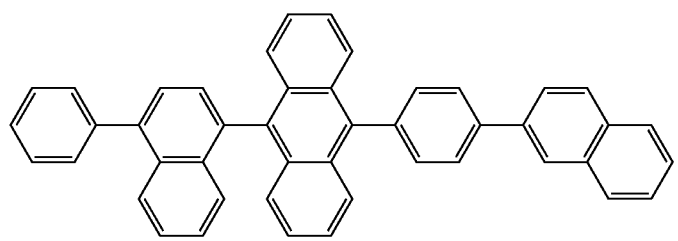
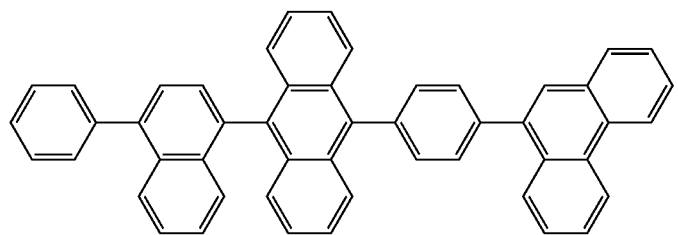
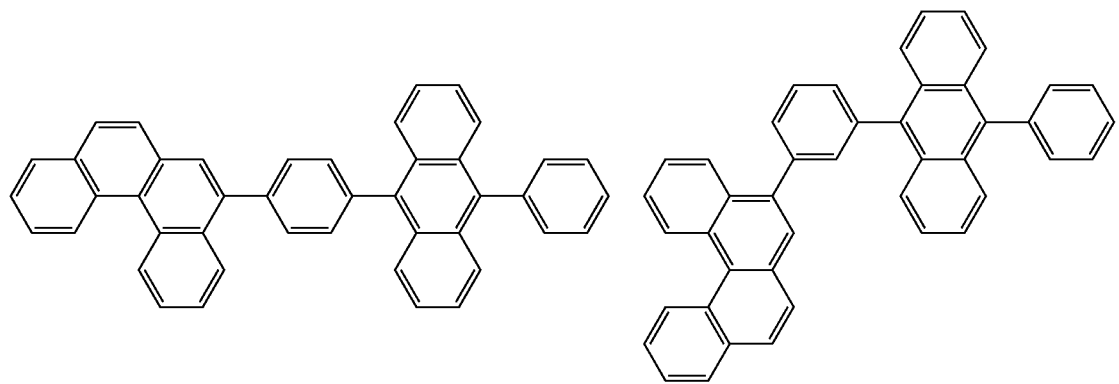

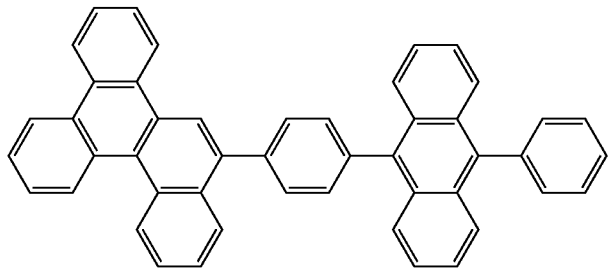

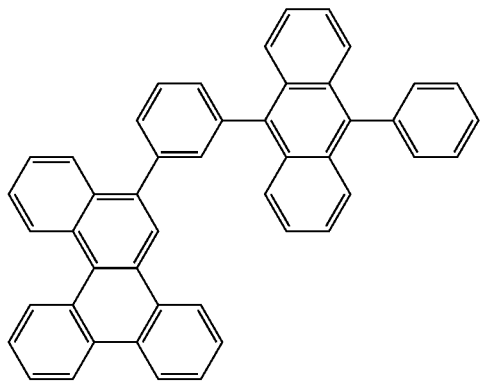

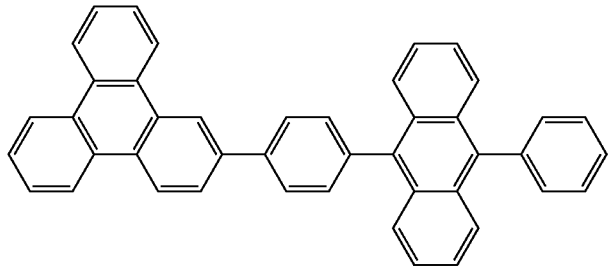

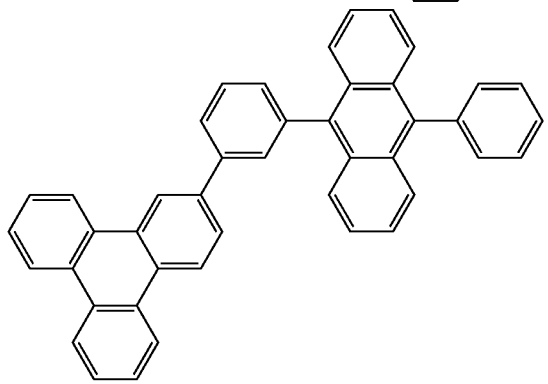

Electron Transporting Layer

The electron transporting layer comprises a material having a high electron transporting ability (electron transporting material) and formed between a light emitting layer and a cathode or between a light emitting layer and an electron injecting layer, if present.

The electron transporting layer may be a single layer or a multi-layer of two or more layers. For example, the electron transporting layer may be a two-layered structure comprising a first electron transporting layer (anode side) and a second electron transporting layer (cathode side). In an embodiment of the invention, an electron transporting layer of a single-layered structure is preferably in contact with a light emitting layer and an electron transporting layer in a multi-layered structure which is closest to an anode, for example, the first electron transporting layer in the two-layered structure mentioned above, is preferably in contact with a light emitting layer. In another embodiment of the invention, an hole blocking layer mentioned below may be disposed between the light emitting layer and the electron transporting layer of the single-layered structure or between the light emitting layer and the electron transporting layer in the multi-layered structure which is closest to the light emitting layer.

The electron transporting layer may be formed, for example, by
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato)aluminum (Almq$_3$), bis(10-hydroxybenzo[h]quinolinato)beryllium (BeBq$_2$), bis(2-methyl-8-quinolinolato)(4-phenylphenolato)aluminum (III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazol-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of $10^{-6}$ cm$^2$/Vs or more. Materials other than those mentioned above are also usable in the electron transporting layer if their electron transporting ability is higher than their hole transporting ability.

Electron Injecting Layer

The electron injecting layer is a layer comprising a material having a high electron injecting ability, for example, an alkali metal, such as lithium (Li), cesium (Cs), an alkaline earth metal, such as magnesium (Mg), calcium (Ca), and strontium (Sr), a rare earth metal, such as europium (Eu) and ytterbium (Yb), and a compound of these metals, such as an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. These compounds may be used in combination of two or more.

In addition, a material having an electron transporting ability which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the heteroaromatic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide—tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating layer formed of an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of stacked layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier (charge) balance. The space layer may be disposed between two or more phosphorescent emitting layers.

Since the space layer is disposed between the light emitting layers, a material having both the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and an exciton blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The exciton blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a dipping method, a spin coating method, a casting method, a bar coating method, and a roll coating method.

The thickness of each layer is not particularly limited and preferably 5 nm to 10 µm, more preferably 10 nm to 0.2 µm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Inventive compounds used in production of organic EL devices of the following Examples 1 to 6:

Compound 1

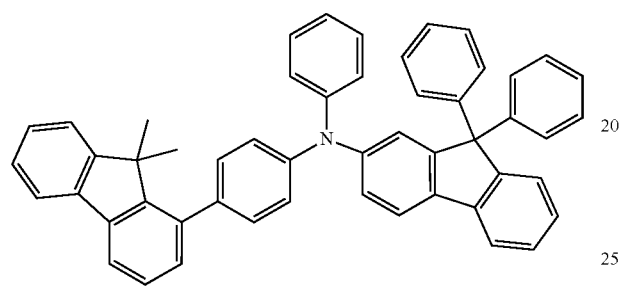

Compound 2

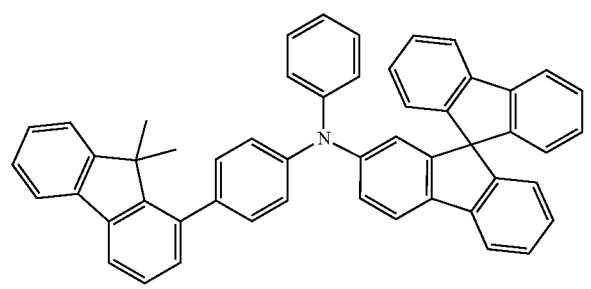

Compound 3

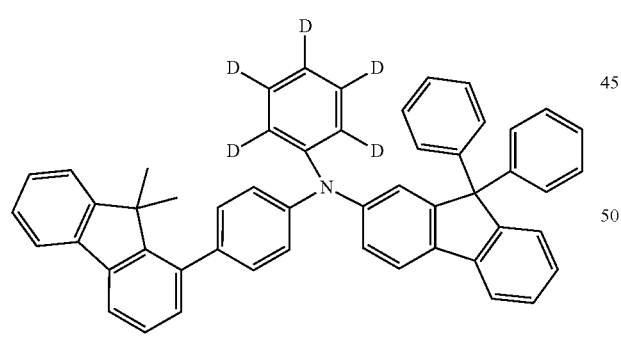

Compound 4

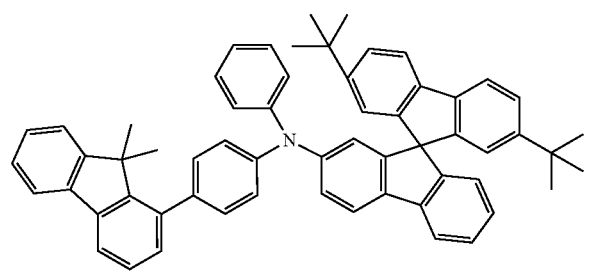

Compound 5

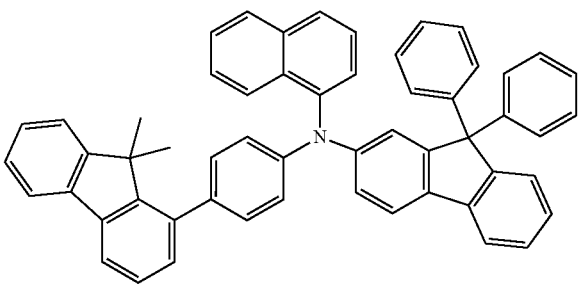

Comparative compounds used in production of organic EL devices of the following Comparative Examples 1 to 3:

Comparative Compound Ref-1

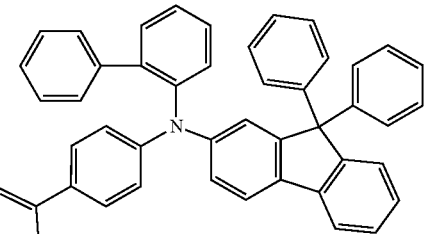

Comparative Compound Ref-2

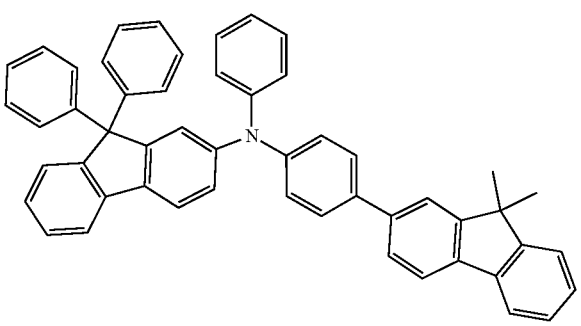

Comparative Compound Ref-3

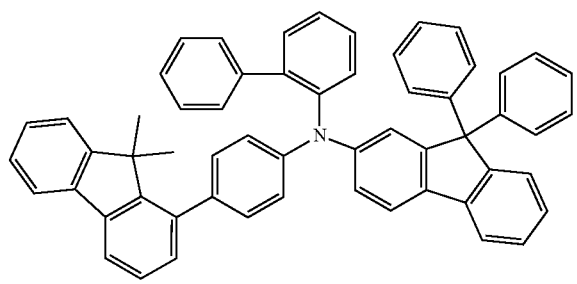

The comparative compound Ref-1 is a compound described in PTL 2 (page 37) and the compound B240 described in PTL 6.

The comparative compound Ref-3 is the compound A-38 described in PTL 3 (page 55).

Other compounds used in production of organic EL devices of the following Example 1 and the following Comparative Example 1:

HA

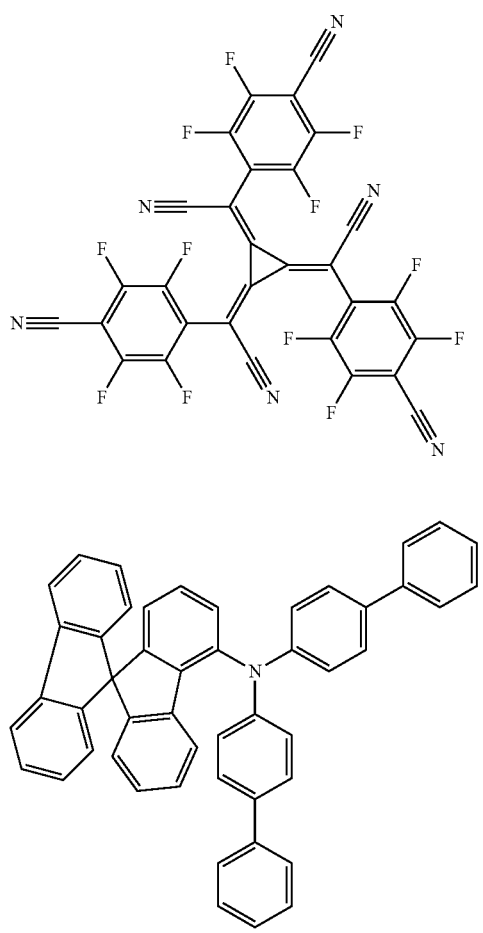

HT2

BH

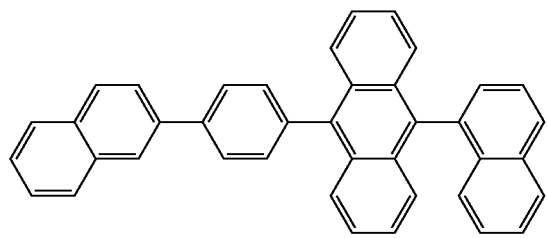

BD1

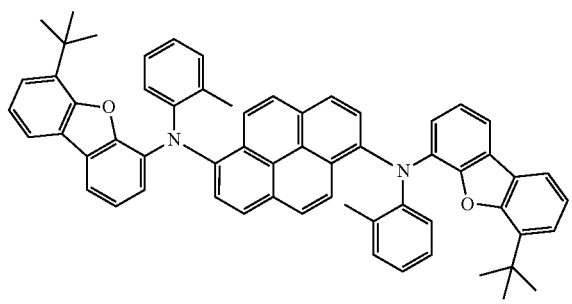

ET1

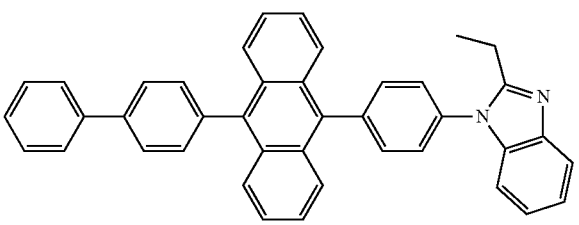

ET2

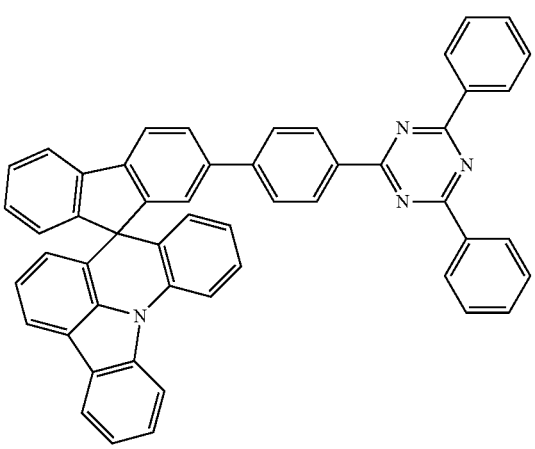

Other compounds used in production of organic EL devices of the following Examples 2 to 6 and the following Comparative Examples 2 and 3 (these are the same as those of the other compounds used in production of organic EL devices of Example 1 and Comparative Example 1 except that BD1 was changed to BD2):

BD2

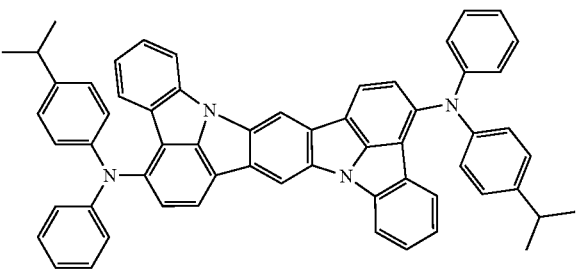

Compounds 6 to 15 synthesized in Synthesis Examples 6 to 15:

Compound 6

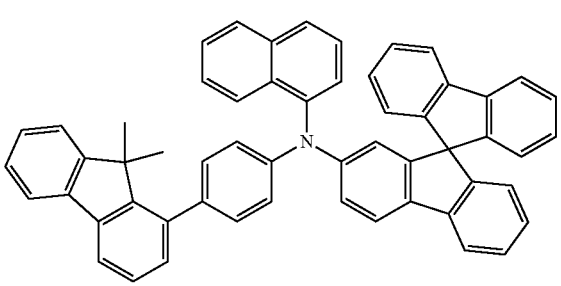

Compound 7
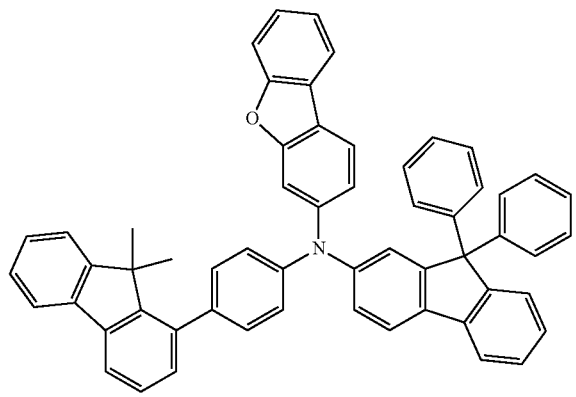
Compound 8
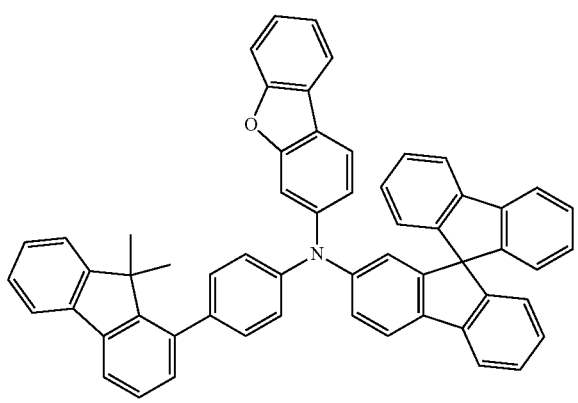
Compound 9
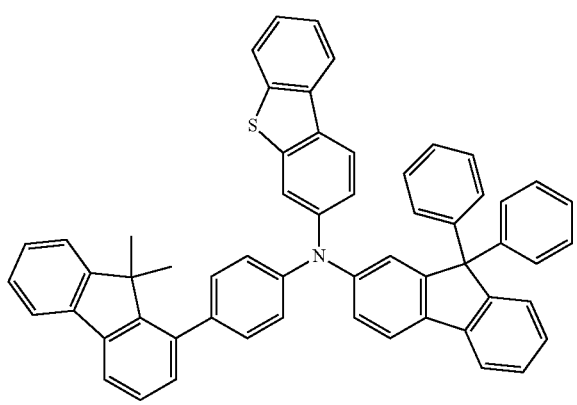
Compound 10
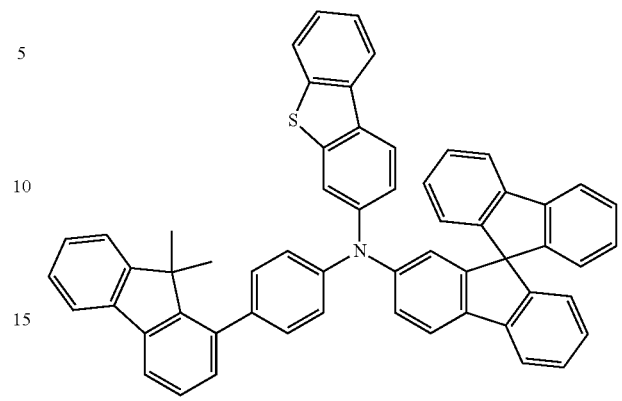
Compound 11
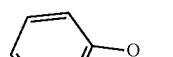
Compound 12
Compound 13
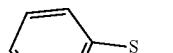

-continued

Compound 14

Compound 15

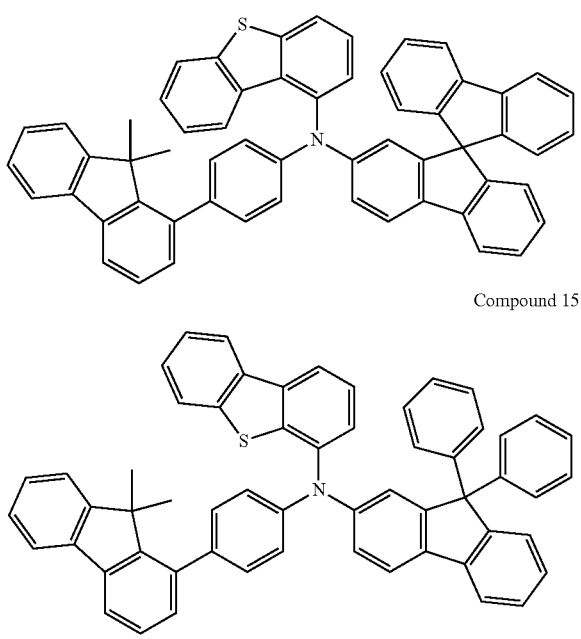

Each organic EL device was produced in the following manner and evaluated for EL device performance thereof.
Production of Organic EL Device Example 1

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode line was mounted to a substrate holder of a vacuum vapor deposition apparatus. First, the compound HT1 (compound 1) and the compound HA were vapor co-deposited on the surface having the transparent electrode line so as to cover the transparent electrode to form a hole injecting layer with a thickness of 10 nm. The ratio by mass of the compound HT1 to the compound HA was 85/15.

On the hole injecting layer, the compound HT1 (compound 1) was vapor-deposited to form a first hole transporting layer with a thickness of 80 nm.

On the first hole transporting layer, the compound HT2 was vapor-deposited to form a second hole transporting layer with a thickness of 10 nm.

Then, on the second hole transporting layer, the compound BH (host material) and the compound BD1 (dopant material) were vapor co-deposited to form a light emitting layer with a thickness of 25 nm. The ratio by mass of the compound BH to the compound BD1 was 96/4.

Then, on the light emitting layer, the compound ET1 and the compound ET2 were vapor co-deposited to form an electron transporting layer with a thickness of 20 nm. The ratio by mass of the compound ET1 to the compound ET2 was 50/50.

On the electron transporting layer, LiF was vapor-deposited to form an electron injecting electrode (cathode) with a thickness of 1 nm.

Then, metallic Al was vapor-deposited on the electron injecting electrode to form a metallic cathode with a thickness of 50 nm.

The layered structure of the organic EL device of Example 1 produced in the manner as above is shown below:
ITO (130)/HT1:HA=85:15 (10)/HT1 (80)/HT2 (10)/BH:BD1=96:4 (25)/ET1:ET2=50:50 (20)/LiF (1)/Al (50)

In the layered structure, the numerals in parentheses are the thickness (nm), and the ratio of HT1 to HA, the ratio of BH to BD1 and the ratio of ET1 to ET2 are by mass.

Comparative Example 1

An organic EL device of Comparative Example 1 was produced in the same manner as in Example 1 except that the comparative compound Ref-1 was used in place of the compound HT1 in the hole injecting layer and the compound HT1 in the first hole transporting layer.

Examples 2 to 6

Organic EL devices of Examples 2 to 6 were produced in the same manner as in Example 1, except that the compound BD2 (dopant) was used in place of the compound BD1 (dopant), and the compound 1 to the compound 5 were used in that order in place of the compound HT1 in the hole injecting layer and the compound HT1 in the first hole transporting layer.

In Example 2, the same compound as the compound 1 in Example 1 was used.

Comparative Examples 2 to 3

Organic EL devices of Comparative Examples 2 and 3 were produced in the same manner as in Example 1, except that the compound BD2 (dopant) was used in place of the compound BD1 (dopant), and the comparative compound Ref-2 and the comparative compound Ref-3 were used in that order in place of the compound HT1 in the hole injecting layer and the compound HT1 in the first hole transporting layer.

Evaluation of Organic EL Device

Each of the organic EL devices produced above was evaluated in point of the device lifetime thereof. The evaluation results are shown in Table 1 and Table 2.

Device Lifetime (LT95)

The resultant organic EL device was driven on DC at a current density of 50 mA/cm², and the time taken until the brightness reduced to 95% of the initial brightness was measured, and this is referred to as LT95 (95% lifetime).

TABLE 1

|  | Compound HT1 | LT95 (hr) @50 mA/cm² |
| --- | --- | --- |
| Example 1 | Compound 1 | 223 |
| Comparative Example 1 | Comparative Compound Ref-1 | 156 |

TABLE 2

|  | Compound HT1 | LT95 (hr) @50 mA/cm² |
| --- | --- | --- |
| Example 2 | Compound 1 | 177 |
| Example 3 | Compound 2 | 170 |

TABLE 2-continued

|  | Compound HT1 | LT95 (hr) @50 mA/cm² |
| --- | --- | --- |
| Example 4 | Compound 3 | 179 |
| Example 5 | Compound 4 | 181 |
| Example 6 | Compound 5 | 193 |
| Comparative Example 2 | Comparative Compound Ref-2 | 73 |
| Comparative Example 3 | Comparative Compound Ref-3 | 156 |

As is evident from the results in Table 1 and Table 2, the compound of the present invention, which has such a structure that a 9,9-dimethylfluoren-1-yl skeleton-having phenyl group, a 9,9-diphenylfluoren-2-yl skeleton, and a specific aryl group or heterocyclic group directly bond to the center nitrogen atom, has extremely prolonged device lifetime as compared with the comparative compounds Ref-1 to Ref-3 not satisfying the structural requirement in the present invention.

It is presumed that why the compound of the present invention has a longer lifetime than the comparative compound Ref-3 is because the Ar moiety in the compound of the present invention is a single ring and is therefore hardly undergo steric hindrance.

Synthesis of Intermediate 1

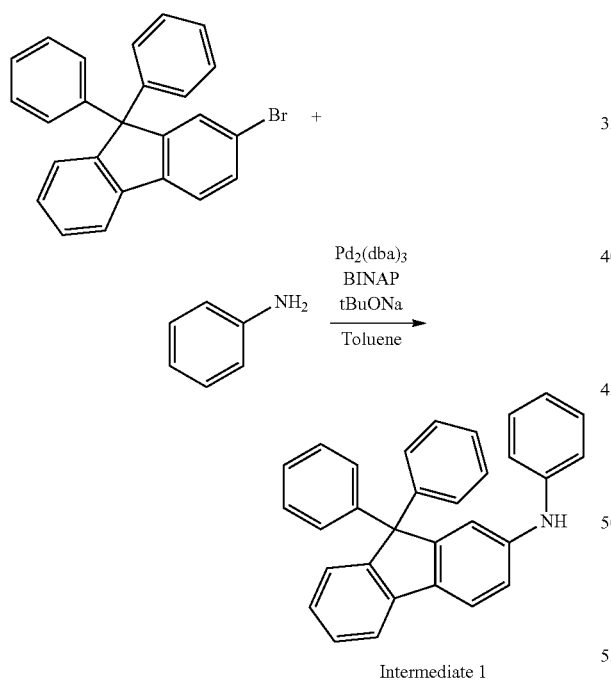

Intermediate 1

In an argon atmosphere, a mixture of 2-bromo-9,9-diphenylfluorene (795 mg, 2.0 mmol), aniline (0.55 mL, 6.0 mmol), tris(dibenzylideneacetone)dipalladium(0) (37 mg, 40 μmol), 2,2'-bis(diphenylphosphino)-1,1'-binaphthyl (BINAP) (50 mg, 80 μmol), sodium t-butoxide (269 mg, 2.8 mmol) and toluene (10 mL) was stirred with heating at 110° C. for 7 hours. After left cooled, the reaction liquid was purified through column chromatography to give an intermediate 1 (800 mg). The yield was 98%.

Synthesis of Intermediates 2 to 15

Intermediates 2 to 15 were synthesized in the same manner as that in synthesis of the intermediate 1, except that other compounds were used in place of 2-bromo-9,9-diphenylfluorene and/or aniline.

Synthesis Example 1: Synthesis of Compound 1

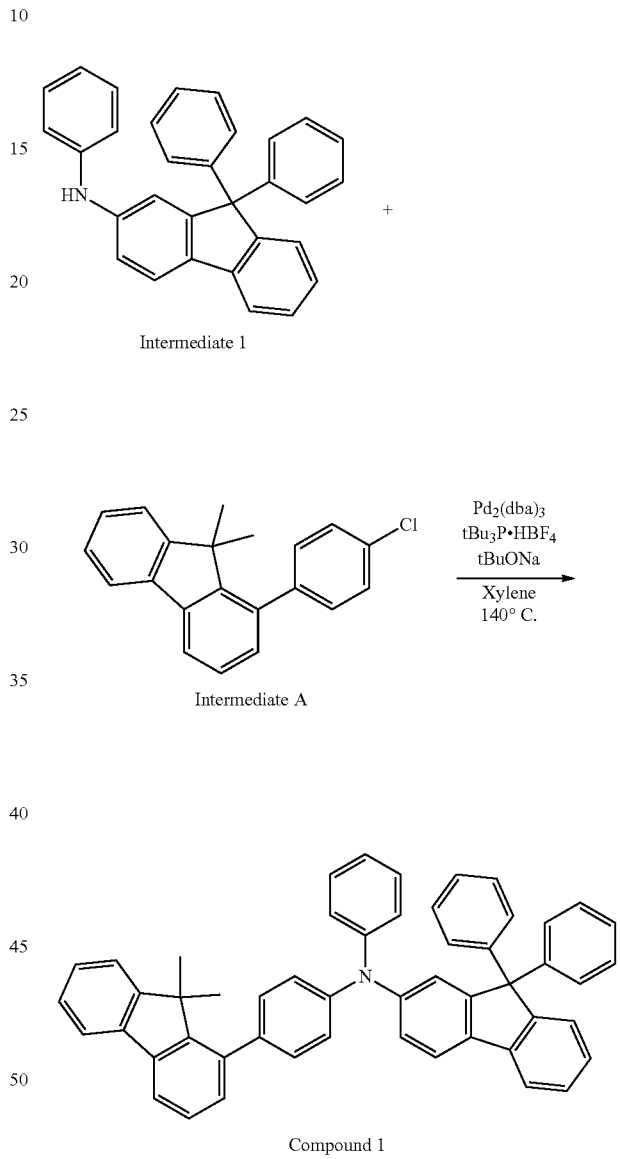

In an argon atmosphere, a mixture of the intermediate 1 (205 mg, 0.5 mmol), an intermediate A synthesized according to the method described in WO2014/015935 (152 mg, 0.5 mmol), tris(dibenzylideneacetone)dipalladium(0) (9 mg, 9.83 nmol), tri-t-butylphosphonium tetrafluoroborate (12 mg, 41 nmol), sodium t-butoxide (72 mg, 0.75 mmol) and xylene (5 mL) was stirred with heating at 140° C. for 7 hours. After left cooled, the residue was purified through column chromatography to give a compound (330 mg). The yield was 97%. As a result of mass spectrometry (m/e=677 relative to the molecular weight 677.89), the resultant compound was a compound 1.

Synthesis Example 2: Synthesis of Compound 2

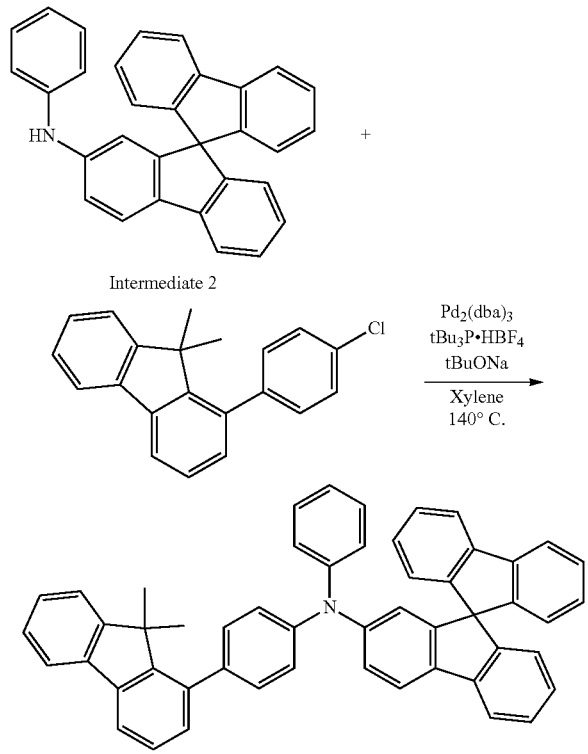

Intermediate 2

Compound 2

A compound was produced according to the same operation as in Synthesis Example 1 except that an intermediate 2 was used in place of the intermediate 1.

As a result of mass spectrometry (m/e=675 relative to the molecular weight 675.88), the resultant compound was a compound 2. The yield is 95%.

Synthesis Example 3: Synthesis of Compound 3

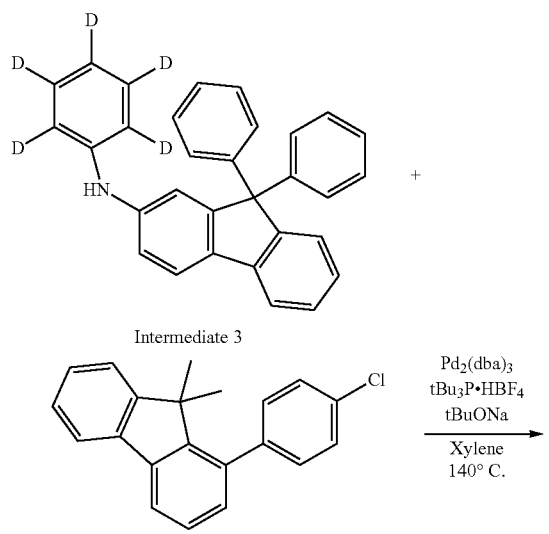

Intermediate 3

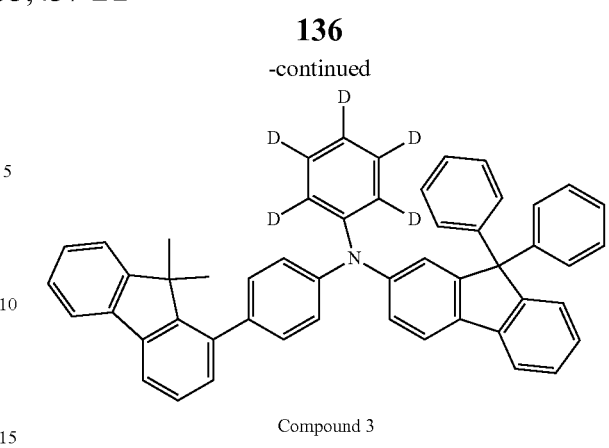

Compound 3

A compound was produced according to the same operation as in Synthesis Example 1 except that an intermediate 3 was used in place of the intermediate 1.

As a result of mass spectrometry (m/e=682 relative to the molecular weight 682.92), the resultant compound was a compound 3. The yield was 94%.

Synthesis Example 4: Synthesis of Compound 4

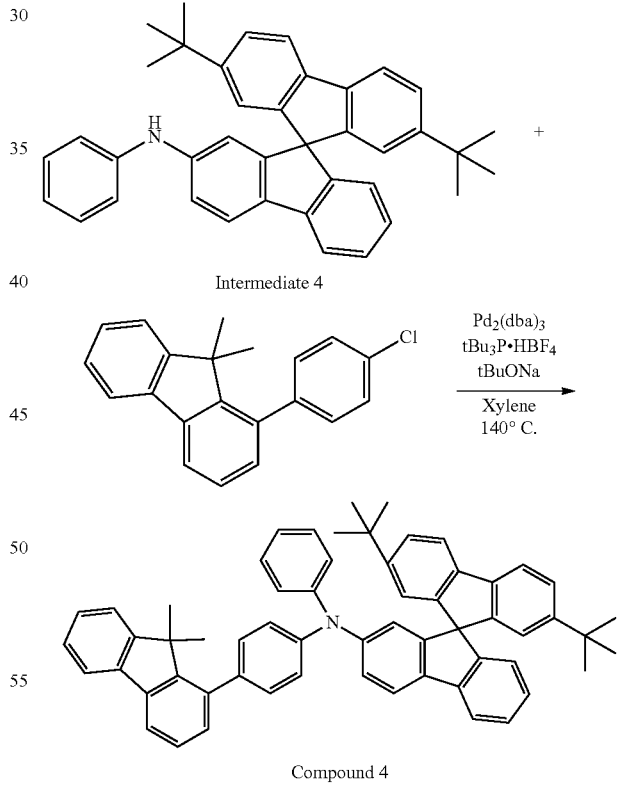

Intermediate 4

Compound 4

A compound was produced according to the same operation as in Synthesis Example 1 except that an intermediate 4 was used in place of the intermediate 1.

As a result of mass spectrometry (m/e=788 relative to the molecular weight 788.09), the resultant compound was a compound 4. The yield was 95%.

Synthesis Example 5: Synthesis of Compound 5

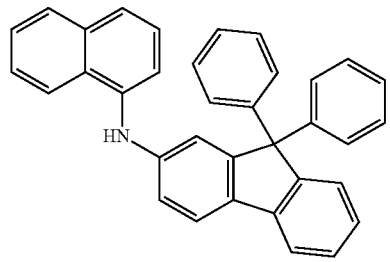

Intermediate 5

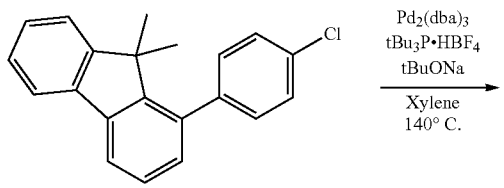

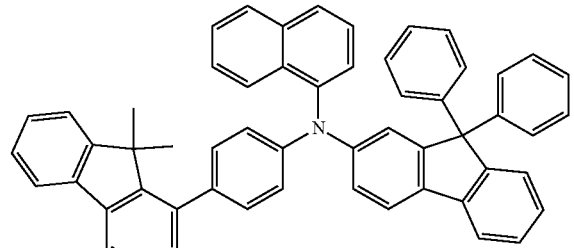

Compound 5

A compound was produced according to the same operation as in Synthesis Example 1 except that an intermediate 5 was used in place of the intermediate 1.

As a result of mass spectrometry (m/e=727 relative to the molecular weight 727.95), the resultant compound was a compound 5. The yield was 90%.

Synthesis Example 6: Synthesis of Compound 6

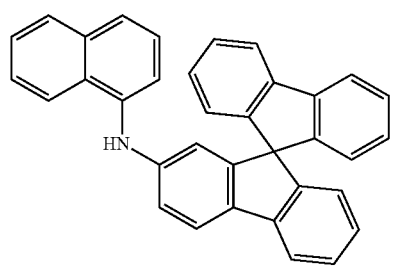

Intermediate 6

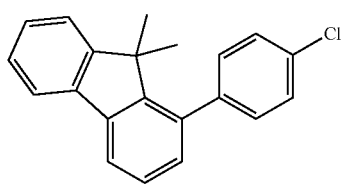

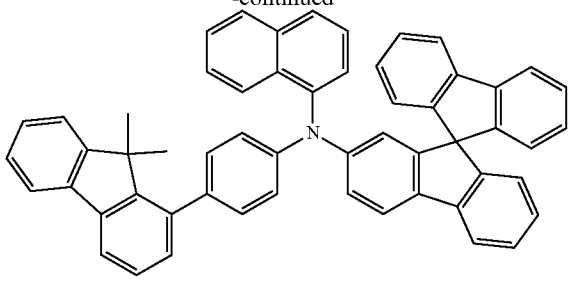

Compound 6

A compound was produced according to the same operation as in Synthesis Example 1 except that an intermediate 6 was used in place of the intermediate 1.

As a result of mass spectrometry (m/e=725 relative to the molecular weight 725.94), the resultant compound was a compound 6. The yield was 89%.

Synthesis Example 7: Synthesis of Compound 7

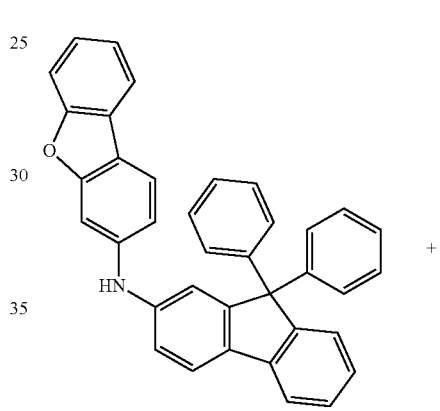

Intermediate 7

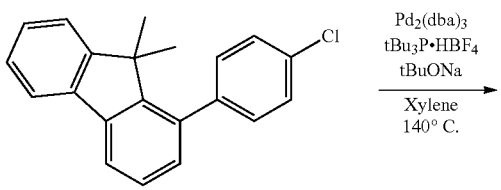

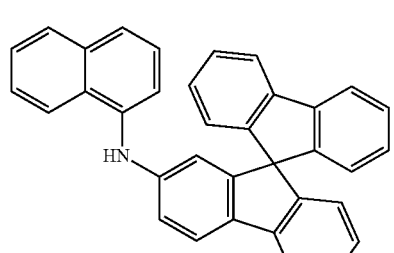

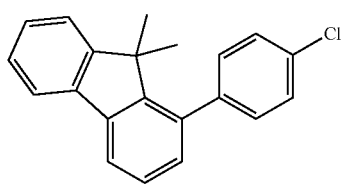

Compound 7

A compound was produced according to the same operation as in Synthesis Example 1 except that an intermediate 7 was used in place of the intermediate 1.

As a result of mass spectrometry (m/e=767 relative to the molecular weight 767.97), the resultant compound was a compound 7. The yield was 85%.

Synthesis Example 8: Synthesis of Compound 8

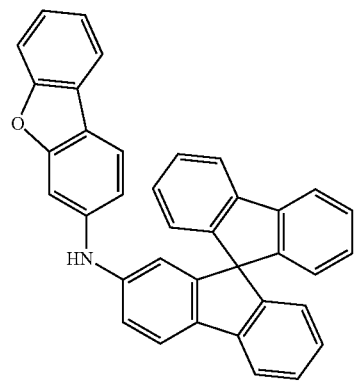

Intermediate 8

Synthesis Example 9: Synthesis of Compound 9

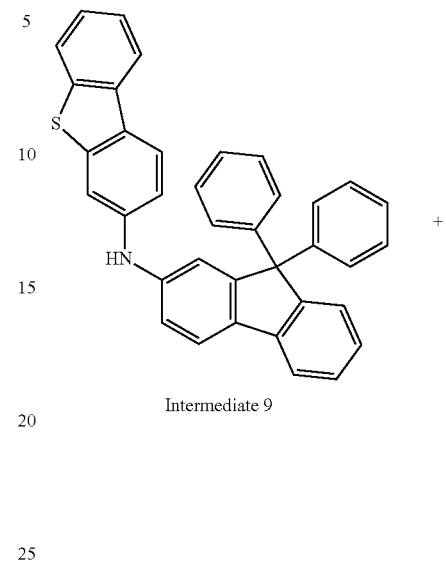

Intermediate 9

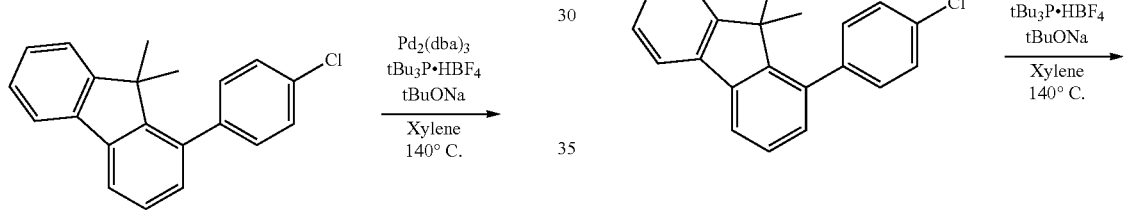

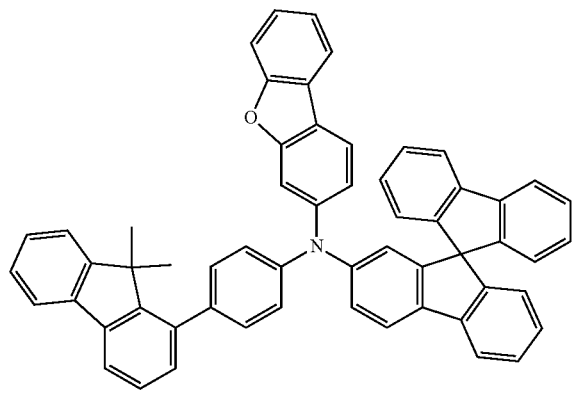

Compound 8

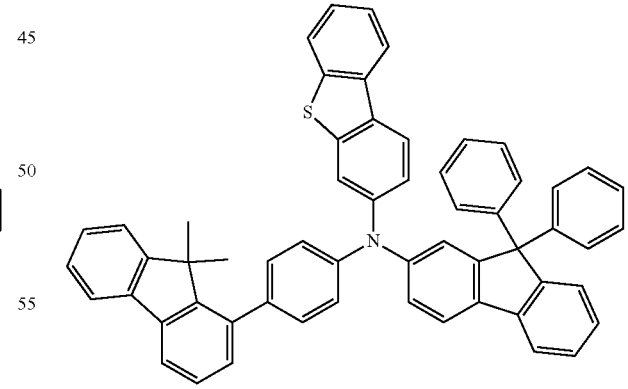

Compound 9

A compound was produced according to the same operation as in Synthesis Example 1 except that an intermediate 8 was used in place of the intermediate 1.

As a result of mass spectrometry (m/e=765 relative to the molecular weight 765.96), the resultant compound was a compound 8. The yield was 82%.

A compound was produced according to the same operation as in Synthesis Example 1 except that an intermediate 9 was used in place of the intermediate 1.

As a result of mass spectrometry (m/e=784 relative to the molecular weight 784.03), the resultant compound was a compound 9. The yield was 87%.

Synthesis Example 10: Synthesis of Compound 10

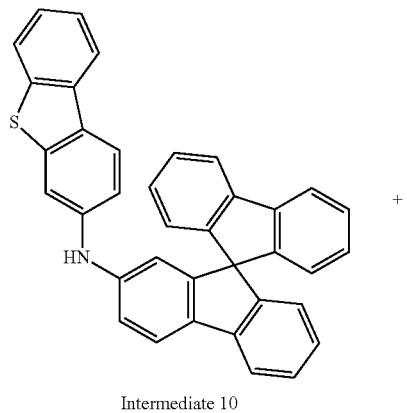

Intermediate 10

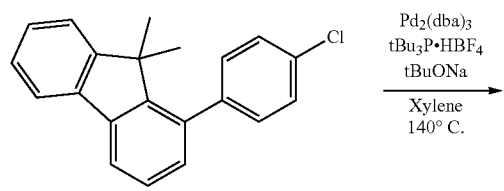

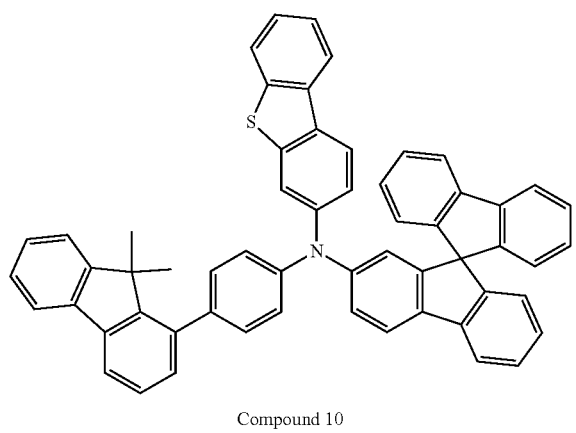

Compound 10

A compound was produced according to the same operation as in Synthesis Example 1 except that an intermediate 10 was used in place of the intermediate 1.

As a result of mass spectrometry (m/e=782 relative to the molecular weight 782.02), the resultant compound was a compound 10. The yield was 81%.

Synthesis Example 11: Synthesis of Compound 11

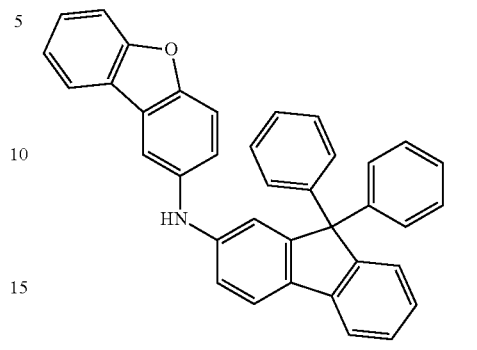

Intermediate 11

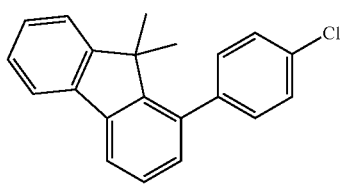

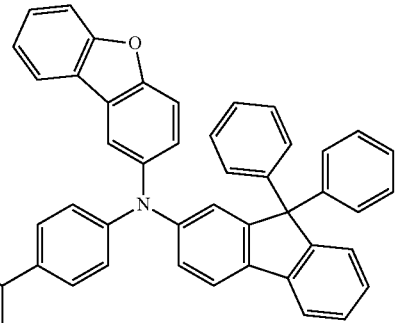

Compound 11

A compound was produced according to the same operation as in Synthesis Example 1 except that an intermediate 11 was used in place of the intermediate 1.

As a result of mass spectrometry (m/e=767 relative to the molecular weight 767.97), the resultant compound was a compound 11. The yield was 92%.

Synthesis Example 12: Synthesis of Compound 12

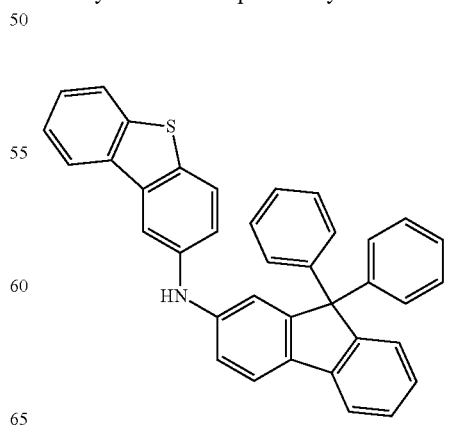

Intermediate 12

-continued

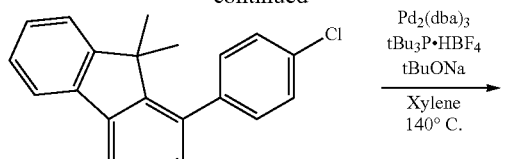

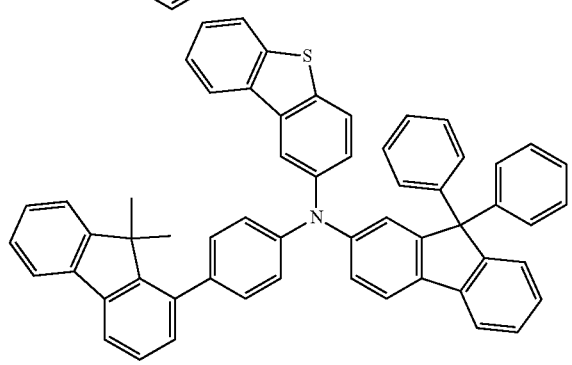

Compound 12

A compound was produced according to the same operation as in Synthesis Example 1 except that an intermediate 12 was used in place of the intermediate 1.

As a result of mass spectrometry (m/e=784 relative to the molecular weight 784.03), the resultant compound was a compound 12. The yield was 89%.

Synthesis Example 13: Synthesis of Compound 13

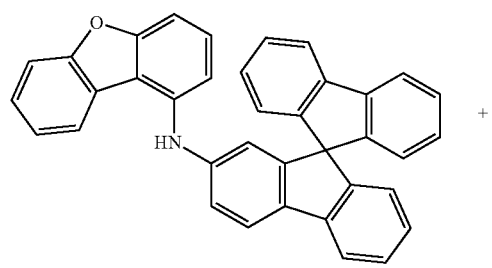

Intermediate 13

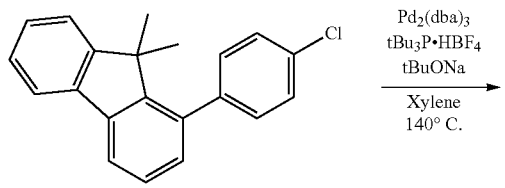

Compound 13

A compound was produced according to the same operation as in Synthesis Example 1 except that an intermediate 13 was used in place of the intermediate 1.

As a result of mass spectrometry (m/e=756 relative to the molecular weight 756.96), the resultant compound was a compound 13. The yield was 78%.

Synthesis Example 14: Synthesis of Compound 14

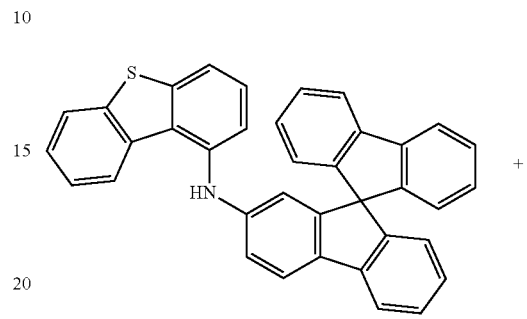

Intermediate 14

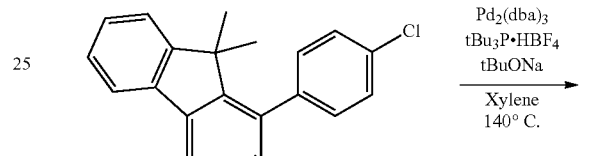

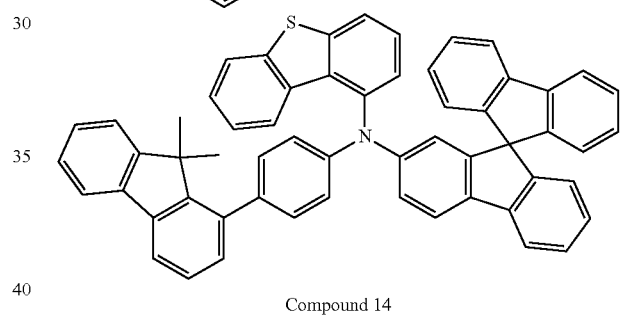

Compound 14

A compound was produced according to the same operation as in Synthesis Example 1 except that an intermediate 14 was used in place of the intermediate 1.

As a result of mass spectrometry (m/e=782 relative to the molecular weight 782.02), the resultant compound was a compound 14. The yield was 71%.

Synthesis Example 15: Synthesis of Compound 15

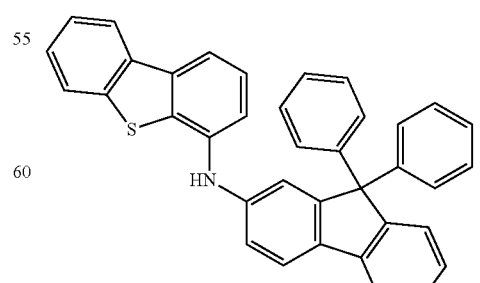

Intermediate 15

-continued

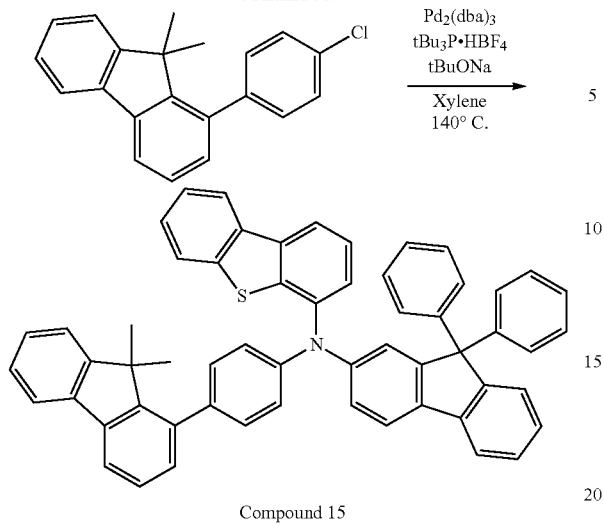

Compound 15

A compound was produced according to the same operation as in Synthesis Example 1 except that an intermediate 15 was used in place of the intermediate 1.

As a result of mass spectrometry (m/e=784 relative to the molecular weight 784.03), the resultant compound was a compound 15. The yield was 73%.

REFERENCE SIGNS LIST 1, 11: Organic EL device
2: Substrate
3: Anode
4: Cathode
5: Light emitting layer
6: Hole transporting region (hole transporting layer)
6a: First hole transporting layer
6b: Second hole transporting layer
7: Electron transporting region (electron transporting layer)
7a: First electron transporting layer
7b: Second electron transporting layer
10, 20: Emission unit

The invention claimed is:

1. A compound represented by the following formula (I):

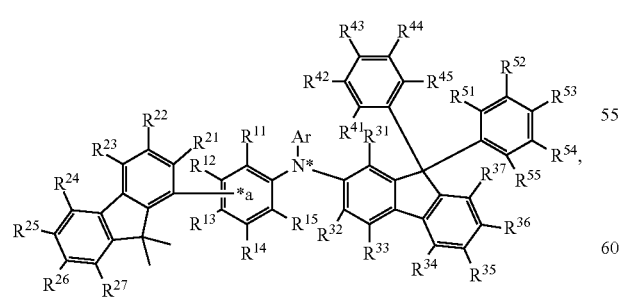

wherein
N* represents a center nitrogen atom;
Ar represents a group represented by any of the following formulae (2) to (4);

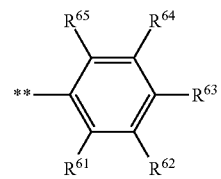

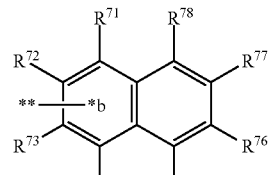

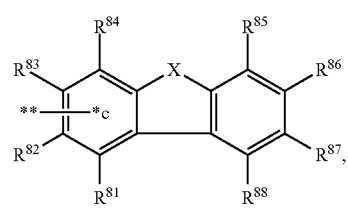

X represents an oxygen atom or a sulfur torn;
$R^{61}$ to $R^{65}$, $R^{71}$ to $R^{78}$, and $R^{81}$ to $R^{88}$ each are independently selected from the group consisting of a hydrogen atom, a substituted or unsubstituted alkyl group having 1 to 50 carbon atoms, a substituted or unsubstituted cycloalkyl group having 3 to 50 ring carbon atoms, a group represented by —Si$(R_{901})(R_{902})(R_{903})$, a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group,
provided that one selected from $R^{71}$ to $R^{78}$ is a single bond bonding to *b, one selected from $R^{81}$ to $R^{88}$ is a single bond bonding to *c, and ** represents a bonding position to the center nitrogen atom N*;
$R^{11}$ to $R^{15}$, $R^{21}$ to $R^{27}$, $R^{41}$ to $R^{45}$, and $R^{51}$ to $R^{55}$ each are independently selected from the group consisting of a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si$(R_{901})(R_{902})(R_{903})$, a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group,
provided that one selected from $R^{11}$ to $R^{15}$ is a single bond bonding to *a;

$R^{31}$ to $R^{37}$ each are independently selected from the group consisting of a hydrogen atom, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by $-Si(R_{901})(R_{902})(R_{903})$, a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group;

$R_{901}$, $R_{902}$, and $R_{903}$ each are independently selected from the group consisting of a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms;

at least one pair of combinations formed of neighboring two or more selected from $R^{21}$ to $R^{27}$ and $R^{31}$ to $R^{37}$ bond to each other to form a substituted or unsubstituted single ring, or bond to each other to form a substituted or unsubstituted condensed ring, or do not bond to each other;

$R^{45}$ and $R^{51}$ bond to each other to form a single bond that bonds the two benzene rings to which they bond, or do not bond to each other.

2. The compound according to claim 1, represented by any of the following formulae (5) to (7):

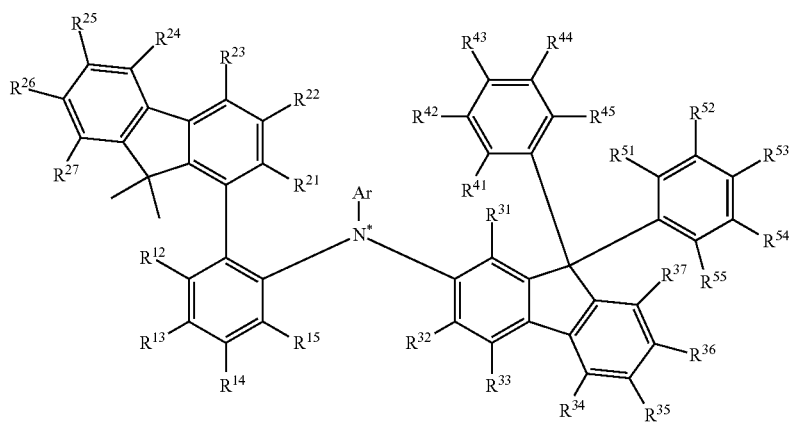

(5)

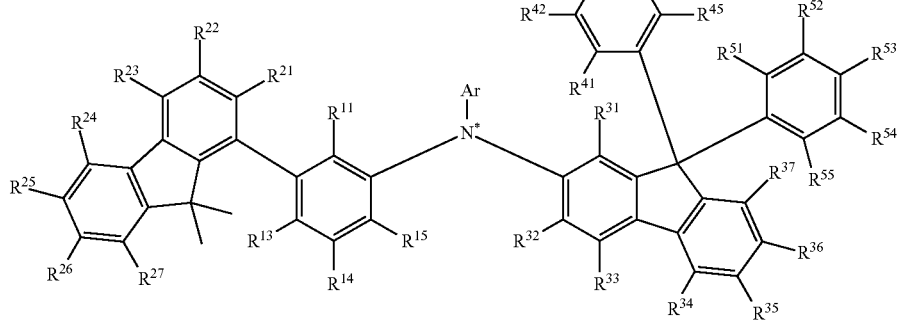

(6)

-continued
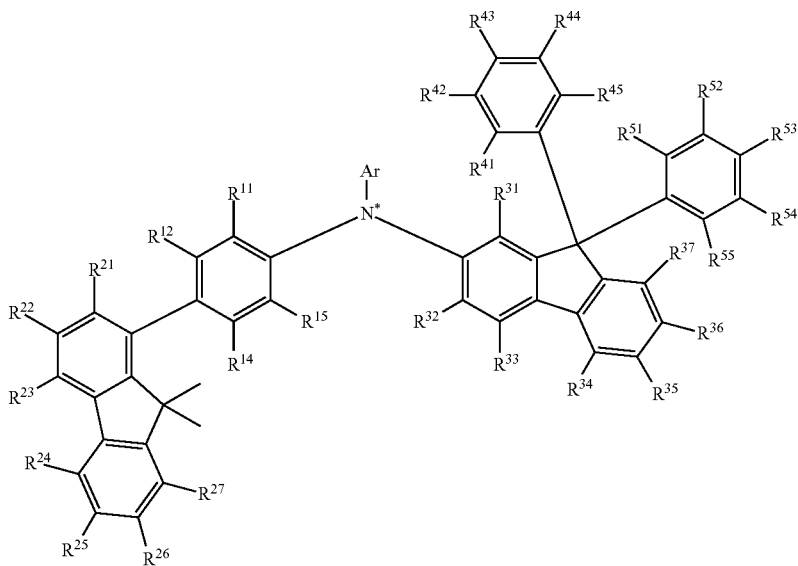
(7)
wherein N*, Ar, $R^{11}$ to $R^{15}$, $R^{21}$ to $R^{27}$, $R^{31}$ to $R^{37}$, $R^{41}$ to $R^{45}$, and $R^{51}$ to $R^{55}$ are as defined in the formula (1).
3. The compound according to claim 1, wherein Ar is a group represented by the formula (2).
4. The compound according to claim 1, represented by any of the following formulae (8) to (10):
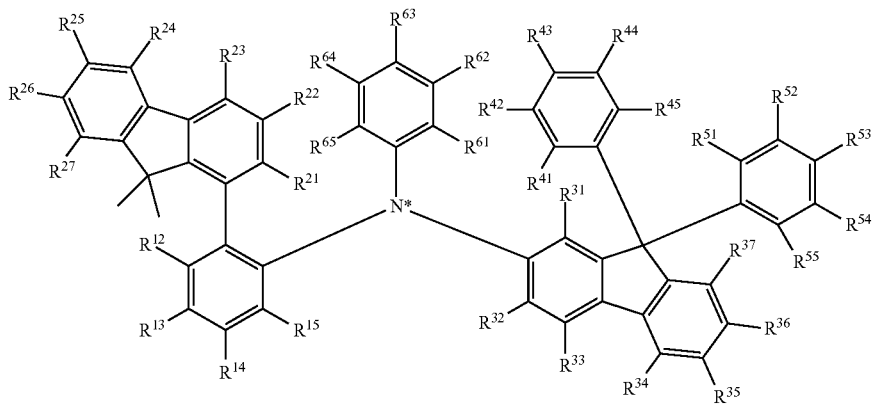
(8)
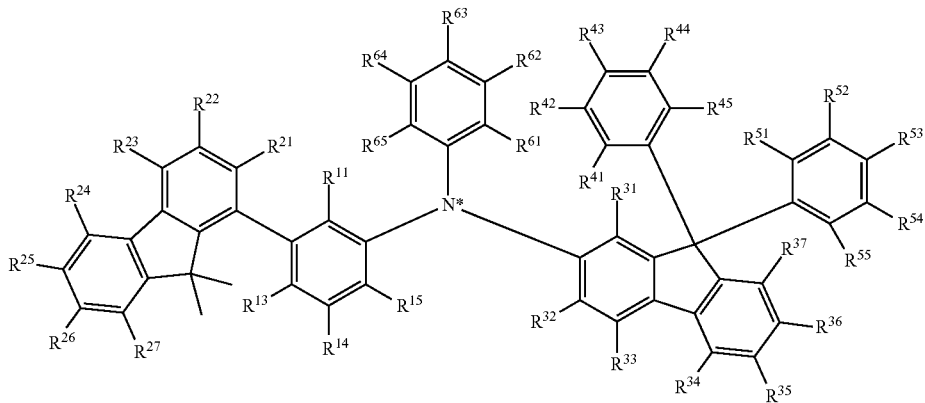
(9)

(10)
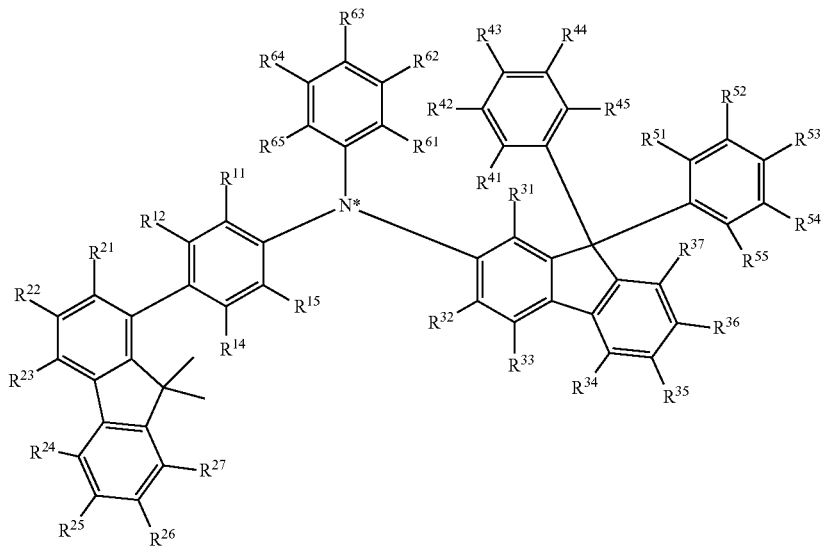
wherein N*, $R^{11}$ to $R^{15}$, $R^{21}$ to $R^{27}$, $R^{31}$ to $R^{37}$, $R^{41}$ to $R^{45}$, $R^{51}$ to $R^{55}$, and $R^{61}$ to $R^{65}$ are as defined in the formula (1).
5. The compound according to claim 1, wherein Ar is a group represented by the formula (3).
6. The compound according to claim 1, represented by any of the following formulae (11) to (13):
(11)
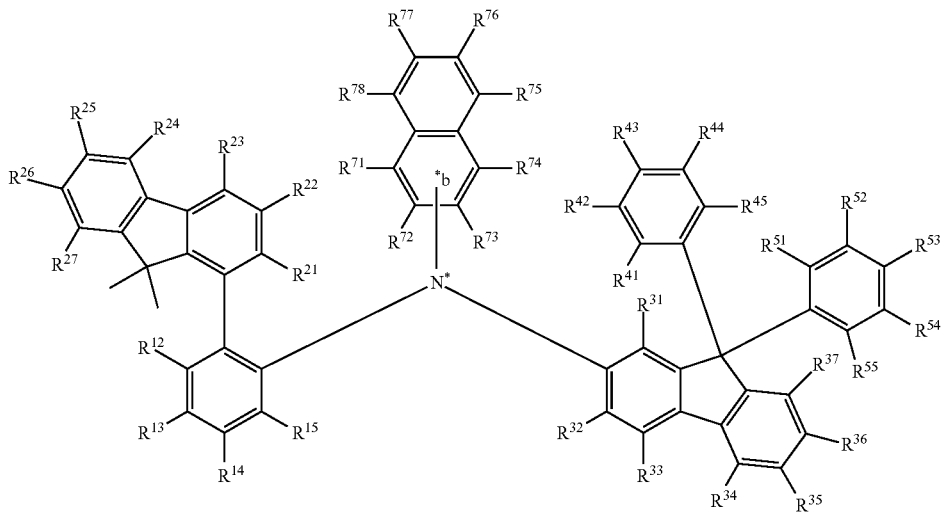

(12)

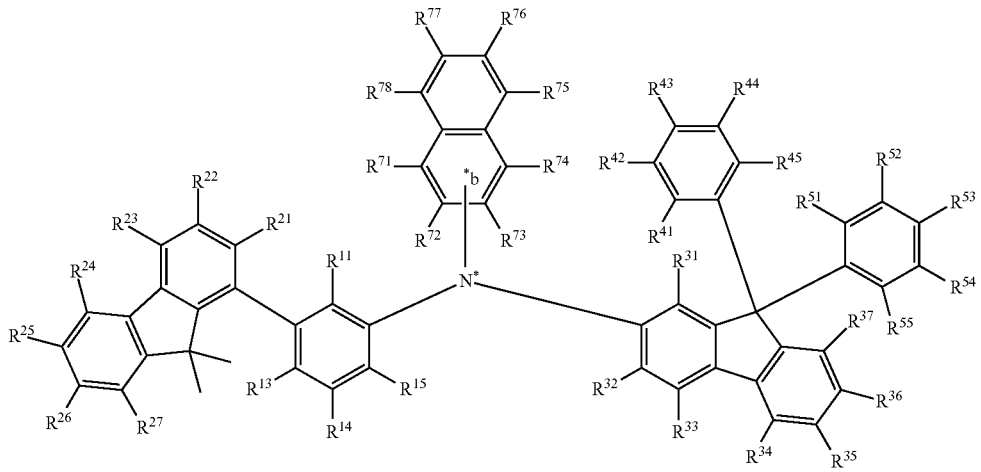

(13)

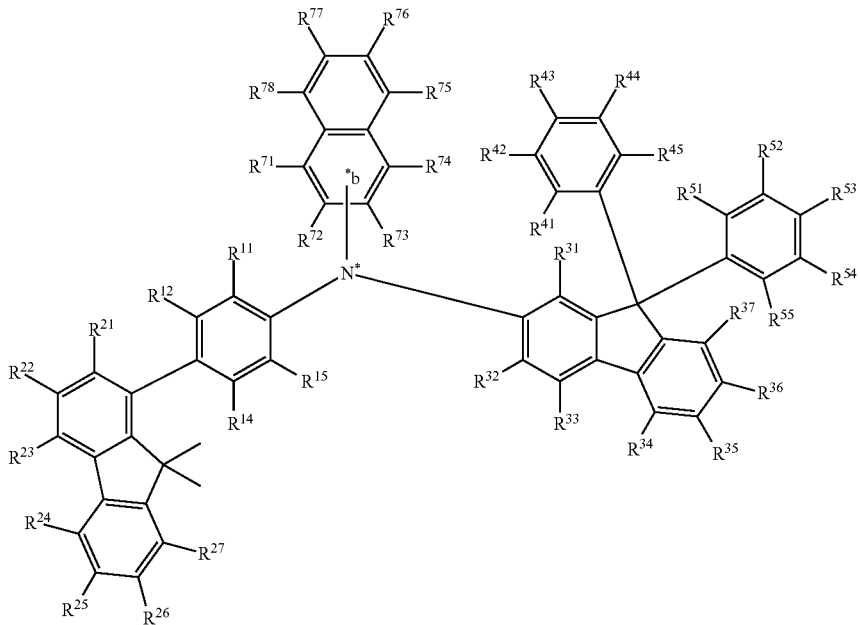

wherein N*, *b, $R^{11}$ to $R^{15}$, $R^{21}$ to $R^{27}$, $R^{31}$ to $R^{37}$, $R^{41}$ to $R^{45}$, $R^{51}$ to $R^{55}$, and $R^{71}$ to $R^{78}$ are as defined in the formula (1).

7. The compound according to claim 1, wherein Ar is represented by the following formula (3a) or (3b):

(3a)

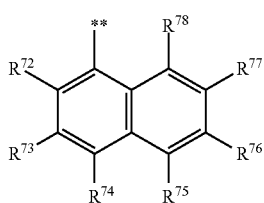

(3b)

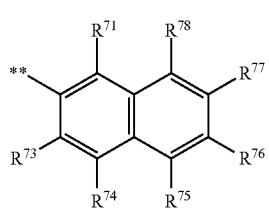

wherein $R^{71}$ to $R^{78}$ and ** are as defined in the formula (1).

8. The compound according to claim 1, wherein Ar is a group represented by the formula (4).

9. The compound according to claim 1, represented by any of the following formulae (14) to (16):

(14)
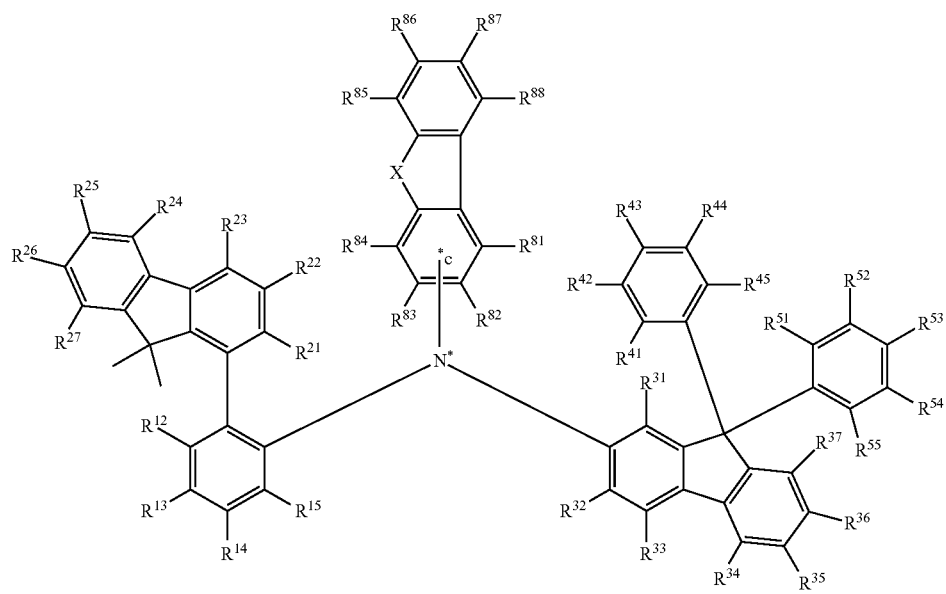
(15)
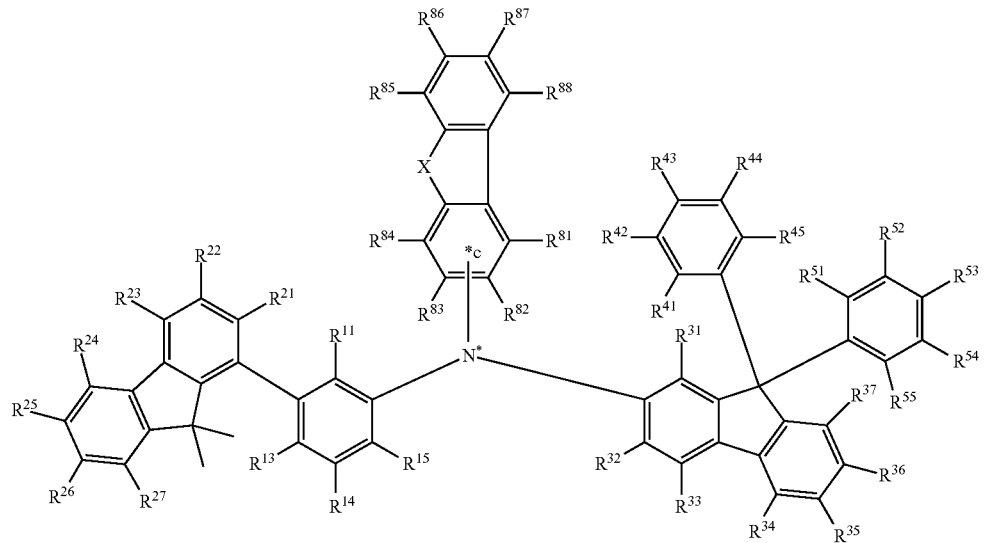

(16)

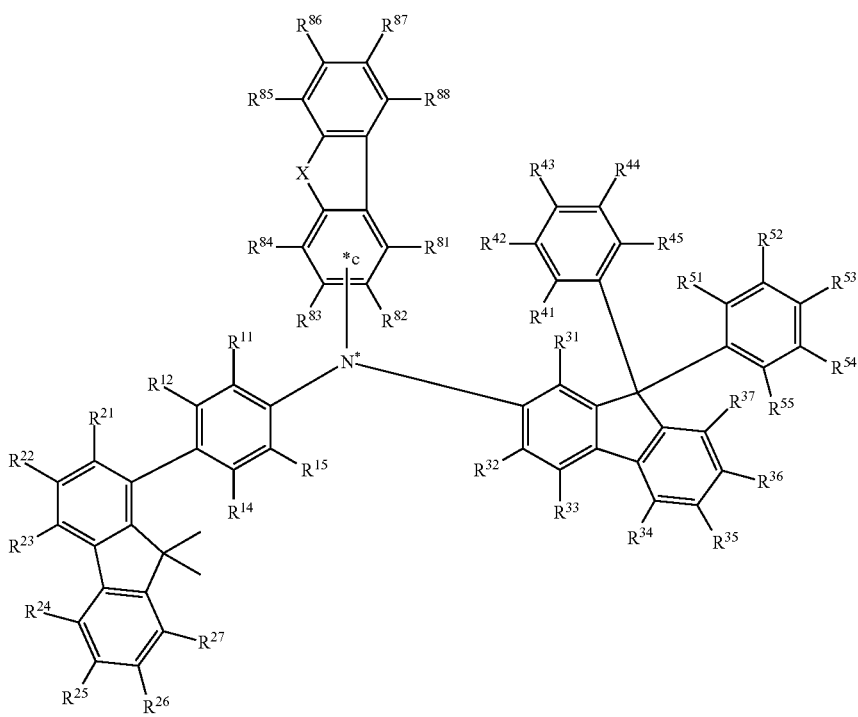

wherein N*, *c, $R^{11}$ to $R^{15}$, $R^{21}$ to $R^{27}$, $R^{31}$ to $R^{37}$, $R^{41}$ to $R^{45}$, $R^{51}$ to $R^{55}$, and $R^{81}$ to $R^{88}$ are as defined in the formula (1).

10. The compound according to claim 1, wherein Ar is a group represented by any of the following formulae (4a) to (4d):

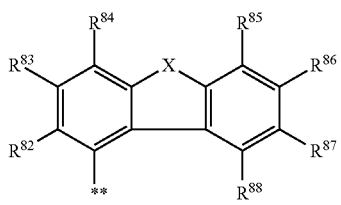
(4a)

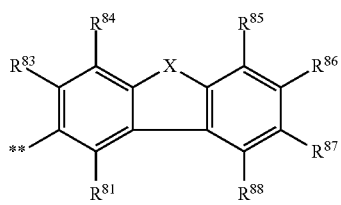
(4b)

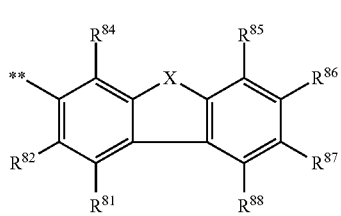
(4c)

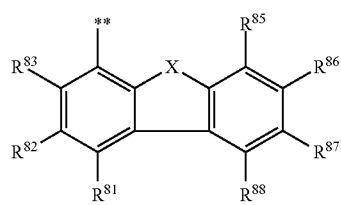
(4d)

wherein X, $R^{81}$ to $R^{88}$, and ** are as defined in the formula (1).

11. The compound according to claim 1, wherein the substituted or unsubstituted aryl group having 6 to 50 ring carbon atoms, which $R^{11}$ to $R^{15}$, $R^{21}$ to $R^{27}$, $R^{41}$ to $R^{45}$, $R^{51}$ to $R^{55}$, $R_{901}$, $R_{902}$, and $R_{903}$ represent, is selected from the groups consisting of a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, and a 9,9-diphenylfluorenyl group.

12. The compound according to claim 1, wherein the substituted or unsubstituted heterocyclic group having 5 to 50 ring atoms, which $R^{11}$ to $R^{15}$, $R^{21}$ to $R^{27}$, $R^{31}$ to $R^{37}$, $R^{41}$ to $R^{45}$, $R^{51}$ to $R^{55}$, $R_{901}$, $R_{902}$, and $R_{903}$ represent, is selected from the group consisting of a pyridyl group, a pyrimidinyl group, a triazinyl group, a quinolyl group, an isoquinolyl group, a quinazolyl group, a benzimidazolyl group, a phenanthrolinyl group, a carbazolyl group, a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group, a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, and a phenyldibenzothiophenyl group.

13. The compound according to claim 1, wherein the substituted or unsubstituted alkyl group having 1 to 50 carbon atoms, which $R^{11}$ to $R^{15}$, $R^{21}$ to $R^{27}$, $R^{31}$ to $R^{37}$, $R^{41}$ to $R^{45}$, $R^{51}$ to $R^{55}$, $R^{61}$ to $R^{65}$, $R^{71}$ to $R^{78}$, $R^{81}$ to $R^{88}$, $R_{901}$, $R_{902}$, and $R_{903}$ represent, is selected from the group consisting of a methyl group, an ethyl group, a n-propyl group, an isopropyl group, a n-butyl group, an isobutyl group, a s-butyl group, a t-butyl group, a heptafluoropropyl group, a pentafluoroethyl group, a 2,2,2-trifluoroethyl group and a trifluoromethyl group.

14. The compound according to claim 1, wherein $R^{45}$ and $R^{51}$ do not bond to each other.

15. The compound according to claim 1, wherein $R^{45}$ and $R^{51}$ bond to each other to form a single bond that bonds the two benzene rings to which they bond.

16. The compound according to claim 1, wherein all $R^{11}$ to $R^{15}$ that are not a single bond to bond to *a are hydrogen atoms.

17. The compound according to claim 1, wherein all $R^{21}$ to $R^{27}$ are hydrogen atoms.

18. The compound according to claim 1, wherein all $R^{31}$ to $R^{37}$ are hydrogen atoms.

19. The compound according to claim 1, wherein all $R^{41}$ to $R^{45}$ and $R^{51}$ to $R^{55}$ are hydrogen atoms.

20. The compound according to claim 1, wherein all $R^{61}$ to $R^{65}$ are hydrogen atoms.

21. The compound according to claim 1, wherein all $R^{71}$ to $R^{78}$ that are not a single bond to bond to *b are hydrogen atoms.

22. The compound according to claim 1, wherein all $R^{81}$ to $R^{88}$ that are not a single bond to bond to *c are hydrogen atoms.

23. The compound according to claim 1, wherein the compound comprises at least one heavy hydrogen atom.

24. A material for organic electroluminescent devices, comprising the compound of claim 1.

25. An organic electroluminescent device comprising an anode, a cathode, and an organic layer arranged between the anode and the cathode, wherein the organic layer comprises a light-emitting layer, and at least one layer of the organic layer comprises the compound of claim 1.

26. The organic electroluminescent device according to claim 25, wherein the compound comprises at least one heavy hydrogen atom.

27. The organic electroluminescent device according to claim 25, wherein the organic layer comprises a hole transporting region between the anode and the light emitting layer, and the hole transporting region comprises the compound.

28. The organic electroluminescent device according to claim 25, wherein the hole transporting region comprises a first hole transporting layer on the anode side and a second hole transporting layer on the cathode side, and the first hole transporting layer, the second hole transporting layer, or the first and second hole transporting layers comprise the compound.

29. The organic electroluminescent device according to claim 25, wherein the light emitting layer comprises a fluorescent dopant material.

30. An electronic device comprising the organic electroluminescent device of claim 25.

* * * * *